(12) United States Patent
Horwitz et al.

(10) Patent No.: US 8,206,700 B2
(45) Date of Patent: Jun. 26, 2012

(54) METHODS AND COMPOSITIONS FOR TREATING TULAREMIA

(75) Inventors: Marcus A. Horwitz, Los Angeles, CA (US); Qingmei Jia, Beverly Hills, CA (US); Bai-Yu L. Clemens, Los Angeles, CA (US); Daniel Clemens, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 339 days.

(21) Appl. No.: 12/446,222

(22) PCT Filed: Oct. 22, 2007

(86) PCT No.: PCT/US2007/022418
§ 371 (c)(1),
(2), (4) Date: Apr. 17, 2009

(87) PCT Pub. No.: WO2008/127296
PCT Pub. Date: Oct. 23, 2008

(65) Prior Publication Data
US 2010/0215679 A1   Aug. 26, 2010

Related U.S. Application Data

(60) Provisional application No. 60/854,612, filed on Oct. 25, 2006.

(51) Int. Cl.
*A01N 63/00* (2006.01)
*A01N 65/00* (2009.01)

(52) U.S. Cl. .................. 424/93.1; 424/93.2; 424/93.4

(58) Field of Classification Search ................ None
See application file for complete search history.

(56) References Cited

U.S. PATENT DOCUMENTS

| | | | |
|---|---|---|---|
| 7,803,363 B2 * | 9/2010 | Klose et al. ............... | 424/93.2 |
| 2003/0153527 A1 | 8/2003 | Powell et al. | |
| 2005/0063952 A1 | 3/2005 | Klysner et al. | |

FOREIGN PATENT DOCUMENTS

| | | |
|---|---|---|
| WO | WO 2004/003009 A2 | 1/2004 |
| WO | 2008012538 A2 | 1/2008 |
| WO | 2010129457 A2 | 11/2010 |

OTHER PUBLICATIONS

Sjostedt et al (Infection and Immunity vol. 60, No. 7, pp. 2855-2862, 1992).*
Pammit et al (12th International Congress of Mucosal Immunity, Jun. 2005).*
Lauriano et al (FEMS Microbiology Letters vol. 229, pp. 195-202, 2003).*
Janovska, S. at al "Identification of immunoreactive antigens in membrane proteins enriched fraction from *Francisella tularensis* LVS", Immunology letters, 2007, vol. 108, pp. 151-159.
Jia, Q. et al., "Recombinant attenuated Listeria monocytogenes vaccine expressing *Francisella tularensis* IglC induces protection in mice against aerosolized Type A *F tularensis*", Vaccine, Jan. 4, 2009, vol. 27, pp. 1216-1229.
Lee, Soo-Jung, International Search Report and Written Opinion, date of mailing of report: Feb. 25, 2011, International Application Number: PCT/US2010/033,352.
Giffo-Schmitt, Beate, International Preliminary Report on Patentability and Written Opinion, Date of Issuance Report Apr. 28, 2009, International Application Number PCT/US07/22418.
Young, Lee W., International Search Report and Written Opinion, Date of Mailing of Search Report Dec. 31, 2008, International Application No: PCT/US07/22418, 10 pages.
Lee et al "Identification, recombinant expression, immunolocalization in macrophages, and T-cell responsiveness of the major extracellular proteins of *Francisella tularensis*," Infection and Immunity, Jul. 2006, pp. 4002-4013, vol. 74.
Santic, Marina et al., "The *Francisella tularensis* pathogenicity island protein IgIC and its regulator MgIA are essential for modulating phagosome biogenesis and subsequent bacterial escape into the cytoplasm," Cellular Microbiology, 2005, pp. 969-979.

* cited by examiner

*Primary Examiner* — Albert Navarro
(74) *Attorney, Agent, or Firm* — Joseph R. Baker, Jr.; Gavrilovich Dodd & Lindsey LLP

(57) ABSTRACT

The disclosure provides an antigenic composition useful for immunization against tularemia. The disclosure provides a method for producing a vaccine for preventing tularemia in humans and animals, a new vaccine against tularemia in humans and animals, and a new approach to producing vaccines against tularemia.

12 Claims, 10 Drawing Sheets acpA (SEQ ID NO:1 and 2)

ATGAAGCTCAATAAAATTACTTTAGGAATTTTAAGTCTAAGTATCGCAACAACGACTTTTGCCACAGAT
GTGAATAATAGCAAACCAAATGATTATGGAACTCTTGTAAAAATAAAACAAAAATTATTTAATAATGCG
AATACTCTAAAAACTACAACTCCAATAAAGCACGTAGTAATAATATTCCAAGAGAATAACTCTTTTGAT
AGATACTTTGGAATGTACCCCAATGCCAAAAACCCAGAGGGTGAGCCAAAATTTGTAGCCAAAGAAAAT
ACTCCAAATGTTAATGGTCTGACAAAACAATTATTAGAGAATAATCCAAATACAAAAAATCCTTATCGT
TTAGATAGAAATTTCCAACCTTGCTCACAAAATCATGAGTACCATCAAGAAATTCTTCTTTTAATGGT
GGATTAATGAACAAATTTGTTGAACATGGTGGTCATGATAATGACACCTATAAACAAAACTGTGATGGT
CAAGTCATGGGATATTATGATGGTAATACTGTCACAGCATTATGGAATTACGCACAAAATTTCGCTCTA
AATGATAATACGTTTGGTACAACTTTTGGTCCATCAACACCTGGTGCCCTTAACCTAGTGGCTGGTGCA
AATGGTCCAGCAATGAGTCCAAGTGGTAATTTAGAAAATATTGAAAACAGCTATATCATTGATGATCCT
AACCCATACTACGATGATTGCTCTTATGGTACAAGTAAATCTGGCGATACAAATACAGCTGTAGCAAAA
ATTACTGATGGTTATAATATTGGACACTATCTAACTCAAAAAGGTATTACTTGGGGTTGGTTCCAAGGA
GGATTCAAACCAACAAGCTACTCTGGTAAAACAGCAATATGTGATGCTATGAGCACTAATAAGTTCGGT
ATAAAATCAAGAGACTATATACCTCATCATGAGCCTTTTAACTATTGGAAAGAGACATCAAACCCTCAT
CATCTAGCACCAAGTGATGATAAGTATATAGGTAGTAATGACCAAGCTAACCATCAGTACGACATAAGT
GAATTTTGGAAGGCTCTTGATCAAAACACCATGCCTGCGGTAAGTTACTTAAAAGCTCCTGGATATCAA
GATGGTCATGGAGGCTACTCAAACCCTCTAGATGAACAAGAATGGCTAGTCAATACTATTAATAGAATC
AAACAATCAAAAGACTGGGATAGCACAGCAATTATAATTATTTATGATGACTCTGATGGTGACTATGAC
CATGTCTACAGTCCAAAATCACAGTTTAGCGATATTAAAGGAAGACAAGGCTATGGACCAAGATTACCA
ATGCTTGTTATTTCTCCTTATACTAAAGCAAACTATATTGATCATTCATTACTTAATCAAGCATCTGTA
CTTAAGTTTATAGAGTATAACTGGGGCATTGGCTCAGTTAGTAAGTATAGTAATGATAAATACTCAAAC
AATATCTTAAACATGTTTGATTTAATAAAAAACAAAAAACACCAAAACTGATTTTAGACCCTAAGACA
GGATTAGTAGTGGATAAATTAAACTAA

| MKLNKITLGI | LSLSIATTTF | ATDVNNSKPN | DYGTLVKIKQ | KLFNNANTLK | 50  |
| TTTPIKHVVI | IFQENNSFDR | YFGMYPNAKN | PEGEPKFVAK | ENTPNVNGLT | 100 |
| KQLLENNPNT | KNPYRLDRNF | QPCSQNHEYH | QEISSFNGGL | MNKFVEHGGH | 150 |
| DNDTYKQNCD | GQVMGYYDGN | TVTALWNYAQ | NFALNDNTFG | TTFGPSTPGA | 200 |
| LNLVAGANGP | AMSPSGNLEN | IENSYIIDDP | NPYYDDCSYG | TSKSGDTNTA | 250 |
| VAKITDGYNI | GHYLTQKGIT | WGWFQGGFKP | TSYSGKTAIC | DAMSTNKFGI | 300 |
| KSRDYIPHHE | PFNYWKETSN | PHHLAPSDDK | YIGSNDQANH | QYDISEFWKA | 350 |
| LDQNTMPAVS | YLKAPGYQDG | HGGYSNPLDE | QEWLVNTINR | IKQSKDWDST | 400 |
| AIIIYDDSD | GDYDHVYSPK | SQFSDIKGRQ | GYGPRLPMLV | ISPYTKANYI | 450 |
| DHSLLNQASV | LKFIEYNWGI | GSVSKYSNDK | YSNNILNMFD | FNKKQKTPKL | 500 |
| ILDPKTGLVV | DKLN!      |            |            |            |     |

Bfr (SEQ ID NO:3 and 4)

ATGTTGATTATAATGATTAGAGTTTTAAATAATGGAGATAACAATATGGAACTTCAATTAGAAAATAAA
CAAGAAATTATTGATCAATTAAATAAAATCTTAGAACTCGAAATGTCTGGAGTTGTGCGTTATACTCAT
TATTCTTTAATGATTATAGGTCATAATAGAATTCCTATAGTTAGTTGGATGCAATCTCAAGCAAGTGAA
AGTTTAACTCATGCTACTGCAGCAGGTGAAATGATAACTCACTTTGGTGAGCATCCATCTTTAAAAATA
GCAGATTTAAACGAAACTTATCAGCATAATATCAATGATATATTAATCGAAAGTCTAGAACATGAGAAA
AAAGCTGTTTCAGCATACTATGAACTTCTAAAACTTGTAAATGGCAAATCAATAATATTAGAAGAATAT
GCAAGAAAACTCATAGTTGAAGAAGAAACGCACATTGGTGAAGTAGAAAAAATGTTAAGAAAACCTGCA
TAA

| MLIIMIRVLN | NGDNNMELQL | ENKQEIIDQL | NKILELEMSG | VVRYTHYSLM | 50  |
| IIGHNRIPIV | SWMQSQASES | LTHATAAGEM | ITHFGEHPSL | KIADLNETYQ | 100 |
| HNINDILIES | LEHEKKAVSA | YYELLKLVNG | KSIILEEYAR | KLIVEEETHI | 150 |
| GEVEKMLRKP | A!         |            |            |            |     |

FIGURE 7-1

DnaK (70-kDa heat shock protein) (SEQ ID NO:5 and 6)

```
ATGGGAAAAATAATAGGTATAGATTTAGGTACTACTAACTCTTGTCTTGCTATTATGGATGGCAAGACT
GCTAAAGTTATTGAGAATGCTGAAGGACATAGAACAACACCTTCAGTTGTGGCATATACTGATAGCGGT
GAAATATTAGTAGGTCAAGCTGCTAAAAGACAAGCTGTAACTAACCCTGATAATACATTCTTTGCTATC
AAGAGACTTATAGGTCGTAAGTACGATGATAAAGCTGTACAAGAAGATATTAAAAAGAAAGTACCTTAT
GCGGTAATTAAAGCTGATAATGGTGATGCTTGGGTTGCTACTAAAGAAGGCAAAAAAATGGCTCCACCA
CAAGTTTCTGCAGAAGTTCTAAGAAAAATGAAAAAAACAGCAGAAGACTATCTAGGTGAACCAGTTACA
GAAGCTGTAATTACAGTGCCAGCATACTTTAACGATAGTCAAAGACAAGCTACAAAAGATGCTGGTAAA
ATAGCAGGTCTTGAAGTTAAAAGAATTATCAACGAGCCTACAGCGGCAGCGCTGGCATATGGTGTAGAC
TCTAAGAAAGGTGAGCAAACTGTAGCGGTGTATGACCTAGGTGGTGGTACATTCGATATCTCAATTATT
GAGATTGCTGATGTTGATGGCGATAACCAAATCGAAGTATTATCAACCAATGGTGATACTTTCTTAGGT
GGTGAAGACTTCGACTTGGCTTTAATGAACTATCTAATTGACGAGTTCAAAAAAGAGCAAGGTATAGAT
CTTCACAATGATAAGCTTGCTTTACAAAGAGTTAGAGAGGCTGCTGAGAAAGCTAAAGTAGAATTATCT
TCAGCACAACAAACTGATGTTAACCTACCTTACATCACAGCAGATGCTACTGGACCTAAGCACTTAAAT
ATCAAAGTAACTAGAGCTAAGTTTGAGTCTTTAGTTTCTGATCTTGTAATGAGATCACTTGAGCCTTGT
AAGAAAGCTCTTGAAGATGCTGGTTTAAGTAAGTCTGATATTACAGAAGTATTACTAGTGGGTGGACAA
ACTCGTATGCCTCTAGTACAAGAGAAAGTAAAAGAGTTTTTTGGTAAAGAGCCACGTAAAGATGTGAAC
CCTGATGAAGCTGTTGCAGTTGGTGCGGCTATTCAAGGTGGTGTATTAGCAGGTGATGTTAAAGATATT
CTTTTATTGGATGTAACACCGCTTTCTCTAGGTATTGAGACTATGGGAGGTGTTATGACTAAGCTTATC
GAGAGAAATACTACGATTCCTACTAAGAAGTCGCAAGTATTCTCAACAGCTGAAGATAACCAGCCTGCG
GTAACTATTCATGTACTTCAAGGTGAGCGTGAAATGGCTTCTGCAAACAAATCTTTAGGTAGATTTGAT
CTGGCAGATATTCCACCAGCGCCACGTGGTATGCCACAAATTGAGGTTACTTTTGATATAGATGCTAAC
GGTATATTAAATGTGTCTGCTAAAGATAAAGCTACTGGTAAAGAGCAAAATATTGTGATTAAGTCTTCA
AGTGGTTTATCTGAAGAGGATATCGAAAAAATGGTACAAGACGCTGAAGCTAATGCAGAAGCAGATAAA
AAGTTCCATGATTTAGTTACTGCTAGAAATACTGCTGATAACTTAATTCATAGCTCAAGAAAAGCAATT
CAAGAACTGGGTGACAAAGTAACAGCAGCAGAAAAAGAAAAAATCGAAGAAGCTTGTAAAGAGCTTGAA
GCAGCAACTAAAGGTGATGATAAGCAAGCGATTGAATCTAAAACTAAGGCTCTAGAAGAAGCATTTGCG
CCAATAGCTCAAAAAGCTTATGCTGAGCAAGCTCAAGCTGCTGTTGCCCAAGGTGGTGCTAAAGCTGAA
GAACCTAAGAAAGAAGAAGATGTTGTTGATGCTGACTTTGAGGATGTTGAAGACGACAAAAAATAA
```

```
MGKIIGIDLG TTNSCLAIMD GKTAKVIENA EGHRTTPSVV AYTDSGEILV        50
GQAAKRQAVT NPDNTFFAIK RLIGRKYDDK AVQEDIKKKV PYAVIKADNG       100
DAWVATKEGK KMAPPQVSAE VLRKMKKTAE DYLGEPVTEA VITVPAYFND       150
SQRQATKDAG KIAGLEVKRI INEPTAAALA YGVDSKKGEQ TVAVYDLGGG       200
TFDISIIEIA DVDGDNQIEV LSTNGDTFLG GEDFDLALMN YLIDEFKKEQ       250
GIDLHNDKLA LQRVREAAEK AKVELSSAQQ TDVNLPYITA DATGPKHLNI       300
KVTRAKFESL VSDLVMRSLE PCKKALEDAG LSKSDITEVL LVGGQTRMPL       350
VQEKVKEFFG KEPRKDVNPD EAVAVGAAIQ GGVLAGDVKD ILLLDVTPLS       400
LGIETMGGVM TKLIERNTTI PTKKSQVFST AEDNQPAVTI HVLQGEREMA       450
SANKSLGRFD LADIPPAPRG MPQIEVTFDI DANGILNVSA KDKATGKEQN       500
IVIKSSSGLS EEDIEKMVQD AEANAEADKK FHDLVTARNT ADNLIHSSRK       550
AIQELGDKVT AAEKEKIEEA CKELEAATKG DDKQAIESKT KALEEAFAPI       600
AQKAYAEQAQ AAVAQGGAKA EEPKKEEDVV DADFEDVEDD KK!
```

FIGURE 7-2 fabD (SEQ ID NO:7 and 8)

ATGTCAAAAACAGCTGTAGTTTTTCCTGGTCAAGGTTCACAAAAACTAGGGATGCTCCAAGATTATTAT
GAAAATTTTGAAACGTTTAGAAATATAGTCGATGAAGCTAAAGAACACCTTGGCTACGACTTATGGAAT
ATTATTCAAAATGATGAAGAAACTCTAAATAAAACAGAGTTTACCCAGCCAGCATTACTTGCAACTAGT
TATGCAATATATGAAGTCTTAAAAGAGCAAAAGCCAGACTTAAAAATAGCATACTTTGCAGGACATAGT
TTAGGTGAATACACTGCCCTACTTGCTGCTGGATGTATTTCATACAAAGATGCTTTACAACTTGTATCT
ACACGTGGCAAATTAATGCAAAATGCTGTTACTGACAAAGAATGTGCTATGAGCGCAATTCTAGGTTTA
TCAAATGAGGATGTAATCAAATCTTGTCAAGAAGCTAGTGATGCTGGAATTGTTGAAGCTGCAAACTTT
AACTCAACAGGACAAGTTGTCATCTCTGGGGAAAAAGCCGCTGTTGAGAAAGCTAATACAATAGCTAAA
GAAAAGGTGCAAAACGCGCGCAGATACTTGCTGTTAGCGTACCTTCACATTGTTCTTTAATGAAGGAT
GCTGCAGATAAATTTGAAGCAGAGTTAAACAAAGTAGAATTTAAAGAGCCTACTACCGCTGTTGTACAA
AACTTTGACGCCAAATCACACGCAAATCCAGCTGAAATAAAAACTGCTGTTATTAAACAACTATACAAG
CCAGTACTTTGGACACAATCTATCGAAGAGCTAGTCAAACTTGGAGTCACAGAAGTTATCGAATGTGGT
CCTAACAAGGTCTTATCTGGACTAATCAAAAGAATAGATAAATCAATAGATATAAAAGATACAAACAGT
ATTGATAGTTTAGAAAATATTTAA

| MSKTAVVFPG | QGSQKLGMLQ | DYYENFETFR | NIVDEAKEHL | GYDLWNIIQN | 50 |
| DEETLNKTEF | TQPALLATSY | AIYEVLKEQK | PDLKIAYFAG | HSLGEYTALL | 100 |
| AAGCISYKDA | LQLVSTRGKL | MQNAVTDKEC | AMSAILGLSN | EDVIKSCQEA | 150 |
| SDAGIVEAAN | FNSTGQVVIS | GEKAAVEKAN | TIAKEKGAKR | AQILAVSVPS | 200 |
| HCSLMKDAAD | KFEAELNKVE | FKEPTTAVVQ | NFDAKSHANP | AEIKTAVIKQ | 250 |
| LYKPVLWTQS | IEELVKLGVT | EVIECGPNKV | LSGLIKRIDK | SIDIKDTNSI | 300 |
| DSLENI! | groEL (SEQ ID NO:9 and 10)

ATGGCTGCAAAACAAGTTTTATTTTCAGATGAAGCTCGTGCAAAAATGCTAGATGGTGTTAACACACTA
GCAAATGCTGTAAAAGTTACTTTAGGTCCAAAAGGTCGTAATGTTGTTTTAGATAAATCATTTGGCACG
CCTACTATCACTAAAGATGGTGTATCTGTTGCTAAAGAAATTGAACTAGAAGATAAGTTTGAGAATATG
GGTGCTCAGATAGTTAAAGAAGTAGCTTCAAAGACAGCGGATGTTGCTGGTGATGGTACTACTACAGCG
ACTGTACTTGCTCAGGCATTATTGACAGAGGGTCTAAAAGCTGTCGCTGCAGGTATGAATCCTATGGAT
CTAAAAAGAGGTATCGACAAAGCAACTGCTAGGTTAGTTGAAGAATTAAAAGCACTTTCTAAACCATGT
TCAGATCCAAAATCAATTGAGCAAGTTGGTACTATCTCTGCTAACTCTGATGCTACTGTAGGTAAGCTT
ATCGCTGACGCAATGGCAAAAGTTGGTAAAGAAGGTGTGATTACAGTTGAAGAAGGCAAAGGCTTTGAA
GATGAGCTTGATGTAGTTGAAGGTATGCAGTTTGATAGAGGTTATCTATCTCCGTATTTTGCAACAAAT
CAAGAGAATATGACTACTGATTTAGAGAATCCATATATTCTAATAGTTGATAAGAAAATCTCTAATATC
CGCGATTTATTACCGATATTAGAAGGTGTTTCTAAATCTGGTAGAGCGTTACTAATAATAGCTGAAGAT
GTAGAAAGTGAAGCTCTAGCTACTTTAGTTGTAAATAATATGCGTGGTGTAGTTAAAGTATGTGCTGTC
AAAGCTCCTGGCTTTGGTGATAGAAGAAAAGCTATGCTAGAAGATATCGCTACTCTAACTGGAGCTACG
TTTGTATCAGAAGACCTAAGCATGAAGTTAGAAGAAACTAACATGGAGCATTTAGGTACGGCTAGTAGA
GTACAAGTAACAAAAGATAATACAACAATTATTGATGGTGCTGGTGAAAAAGAAGCTATCGCTAAACGA
ATAAATGTAATCAAAGCTAATATTGCTGAAGCTAACTCTGATTATGATCGTGAGAAGCTGCAAGAAAGA
TTGGCTAAACTTTCTGGTGGTGTCGCGGTGATAAAAGTTGGTGCTGTTACAGAAGCTGAGATGAAAGAG
AAGAAAGATCGTGTCGATGATGCTTTACATGCTACTCGTGCGGCTGTAGAAGAAGGTATTGTTGCTGGT
GGTGGCGTTGCTTTAATTAGAGCACAAAAAGCATTAGATGGCTTAACAGGTGAAAATGACGATCAAAAC
TATGGTATAGCGCTACTTAGAAAAGCAATAGAAGCTCCTCTAAGACAGATAGTATCAAATGCTGGCGGT
GAGTCTTCTGTAGTTGTTAACCAAGTTAAAGCTAATCAAGGTAACTATGGTTATAATGCTGCAAATGAT
ACTTATGGTGATATGGTTGAGATGGGTATTTTAGATCCTACTAAAGTTACTCGTTCAGCTCTACAACAT
GCTGCTTCAATTGCTGGACTTATGATCACTACAGAGGCGATGATCGGTGAGATCAAAGAAGCTGCTCCT
GCTATGCCTATGGGCGGTGGCATGGGCGGTATGCCTGGCATGATGTAATAG

FIGURE 7-3

```
MAAKQVLFSD EARAKMLDGV NTLANAVKVT LGPKGRNVVL DKSFGTPTIT   50
KDGVSVAKEI ELEDKFENMG AQIVKEVASK TADVAGDGTT TATVLAQALL  100
TEGLKAVAAG MNPMDLKRGI DKATARLVEE LKALSKPCSD PKSIEQVGTI  150
SANSDATVGK LIADAMAKVG KEGVITVEEG KGFEDELDVV EGMQFDRGYL  200
SPYFATNQEN MTTDLENPYI LIVDKKISNI RDLLPILEGV SKSGRALLII  250
AEDVESEALA TLVVNNMRGV VKVCAVKAPG FGDRRKAMLE DIATLTGATF  300
VSEDLSMKLE ETNMEHLGTA SRVQVTKDNT TIIDGAGEKE AIAKRINVIK  350
ANIAEANSDY DREKLQERLA KLSGGVAVIK VGAVTEAEMK EKKDRVDDAL  400
HATRAAVEEG IVAGGGVALI RAQKALDGLT GENDDQNYGI ALLRKAIEAP  450
LRQIVSNAGG ESSVVVNQVK ANQGNYGYNA ANDTYGDMVE MGILDPTKVT  500
RSALQHAASI AGLMITTEAM IGEIKEAAPA MPMGGGMGGM PGMM!!
``` iglC (SEQ ID NO:11 and 12)

```
ATGAGTGAGATGATAACAAGACAACAGGTAACAAGTGGCGAGACCATTCATGTGAGAACTGATCCTACT
GCATGTATAGGATCTCATCCTAATTGTAGATTATTTATTGATTCTTTAACTATAGCTGGGGAGAAACTT
GATAAAAATATCGTTGCTATAGATGGTGGAGAGGATGTCACGAAAGCTGATTCGGCTACAGCTGCTGCT
AGTGTAATACGTTTATCTATAACGCCAGGCTCTATAAATCCAACAATAAGTATTACTCTTGGTGTTCTA
ATTAAATCAAATGTTAGAACTAAAATTGAAGAGAAAGTTTCGAGTATATTACAAGCAAGTGCTACAGAT
ATGAAAATTAAGTTAGGTAATTCTAATAAAAAACAAGAGTATAAAACTGATGAAGCATGGGGTATTATG
ATAGATCTATCTAATTTAGAGTTATATCCAATAAGTGCTAAGGCTTTTAGTATTAGTATAGAGCCAACA
GAACTTATGGGTGTTTCAAAAGATGGAATGAGATATCATATTATATCTATAGATGGTCTTACAACATCT
CAAGGAAGTTTGCCAGTATGTTGCGCAGCTAGCACAGATAAAGGAGTTGCTAAAATAGGATATATTGCA
GCTGCATAGTAA
```

```
MSEMITRQQV TSGETIHVRT DPTACIGSHP NCRLFIDSLT IAGEKLDKNI   50
VAIDGGEDVT KADSATAAAS VIRLSITPGS INPTISITLG VLIKSNVRTK  100
IEEKVSSILQ ASATDMKIKL GNSNKKQEYK TDEAWGIMID LSNLELYPIS  150
AKAFSISIEP TELMGVSKDG MRYHIISIDG LTTSQGSLPV CCAASTDKGV  200
AKIGYIAAA!
``` katG (SEQ ID NO:13 and 14)

```
ATGCTAAAGAAAATTGTAACTGCTTTAGGAATGTCTGGAATGCTACTAGCTTCTAGCAATGCTATCGCA
GAAGATACCACAACGAAAAATGATAATCTTTCACCACAGAGCGTAGATTTATCACCATTGCGCAATTTA
AATAAGCTTGATAGCCCAATGGATAAAGATTATAACTATCATCAAGCTTTCAAAAAACTAGATACTGAA
CAGCTTAAAAAAGATATGCAAGATCTTTTAACCCAGTCACAAGACTGGTGGCCTGCTGATTTTGGCAAT
TATGGTCCTTTCTTTATTAGACTATCGTGGCATGATGCTGGTACATACAGAATATATGATGGCAGAGGA
GGCGCTAATCGTGGACAACAAAGGTTCTCCCCTTTAAATAGCTGGCCAGATAATGTTAATCTTGACAAA
GCAAGGCAACTTTTATGGCCAATCAAACAAAAATATGGTGATGCTGTTTCATGGTCTGATTTGATTGTT
TTAGCTGGTACTGTTTCTTTAGAATCAATGGGAATGAAGCCTATAGGGTTTGCTTTTGGTAGAAGAAGAC
GACTGGCAAGGTGATGATACAAACTGGGGACTATCACCTGAAGAGATAATGTCTAGTAATGTAAGAGAT
GGCAAACTTGCTCCTGCATACGCCGCAACACAAATGGGGCTAATATATGTAAATCCAGAAGGTCCTGAT
GGTAAACCTGATATCAAAGGTGCAGCTAGTGAAATTCGTCAGGCCTTCCGAGCTATGGGGATGACAGAT
AAAGAAACTGTCGCCCTAATTGCAGGCGGTCATACATTTGGTAAAACTCATGGTGCAGTTCCAGAGGAT
AAAGTCAAACAAGCAATTGGACCTGCTCCTGATAAGGCGCCTATTGAGCAGCAAGGTCTAGGCTGGCAC
AATAGTTATGGCACTGGAAATGGTGATGATACTATGGGTAGCGGTCTTGAAGGCTCTTGGACTTCTACT
CCAACTTTTTGGAATCATGATTTCTTACATAACCTTTACAACTTAGACTGGAAGAAAACACTTAGCCCT
GCTGGAGCTCACCAATGGACTCCTACAAATGCTAAGCCAGAAAATATGGTTCCTGATGCTCACAAGCCG
GGTGTAAAACATAAACCTATAATGTTTACAACAGACTTAGCGCTAAAAGAAGATGATGGATTTAATAAA
TATACTCAAGAGTTCTACAATAATCCTGAAGAATTTAAAGAAGAGTTTGCTAAAGCATGGTTTAAATTA
ACACATAGAGATATGGGACCAAAATCTAGATATATAGGTCCTTGGATTCCTGAGCAAAACTTTATTTGG
CAGGATCCTGTTCCAGCAGCAGACTATAAGCAAGTGTCTACACAAGATATTGCCCAACTTGAGCAAGAT
ATTATAAACTCTGGATTAACTAATCAGCAACTTATAAAAACTGCTTGGGATTCAGCTTCTACTTATCGT
```

FIGURE 7-4

```
AAAACCGACTATAGAGGTGGCTCAAATGGTGCAAGGATTGCTTTAGCTCCAGAGAAAGATTGGCAAATG
AATGAACCAGCTAAACTTGAAGTTGTTCTTACTAAGCTTAAAGAGATTCAAACCAACTTTAACAATAGC
AAAACTGATGGTACAAAAGTATCATTGGCTGACTTAATAGTGCTAGGTGGTAATGTGGGTGTTGAGCAA
GCAGCTAAACAAGCTGGTTATAATATACAAATGCCTTTTGTACCAGGTAGAACAGATGCTACTCAAGCT
CAAACTGACATAGAGTCTTTCAACTATCTAAAAACCAAATCTGATGGTTTTATAAACTATACAGATGGT
AGTGTAAGTGCTGATAAATTACCACAGACTTAGTAGAAAAAGCTAGCATGCTTGACTTAAATATCCCA
GAAATGACAGTGTTAGTCGGTGGTATGCGTGCTCTTGATGTCAATTATGATAACTCACAAGAAGGTGTA
TTAACTACTACTCCAGGTCAGCTTAATAATAGCTTCTTTGTGAACTTGCTAGATATGTCTACTCAATGG
AAAAAATCTGATAAAAAGATGGTGAGTATATTGGTATAGATAGAAAAACTGGTAAGCAAAAGTGGACA
GCATCGCCAGTTGATCTAATTTTTGGATCAAACTCAGAGCTTAAAGCAGTAGCTCAAGTTTATGCTGAA
AATGGTAATGAGCAAAAATTTGTAAATGACTTTGCAAAAGCTTGGCATAAAGTTATGATGCTTGGCAGA
TTTGATGTTCAACAATAA
```

```
MLKKIVTALG MSGMLLASSN AIAEDTTTKN DNLSPQSVDL SPLRNLNKLD    50
SPMDKDYNYH QAFKKLDTEQ LKKDMQDLLT QSQDWWPADF GNYGPFFIRL   100
SWHDAGTYRI YDGRGGANRG QQRFSPLNSW PDNVNLDKAR QLLWPIKQKY   150
GDAVSWSDLI VLAGTVSLES MGMKPIGFAF GREDDWQGDD TNWGLSPEEI   200
MSSNVRDGKL APAYAATQMG LIYVNPEGPD GKPDIKGAAS EIRQAFRAMG   250
MTDKETVALI AGGHTFGKTH GAVPEDKVKQ AIGPAPDKAP IEQQGLGWHN   300
SYGTGNGDDT MGSGLEGSWT STPTFWNHDF LHNLYNLDWK KTLSPAGAHQ   350
WTPTNAKPEN MVPDAHKPGV KHKPIMFTTD LALKEDDGFN KYTQEFYNNP   400
EEFKEEFAKA WFKLTHRDMG PKSRYIGPWI PEQNFIWQDP VPAADYKQVS   450
TQDIAQLEQD IINSGLTNQQ LIKTAWDSAS TYRKTDYRGG SNGARIALAP   500
EKDWQMNEPA KLEVVLTKLK EIQTNFNNSK TDGTKVSLAD LIVLGGNVGV   550
EQAAKQAGYN IQMPFVPGRT DATQAQTDIE SFNYLKTKSD GFINYTDGSV   600
SADKLPQTLV EKASMLDLNI PEMTVLVGGM RALDVNYDNS QEGVLTTTPG   650
QLNNSFFVNL LDMSTQWKKS DKKDGEYIGI DRKTGKQKWT ASPVDLIFGS   700
NSELKAVAQV YAENGNEQKF VNDFAKAWHK VMMLGRFDVQ Q!
```

Pld (SEQ ID NO:15 and 16)

```
ATGAGAATTTTATTTACAATTTTAGCTTTTTTTGGATACAGTTATGGGTTAGCACATGGAATTACTAAA
ACAATAGTACACAACTATCCTGAAAACATATCAAAATCATTTCAAATTAGTAACAACAATTATGCTCCT
TTACAAATTAGTAAACTAATCCAGAGTGCAAAGAAAAATATTGATATTGAAGTATTCTACATAGATATA
AAAAAAGACAGTGTTCTAGATAAGATGATAATTCAACCTTTAGCAGCAAAGGCTAATCAAGGAATTAAA
GTTAGAATTTTGGTGGATGACAAATTTTATAGCCAATACAGCAACAACAAAGCTAGCTGTGATTATTTA
AACTCTATTAAGAATATAACTTGTAAACCGACAAAAGAATTTCAAGAAGCTGTAATGCACTCTAAAATG
ATAAGCATTGATGGTAAGTCTTTTTACATTGGTAGTCATAATTTTGATTGGATAACATTTGAACTTAAT
CATGAGCTAGGAGTTATTGTTAAAAATGATAAGATTAATGCTGCTAAACTTGAAAAATCTTTTAATGAT
GATTGGAACTTTACTAATAAAGTAAAAAGCTAACAGATAATAACTTGAATACATACTCACTTCATGAC
CAAGGAAATCAAGCGATTGTGACTGTTACACCTGATATAGATAAAAAAGGTTACCCTAAAAGTAATCTA
AAAACTTTCATATCATTAATTAAATCTGCAAAATCAAGTATAGTAATCCAAGCAATGATTGTATCTGGA
ATAGATCCATACATGAATGATAAAAACTGGGATGAATTTACAAAAGCCTTATCAGACGCTAATAAACGA
AATGTTTATGTAAAAATTATGTTCTCAAATTGGATGTTTACCAAATCTTCGTATAAAGATAGTAATGAT
TGGCTACAAAAACTGATTCATCAATCAAATCAAAATCACTTAAAGATCAAATACACATCATTACCCCAT
ACAAAACAATGTGTACCATTCTCTGAAGTAGATCATGCAAAATATGCTATTTTTGATGGTACCATAGCA
TGGGTTTCTACTTCTAATATACAAAAATCCTACTTCTATGCGGCAAAAAACTATTCATACATTGCTGAC
GATAAAGACCTATCACGGCAACTGACAGATGTTTTTGAGCAGCTTTGGGATAGTAAATATGCTCATACA
TATTCGCAACCTGTTGGTATAATATCAACTCCGTCTTGTACCTAA
```

FIGURE 7-5

MRILFTILAF FGYSYGLAHG ITKTIVHNYP ENISKSFQIS NNNYAPLQIS
KLIQSAKKNI DIEVFYIDIK KDSVLDKMII QPLAAKANQG IKVRILVDDK
FYSQYSNNKA SCDYLNSIKN ITCKPTKEFQ EAVMHSKMIS IDGKSFYIGS
HNFDWITFEL NHELGVIVKN DKINAAKLEK SFNDDWNFTN KSKKLTDNNL
NTYSLHDQGN QAIVTVTPDI DKKGYPKSNL KTFISLIKSA KSSIVIQAMI
VSGIDPYMND KNWDEFTKAL SDANKRNVYV KIMFSNWMFT KSSYKDSNDW
LQKLIHQSNQ NHLKIKYTSL PHTKQCVPFS EVDHAKYAIF DGTIAWVSTS
NIQKSYFYAA KNYSYIADDK DLSRQLTDVF EQLWDSKYAH TYSQPVGIIS
TPSCT!

sodB (SEQ ID NO:17 and 18)

ATGAAATTTGAATTACCAAAACTACCTTACGCTGTTGATGCATTAGAGTCAACAATATCAAAAGAAACA
ATAGAGTATCACTATGGTAAACATCATCAAACATATGTAACTAATCTAAATAATTTAGTTGAGGGTACA
GAGCACGATGGCAGAAACCTAGAAGAAATCGTAAAAACTTCTAATGGCGGAATATTTAATAACGCTGCT
CAAGTTTTTAATCATACTTTTTACTGGAATTGTTTAACTCCAAACAAAACAGAAGCTTCAAGTCAGTTA
AAAGCAGCATTGATCGAGACATTTGGTTCTGTAGAAAATTTTAAAGAACAATTCTCTAAGGCAGCTATT
GCAACATTTGGTTCTGGTTGGGCTTGGTTAGTAAAAAATACTGAAGGTAAACTTGAAATAGTAACTACA
AGTAACGCTGGTTGCCCATTAACAGAGAACAAAAAGCCATTGCTAACTTTTGATGTTTGGGAGCACGCA
TACTATATTGATTATCGTAATGCTAGACCTAAATATGTTGAAGCATTATGGGATATCGTAAACTGGCAA
TTTGTTTCTGAGCAATTCGCTGATTAG

MKFELPKLPY AVDALESTIS KETIEYHYGK HHQTYVTNLN NLVEGTEHDG RNLEEIVKTS
NGGIFNNAAQ VFNHTFYWNC LTPNKTEASS QLKAALIETF GSVENFKEQF SKAAIATFGS
GWAWLVKNTE GKLEIVTTSN AGCPLTENKK PLLTFDVWEH AYYIDYRNAR PKYVEALWDI
VNWQFVSEQF AD!

Tul4 (SEQ ID No: 19 and 20)

ATGAAAAAAATAATTGAGCTTAGTCTTTTATCTTTATCAATCGCAGGTTTAGCGAGCTGTTCTACTCTA
GGGTTAGGTGGCTCTGATGATGCAAAAGCTTCAGCTAAAGATACTGCTGCTGCTCAGACAGCTACTACT
GAGCAAGCTGCTGCTGTATCTAAGCCAACTGCAAAAGTAAGTTTAAATAAACTTGGTCAGGATAAAATA
AAAGCAACTGTATATACAACATACAATAATAACCCACAAGGAAGTGTAAGATTACAATGGCAGGCTCCA
GAAGGTTCTAAGTGCCATGATACAAGCTTCCCAATTACTAAGTATGCTGAGAAGAACGATAAAACTTGG
GCAACTGTAACAGTTAAGCAAGGTAATAACTTCTGTAGCGGTAAGTGGACAGCTAATGTAGTTTATGAC
AAAGAAGTAATCGCTTCTGATTCAATAAATATTTAA

MKKIIELSLL SLSIAGLASC STLGLGGSDD AKASAKDTAA AQTATTEQAA AVSKPTAKVS
lnklgqdkik atvyttynnn pqgsvrlqwq apegskchdt sfpitkyaek ndktwatvtv
KQGNNFCSGK WTANVVYDKE VIASDSINI!

FIGURE 7-6

SEQUENCE LISTING

<160> NUMBER OF SEQ ID NOS: 30

<210> SEQ ID NO 1
<211> LENGTH: 1545
<212> TYPE: DNA
<213> ORGANISM: Francisella tularensis
<220> FEATURE:
<221> NAME/KEY: CDS
<222> LOCATION: (1)..(1545)

<400> SEQUENCE: 1

```
atg aag ctc aat aaa att act tta gga att tta agt cta agt atc gca      48
Met Lys Leu Asn Lys Ile Thr Leu Gly Ile Leu Ser Leu Ser Ile Ala
1               5                   10                  15 aca acg act ttt gcc aca gat gtg aat aat agc aaa cca aat gat tat      96
Thr Thr Thr Phe Ala Thr Asp Val Asn Asn Ser Lys Pro Asn Asp Tyr
                20                  25                  30 gga act ctt gta aaa ata aaa caa aaa tta ttt aat aat gcg aat act     144
Gly Thr Leu Val Lys Ile Lys Gln Lys Leu Phe Asn Asn Ala Asn Thr
            35                  40                  45 cta aaa act aca act cca ata aag cac gta gta ata ata ttc caa gag     192
Leu Lys Thr Thr Thr Pro Ile Lys His Val Val Ile Ile Phe Gln Glu
        50                  55                  60 aat aac tct ttt gat aga tac ttt gga atg tac ccc aat gcc aaa aac     240
Asn Asn Ser Phe Asp Arg Tyr Phe Gly Met Tyr Pro Asn Ala Lys Asn
65                  70                  75                  80 cca gag ggt gag cca aaa ttt gta gcc aaa gaa aat act cca aat gtt     288
Pro Glu Gly Glu Pro Lys Phe Val Ala Lys Glu Asn Thr Pro Asn Val
                85                  90                  95 aat ggt ctg aca aaa caa tta tta gag aat aat cca aat aca aaa aat     336
Asn Gly Leu Thr Lys Gln Leu Leu Glu Asn Asn Pro Asn Thr Lys Asn
            100                 105                 110 cct tat cgt tta gat aga aat ttc caa cct tgc tca caa aat cat gag     384
Pro Tyr Arg Leu Asp Arg Asn Phe Gln Pro Cys Ser Gln Asn His Glu
        115                 120                 125 tac cat caa gaa att tct tct ttt aat ggt gga tta atg aac aaa ttt     432
Tyr His Gln Glu Ile Ser Ser Phe Asn Gly Gly Leu Met Asn Lys Phe
    130                 135                 140 gtt gaa cat ggt ggt cat gat aat gac acc tat aaa caa aac tgt gat     480
Val Glu His Gly Gly His Asp Asn Asp Thr Tyr Lys Gln Asn Cys Asp
145                 150                 155                 160 ggt caa gtc atg gga tat tat gat ggt aat act gtc aca gca tta tgg     528
Gly Gln Val Met Gly Tyr Tyr Asp Gly Asn Thr Val Thr Ala Leu Trp
                165                 170                 175 aat tac gca caa aat ttc gct cta aat gat aat acg ttt ggt aca act     576
Asn Tyr Ala Gln Asn Phe Ala Leu Asn Asp Asn Thr Phe Gly Thr Thr
```

```
                  180                 185                 190
ttt ggt cca tca aca cct ggt gcc ctt aac cta gtg gct ggt gca aat    624
Phe Gly Pro Ser Thr Pro Gly Ala Leu Asn Leu Val Ala Gly Ala Asn
            195                 200                 205 ggt cca gca atg agt cca agt ggt aat tta gaa aat att gaa aac agc    672
Gly Pro Ala Met Ser Pro Ser Gly Asn Leu Glu Asn Ile Glu Asn Ser
210                 215                 220 tat atc att gat gat cct aac cca tac tac gat gat tgc tct tat ggt    720
Tyr Ile Ile Asp Asp Pro Asn Pro Tyr Tyr Asp Asp Cys Ser Tyr Gly
225                 230                 235                 240 aca agt aaa tct ggc gat aca aat aca gct gta gca aaa att act gat    768
Thr Ser Lys Ser Gly Asp Thr Asn Thr Ala Val Ala Lys Ile Thr Asp
            245                 250                 255 ggt tat aat att gga cac tat cta act caa aaa ggt att act tgg ggt    816
Gly Tyr Asn Ile Gly His Tyr Leu Thr Gln Lys Gly Ile Thr Trp Gly
        260                 265                 270 tgg ttc caa gga gga ttc aaa cca aca agc tac tct ggt aaa aca gca    864
Trp Phe Gln Gly Gly Phe Lys Pro Thr Ser Tyr Ser Gly Lys Thr Ala
    275                 280                 285 ata tgt gat gct atg agc act aat aag ttc ggt ata aaa tca aga gac    912
Ile Cys Asp Ala Met Ser Thr Asn Lys Phe Gly Ile Lys Ser Arg Asp
290                 295                 300 tat ata cct cat cat gag cct ttt aac tat tgg aaa gag aca tca aac    960
Tyr Ile Pro His His Glu Pro Phe Asn Tyr Trp Lys Glu Thr Ser Asn
305                 310                 315                 320 cct cat cat cta gca cca agt gat gat aag tat ata ggt agt aat gac   1008
Pro His His Leu Ala Pro Ser Asp Asp Lys Tyr Ile Gly Ser Asn Asp
            325                 330                 335 caa gct aac cat cag tac gac ata agt gaa ttt tgg aag gct ctt gat   1056
Gln Ala Asn His Gln Tyr Asp Ile Ser Glu Phe Trp Lys Ala Leu Asp
        340                 345                 350 caa aac acc atg cct gcg gta agt tac tta aaa gct cct gga tat caa   1104
Gln Asn Thr Met Pro Ala Val Ser Tyr Leu Lys Ala Pro Gly Tyr Gln
    355                 360                 365 gat ggt cat gga ggc tac tca aac cct cta gat gaa caa gaa tgg cta   1152
Asp Gly His Gly Gly Tyr Ser Asn Pro Leu Asp Glu Gln Glu Trp Leu
370                 375                 380 gtc aat act att aat aga atc aaa caa tca aaa gac tgg gat agc aca   1200
Val Asn Thr Ile Asn Arg Ile Lys Gln Ser Lys Asp Trp Asp Ser Thr
385                 390                 395                 400 gca att ata att att tat gat gac tct gat ggt gac tat gac cat gtc   1248
Ala Ile Ile Ile Ile Tyr Asp Asp Ser Asp Gly Asp Tyr Asp His Val
            405                 410                 415 tac agt cca aaa tca cag ttt agc gat att aaa gga aga caa ggc tat   1296
Tyr Ser Pro Lys Ser Gln Phe Ser Asp Ile Lys Gly Arg Gln Gly Tyr
        420                 425                 430 gga cca aga tta cca atg ctt gtt att tct cct tat act aaa gca aac   1344
Gly Pro Arg Leu Pro Met Leu Val Ile Ser Pro Tyr Thr Lys Ala Asn
    435                 440                 445 tat att gat cat tca tta ctt aat caa gca tct gta ctt aag ttt ata   1392
Tyr Ile Asp His Ser Leu Leu Asn Gln Ala Ser Val Leu Lys Phe Ile
450                 455                 460 gag tat aac tgg ggc att ggc tca gtt agt aag tat agt aat gat aaa   1440
Glu Tyr Asn Trp Gly Ile Gly Ser Val Ser Lys Tyr Ser Asn Asp Lys
465                 470                 475                 480 tac tca aac aat atc tta aac atg ttt gat ttt aat aaa aaa caa aaa   1488
Tyr Ser Asn Asn Ile Leu Asn Met Phe Asp Phe Asn Lys Lys Gln Lys
            485                 490                 495 aca cca aaa ctg att tta gac cct aag aca gga tta gta gtg gat aaa   1536
Thr Pro Lys Leu Ile Leu Asp Pro Lys Thr Gly Leu Val Val Asp Lys
```

```
                       500                 505                 510
tta aac taa                                                                1545
Leu Asn <210> SEQ ID NO 2
<211> LENGTH: 514
<212> TYPE: PRT
<213> ORGANISM: Francisella tularensis

<400> SEQUENCE: 2

Met Lys Leu Asn Lys Ile Thr Leu Gly Ile Leu Ser Leu Ser Ile Ala
1               5                   10                  15

Thr Thr Thr Phe Ala Thr Asp Val Asn Asn Ser Lys Pro Asn Asp Tyr
                20                  25                  30

Gly Thr Leu Val Lys Ile Lys Gln Lys Leu Phe Asn Asn Ala Asn Thr
            35                  40                  45

Leu Lys Thr Thr Thr Pro Ile Lys His Val Val Ile Ile Phe Gln Glu
    50                  55                  60

Asn Asn Ser Phe Asp Arg Tyr Phe Gly Met Tyr Pro Asn Ala Lys Asn
65                  70                  75                  80

Pro Glu Gly Glu Pro Lys Phe Val Ala Lys Glu Asn Thr Pro Asn Val
                85                  90                  95

Asn Gly Leu Thr Lys Gln Leu Leu Glu Asn Asn Pro Asn Thr Lys Asn
            100                 105                 110

Pro Tyr Arg Leu Asp Arg Asn Phe Gln Pro Cys Ser Gln Asn His Glu
        115                 120                 125

Tyr His Gln Glu Ile Ser Ser Phe Asn Gly Gly Leu Met Asn Lys Phe
    130                 135                 140

Val Glu His Gly Gly His Asp Asn Asp Thr Tyr Lys Asn Asn Cys Asp
145                 150                 155                 160

Gly Gln Val Met Gly Tyr Tyr Asp Gly Asn Thr Val Thr Ala Leu Trp
                165                 170                 175

Asn Tyr Ala Gln Asn Phe Ala Leu Asn Asp Asn Thr Phe Gly Thr Thr
            180                 185                 190

Phe Gly Pro Ser Thr Pro Gly Ala Leu Asn Leu Val Ala Gly Ala Asn
        195                 200                 205

Gly Pro Ala Met Ser Pro Ser Gly Asn Leu Glu Asn Ile Glu Asn Ser
    210                 215                 220

Tyr Ile Ile Asp Asp Pro Asn Pro Tyr Tyr Asp Asp Cys Ser Tyr Gly
225                 230                 235                 240

Thr Ser Lys Ser Gly Asp Thr Asn Thr Ala Val Ala Lys Ile Thr Asp
                245                 250                 255

Gly Tyr Asn Ile Gly His Tyr Leu Thr Gln Lys Gly Ile Thr Trp Gly
            260                 265                 270

Trp Phe Gln Gly Gly Phe Lys Pro Thr Ser Tyr Ser Gly Lys Thr Ala
        275                 280                 285

Ile Cys Asp Ala Met Ser Thr Asn Lys Phe Gly Ile Lys Ser Arg Asp
    290                 295                 300

Tyr Ile Pro His His Glu Pro Phe Asn Tyr Trp Lys Glu Thr Ser Asn
305                 310                 315                 320

Pro His His Leu Ala Pro Ser Asp Lys Tyr Ile Gly Ser Asn Asp
                325                 330                 335

Gln Ala Asn His Gln Tyr Asp Ile Ser Glu Phe Trp Lys Ala Leu Asp
            340                 345                 350

Gln Asn Thr Met Pro Ala Val Ser Tyr Leu Lys Ala Pro Gly Tyr Gln
```

-continued

```
                    355                 360                 365
Asp Gly His Gly Gly Tyr Ser Asn Pro Leu Asp Glu Gln Glu Trp Leu
370                 375                 380

Val Asn Thr Ile Asn Arg Ile Lys Gln Ser Lys Asp Trp Asp Ser Thr
385                 390                 395                 400

Ala Ile Ile Ile Ile Tyr Asp Asp Ser Asp Gly Asp Tyr Asp His Val
                405                 410                 415

Tyr Ser Pro Lys Ser Gln Phe Ser Asp Ile Lys Gly Arg Gln Gly Tyr
                420                 425                 430

Gly Pro Arg Leu Pro Met Leu Val Ile Ser Pro Tyr Thr Lys Ala Asn
                435                 440                 445

Tyr Ile Asp His Ser Leu Leu Asn Gln Ala Ser Val Leu Lys Phe Ile
                450                 455                 460

Glu Tyr Asn Trp Gly Ile Gly Ser Val Ser Lys Tyr Ser Asn Asp Lys
465                 470                 475                 480

Tyr Ser Asn Asn Ile Leu Asn Met Phe Asp Phe Asn Lys Lys Gln Lys
                485                 490                 495

Thr Pro Lys Leu Ile Leu Asp Pro Lys Thr Gly Leu Val Val Asp Lys
                500                 505                 510

Leu Asn
```

<210> SEQ ID NO 3
<211> LENGTH: 486
<212> TYPE: DNA
<213> ORGANISM: Francisella tularensis
<220> FEATURE:
<221> NAME/KEY: CDS
<222> LOCATION: (1)..(486)

<400> SEQUENCE: 3

```
atg ttg att ata atg att aga gtt tta aat aat gga gat aac aat atg       48
Met Leu Ile Ile Met Ile Arg Val Leu Asn Asn Gly Asp Asn Asn Met
1               5                   10                  15 gaa ctt caa tta gaa aat aaa caa gaa att att gat caa tta aat aaa       96
Glu Leu Gln Leu Glu Asn Lys Gln Glu Ile Ile Asp Gln Leu Asn Lys
            20                  25                  30 atc tta gaa ctc gaa atg tct gga gtt gtg cgt tat act cat tat tct      144
Ile Leu Glu Leu Glu Met Ser Gly Val Val Arg Tyr Thr His Tyr Ser
        35                  40                  45 tta atg att ata ggt cat aat aga att cct ata gtt agt tgg atg caa      192
Leu Met Ile Ile Gly His Asn Arg Ile Pro Ile Val Ser Trp Met Gln
    50                  55                  60 tct caa gca agt gaa agt tta act cat gct act gca gca ggt gaa atg      240
Ser Gln Ala Ser Glu Ser Leu Thr His Ala Thr Ala Ala Gly Glu Met
65                  70                  75                  80 ata act cac ttt ggt gag cat cca tct tta aaa ata gca gat tta aac      288
Ile Thr His Phe Gly Glu His Pro Ser Leu Lys Ile Ala Asp Leu Asn
                85                  90                  95 gaa act tat cag cat aat atc aat gat ata tta atc gaa agt cta gaa      336
Glu Thr Tyr Gln His Asn Ile Asn Asp Ile Leu Ile Glu Ser Leu Glu
            100                 105                 110 cat gag aaa aaa gct gtt tca gca tac tat gaa ctt cta aaa ctt gta      384
His Glu Lys Lys Ala Val Ser Ala Tyr Tyr Glu Leu Leu Lys Leu Val
        115                 120                 125 aat ggc aaa tca ata ata tta gaa gaa tat gca aga aaa ctc ata gtt      432
Asn Gly Lys Ser Ile Ile Leu Glu Glu Tyr Ala Arg Lys Leu Ile Val
    130                 135                 140 gaa gaa gaa acg cac att ggt gaa gta gaa aaa atg tta aga aaa cct      480
Glu Glu Glu Thr His Ile Gly Glu Val Glu Lys Met Leu Arg Lys Pro
```

```
                   145                 150                 155                 160
gca taa                                                                                486
Ala
```

<210> SEQ ID NO 4
<211> LENGTH: 161
<212> TYPE: PRT
<213> ORGANISM: Francisella tularensis

<400> SEQUENCE: 4

```
Met Leu Ile Ile Met Ile Arg Val Leu Asn Asn Gly Asp Asn Asn Met
1               5                   10                  15

Glu Leu Gln Leu Glu Asn Lys Gln Glu Ile Ile Asp Gln Leu Asn Lys
            20                  25                  30

Ile Leu Glu Leu Glu Met Ser Gly Val Val Arg Tyr Thr His Tyr Ser
        35                  40                  45

Leu Met Ile Ile Gly His Asn Arg Ile Pro Ile Val Ser Trp Met Gln
50                  55                  60

Ser Gln Ala Ser Glu Ser Leu Thr His Ala Thr Ala Ala Gly Glu Met
65                  70                  75                  80

Ile Thr His Phe Gly Glu His Pro Ser Leu Lys Ile Ala Asp Leu Asn
                85                  90                  95

Glu Thr Tyr Gln His Asn Ile Asn Asp Ile Leu Ile Glu Ser Leu Glu
            100                 105                 110

His Glu Lys Lys Ala Val Ser Ala Tyr Tyr Glu Leu Leu Lys Leu Val
        115                 120                 125

Asn Gly Lys Ser Ile Ile Leu Glu Glu Tyr Ala Arg Lys Leu Ile Val
130                 135                 140

Glu Glu Glu Thr His Ile Gly Glu Val Gly Lys Met Leu Arg Lys Pro
145                 150                 155                 160

Ala
```

<210> SEQ ID NO 5
<211> LENGTH: 1929
<212> TYPE: DNA
<213> ORGANISM: Francisella tularensis
<220> FEATURE:
<221> NAME/KEY: CDS
<222> LOCATION: (1)..(1929)

<400> SEQUENCE: 5

```
atg gga aaa ata ata ggt ata gat tta ggt act act aac tct tgt ctt        48
Met Gly Lys Ile Ile Gly Ile Asp Leu Gly Thr Thr Asn Ser Cys Leu
1               5                   10                  15 gct att atg gat ggc aag act gct aaa gtt att gag aat gct gaa gga        96
Ala Ile Met Asp Gly Lys Thr Ala Lys Val Ile Glu Asn Ala Glu Gly
            20                  25                  30 cat aga aca aca cct tca gtt gtg gca tat act gat agc ggt gaa ata       144
His Arg Thr Thr Pro Ser Val Val Ala Tyr Thr Asp Ser Gly Glu Ile
        35                  40                  45 tta gta ggt caa gct gct aaa aga caa gct gta act aac cct gat aat       192
Leu Val Gly Gln Ala Ala Lys Arg Gln Ala Val Thr Asn Pro Asp Asn
50                  55                  60 aca ttc ttt gct atc aag aga ctt ata ggt cgt aag tac gat gat aaa       240
Thr Phe Phe Ala Ile Lys Arg Leu Ile Gly Arg Lys Tyr Asp Asp Lys
65                  70                  75                  80 gct gta caa gaa gat att aaa aag aaa gta cct tat gcg gta att aaa       288
Ala Val Gln Glu Asp Ile Lys Lys Lys Val Pro Tyr Ala Val Ile Lys
                85                  90                  95
```

```
gct gat aat ggt gat gct tgg gtt gct act aaa gaa ggc aaa aaa atg      336
Ala Asp Asn Gly Asp Ala Trp Val Ala Thr Lys Glu Gly Lys Lys Met
            100                 105                 110 gct cca cca caa gtt tct gca gaa gtt cta aga aaa atg aaa aaa aca      384
Ala Pro Pro Gln Val Ser Ala Glu Val Leu Arg Lys Met Lys Lys Thr
        115                 120                 125 gca gaa gac tat cta ggt gaa cca gtt aca gaa gct gta att aca gtg      432
Ala Glu Asp Tyr Leu Gly Glu Pro Val Thr Glu Ala Val Ile Thr Val
    130                 135                 140 cca gca tac ttt aac gat agt caa aga caa gct aca aaa gat gct ggt      480
Pro Ala Tyr Phe Asn Asp Ser Gln Arg Gln Ala Thr Lys Asp Ala Gly
145                 150                 155                 160 aaa ata gca ggt ctt gaa gtt aaa aga att atc aac gag cct aca gcg      528
Lys Ile Ala Gly Leu Glu Val Lys Arg Ile Ile Asn Glu Pro Thr Ala
                165                 170                 175 gca gcg ctg gca tat ggt gta gac tct aag aaa ggt gag caa act gta      576
Ala Ala Leu Ala Tyr Gly Val Asp Ser Lys Lys Gly Glu Gln Thr Val
            180                 185                 190 gcg gtg tat gac cta ggt ggt ggt aca ttc gat atc tca att att gag      624
Ala Val Tyr Asp Leu Gly Gly Gly Thr Phe Asp Ile Ser Ile Ile Glu
        195                 200                 205 att gct gat gtt gat ggc gat aac caa atc gaa gta tta tca acc aat      672
Ile Ala Asp Val Asp Gly Asp Asn Gln Ile Glu Val Leu Ser Thr Asn
    210                 215                 220 ggt gat act ttc tta ggt ggt gaa gac ttc gac ttg gct tta atg aac      720
Gly Asp Thr Phe Leu Gly Gly Glu Asp Phe Asp Leu Ala Leu Met Asn
225                 230                 235                 240 tat cta att gac gag ttc aaa aaa gag caa ggt ata gat ctt cac aat      768
Tyr Leu Ile Asp Glu Phe Lys Lys Glu Gln Gly Ile Asp Leu His Asn
                245                 250                 255 gat aag ctt gct tta caa aga gtt aga gag gct gct gag aaa gct aaa      816
Asp Lys Leu Ala Leu Gln Arg Val Arg Glu Ala Ala Glu Lys Ala Lys
            260                 265                 270 gta gaa tta tct tca gca caa caa act gat gtt aac cta cct tac atc      864
Val Glu Leu Ser Ser Ala Gln Gln Thr Asp Val Asn Leu Pro Tyr Ile
        275                 280                 285 aca gca gat gct act gga cct aag cac tta aat atc aaa gta act aga      912
Thr Ala Asp Ala Thr Gly Pro Lys His Leu Asn Ile Lys Val Thr Arg
    290                 295                 300 gct aag ttt gag tct tta gtt tct gat ctt gta atg aga tca ctt gag      960
Ala Lys Phe Glu Ser Leu Val Ser Asp Leu Val Met Arg Ser Leu Glu
305                 310                 315                 320 cct tgt aag aaa gct ctt gaa gat gct ggt tta agt aag tct gat att     1008
Pro Cys Lys Lys Ala Leu Glu Asp Ala Gly Leu Ser Lys Ser Asp Ile
                325                 330                 335 aca gaa gta tta cta gtg ggt gga caa act cgt atg cct cta gta caa     1056
Thr Glu Val Leu Leu Val Gly Gly Gln Thr Arg Met Pro Leu Val Gln
            340                 345                 350 gag aaa gta aaa gag ttt ttt ggt aaa gag cca cgt aaa gat gtg aac     1104
Glu Lys Val Lys Glu Phe Phe Gly Lys Glu Pro Arg Lys Asp Val Asn
        355                 360                 365 cct gat gaa gct gtt gca gtt ggt gcg gct att caa ggt ggt gta tta     1152
Pro Asp Glu Ala Val Ala Val Gly Ala Ala Ile Gln Gly Gly Val Leu
    370                 375                 380 gca ggt gat gtt aaa gat att ctt tta ttg gat gta aca ccg ctt tct     1200
Ala Gly Asp Val Lys Asp Ile Leu Leu Leu Asp Val Thr Pro Leu Ser
385                 390                 395                 400 cta ggt att gag act atg gga ggt gtt atg act aag ctt atc gag aga     1248
Leu Gly Ile Glu Thr Met Gly Gly Val Met Thr Lys Leu Ile Glu Arg
                405                 410                 415
```

```
aat act acg att cct act aag aag tcg caa gta ttc tca aca gct gaa    1296
Asn Thr Thr Ile Pro Thr Lys Lys Ser Gln Val Phe Ser Thr Ala Glu
            420                 425                 430 gat aac cag cct gcg gta act att cat gta ctt caa ggt gag cgt gaa    1344
Asp Asn Gln Pro Ala Val Thr Ile His Val Leu Gln Gly Glu Arg Glu
        435                 440                 445 atg gct tct gca aac aaa tct tta ggt aga ttt gat ctg gca gat att    1392
Met Ala Ser Ala Asn Lys Ser Leu Gly Arg Phe Asp Leu Ala Asp Ile
    450                 455                 460 cca cca gcg cca cgt ggt atg cca caa att gag gtt act ttt gat ata    1440
Pro Pro Ala Pro Arg Gly Met Pro Gln Ile Glu Val Thr Phe Asp Ile
465                 470                 475                 480 gat gct aac ggt ata tta aat gtg tct gct aaa gat aaa gct act ggt    1488
Asp Ala Asn Gly Ile Leu Asn Val Ser Ala Lys Asp Lys Ala Thr Gly
                485                 490                 495 aaa gag caa aat att gtg att aag tct tca agt ggt tta tct gaa gag    1536
Lys Glu Gln Asn Ile Val Ile Lys Ser Ser Ser Gly Leu Ser Glu Glu
            500                 505                 510 gat atc gaa aaa atg gta caa gac gct gaa gct aat gca gaa gca gat    1584
Asp Ile Glu Lys Met Val Gln Asp Ala Glu Ala Asn Ala Glu Ala Asp
        515                 520                 525 aaa aag ttc cat gat tta gtt act gct aga aat act gct gat aac tta    1632
Lys Lys Phe His Asp Leu Val Thr Ala Arg Asn Thr Ala Asp Asn Leu
    530                 535                 540 att cat agc tca aga aaa gca att caa gaa ctg ggt gac aaa gta aca    1680
Ile His Ser Ser Arg Lys Ala Ile Gln Glu Leu Gly Asp Lys Val Thr
545                 550                 555                 560 gca gca gaa aaa gaa aaa atc gaa gaa gct tgt aaa gag ctt gaa gca    1728
Ala Ala Glu Lys Glu Lys Ile Glu Glu Ala Cys Lys Glu Leu Glu Ala
                565                 570                 575 gca act aaa ggt gat gat aag caa gcg att gaa tct aaa act aag gct    1776
Ala Thr Lys Gly Asp Asp Lys Gln Ala Ile Glu Ser Lys Thr Lys Ala
            580                 585                 590 cta gaa gaa gca ttt gcg cca ata gct caa aaa gct tat gct gag caa    1824
Leu Glu Glu Ala Phe Ala Pro Ile Ala Gln Lys Ala Tyr Ala Glu Gln
        595                 600                 605 gct caa gct gct gtt gcc caa ggt ggt gct aaa gct gaa gaa cct aag    1872
Ala Gln Ala Ala Val Ala Gln Gly Gly Ala Lys Ala Glu Glu Pro Lys
    610                 615                 620 aaa gaa gaa gat gtt gtt gat gct gac ttt gag gat gtt gaa gac gac    1920
Lys Glu Glu Asp Val Val Asp Ala Asp Phe Glu Asp Val Glu Asp Asp
625                 630                 635                 640 aaa aaa taa                                                        1929
Lys Lys

<210> SEQ ID NO 6
<211> LENGTH: 642
<212> TYPE: PRT
<213> ORGANISM: Francisella tularensis

<400> SEQUENCE: 6

Met Gly Lys Ile Ile Gly Ile Asp Leu Gly Thr Thr Asn Ser Cys Leu
1               5                   10                  15

Ala Ile Met Asp Gly Lys Thr Ala Lys Val Ile Glu Asn Ala Glu Gly
            20                  25                  30

His Arg Thr Thr Pro Ser Val Val Ala Tyr Thr Asp Ser Gly Glu Ile
        35                  40                  45

Leu Val Gly Gln Ala Ala Lys Arg Gln Ala Val Thr Asn Pro Asp Asn
    50                  55                  60

Thr Phe Phe Ala Ile Lys Arg Leu Ile Gly Arg Lys Tyr Asp Asp Lys
```

```
                65                  70                  75                  80
Ala Val Gln Glu Asp Ile Lys Lys Val Pro Tyr Ala Val Ile Lys
                    85                  90                  95
Ala Asp Asn Gly Asp Ala Trp Val Ala Thr Lys Glu Gly Lys Lys Met
                    100                 105                 110
Ala Pro Pro Gln Val Ser Ala Glu Val Leu Arg Lys Met Lys Lys Thr
                    115                 120                 125
Ala Glu Asp Tyr Leu Gly Glu Pro Val Thr Glu Ala Val Ile Thr Val
                    130                 135                 140
Pro Ala Tyr Phe Asn Asp Ser Gln Arg Gln Ala Thr Lys Asp Ala Gly
145                 150                 155                 160
Lys Ile Ala Gly Leu Glu Val Lys Arg Ile Ile Asn Glu Pro Thr Ala
                    165                 170                 175
Ala Ala Leu Ala Tyr Gly Val Asp Ser Lys Lys Gly Glu Gln Thr Val
                    180                 185                 190
Ala Val Tyr Asp Leu Gly Gly Gly Thr Phe Asp Ile Ser Ile Ile Glu
                    195                 200                 205
Ile Ala Asp Val Asp Gly Asp Asn Gln Ile Glu Val Leu Ser Thr Asn
210                 215                 220
Gly Asp Thr Phe Leu Gly Gly Glu Asp Phe Asp Leu Ala Leu Met Asn
225                 230                 235                 240
Tyr Leu Ile Asp Glu Phe Lys Lys Glu Gln Gly Ile Asp Leu His Asn
                    245                 250                 255
Asp Lys Leu Ala Leu Gln Arg Val Arg Glu Ala Ala Glu Lys Ala Lys
                    260                 265                 270
Val Glu Leu Ser Ser Ala Gln Gln Thr Asp Val Asn Leu Pro Tyr Ile
                    275                 280                 285
Thr Ala Asp Ala Thr Gly Pro Lys His Leu Asn Ile Lys Val Thr Arg
                    290                 295                 300
Ala Lys Phe Glu Ser Leu Val Ser Asp Leu Val Met Arg Ser Leu Glu
305                 310                 315                 320
Pro Cys Lys Lys Ala Leu Glu Asp Ala Gly Leu Ser Lys Ser Asp Ile
                    325                 330                 335
Thr Glu Val Leu Leu Val Gly Gly Gln Thr Arg Met Pro Leu Val Gln
                    340                 345                 350
Glu Lys Val Lys Glu Phe Phe Gly Lys Glu Pro Arg Lys Asp Val Asn
                    355                 360                 365
Pro Asp Glu Ala Val Ala Val Gly Ala Ala Ile Gln Gly Gly Val Leu
                    370                 375                 380
Ala Gly Asp Val Lys Asp Ile Leu Leu Leu Asp Val Thr Pro Leu Ser
385                 390                 395                 400
Leu Gly Ile Glu Thr Met Gly Gly Val Met Thr Lys Leu Ile Glu Arg
                    405                 410                 415
Asn Thr Thr Ile Pro Thr Lys Lys Ser Gln Val Phe Ser Thr Ala Glu
                    420                 425                 430
Asp Asn Gln Pro Ala Val Thr Ile His Val Leu Gln Gly Glu Arg Glu
                    435                 440                 445
Met Ala Ser Ala Asn Lys Ser Leu Gly Arg Phe Asp Leu Ala Asp Ile
                    450                 455                 460
Pro Pro Ala Pro Arg Gly Met Pro Gln Ile Glu Val Thr Phe Asp Ile
465                 470                 475                 480
Asp Ala Asn Gly Ile Leu Asn Val Ser Ala Lys Asp Lys Ala Thr Gly
                    485                 490                 495
```

-continued

```
Lys Glu Gln Asn Ile Val Ile Lys Ser Ser Gly Leu Ser Glu Glu
                500                 505                 510

Asp Ile Glu Lys Met Val Gln Asp Ala Glu Ala Asn Ala Glu Ala Asp
            515                 520                 525

Lys Lys Phe His Asp Leu Val Thr Ala Arg Asn Thr Ala Asp Asn Leu
        530                 535                 540

Ile His Ser Ser Arg Lys Ala Ile Gln Glu Leu Gly Asp Lys Val Thr
545                 550                 555                 560

Ala Ala Glu Lys Glu Lys Ile Glu Glu Ala Cys Lys Glu Leu Glu Ala
                565                 570                 575

Ala Thr Lys Gly Asp Asp Lys Gln Ala Ile Glu Ser Lys Thr Lys Ala
            580                 585                 590

Leu Glu Glu Ala Phe Ala Pro Ile Ala Gln Lys Ala Tyr Ala Glu Gln
        595                 600                 605

Ala Gln Ala Ala Val Ala Gln Gly Gly Ala Lys Ala Glu Glu Pro Lys
610                 615                 620

Lys Glu Glu Asp Val Val Asp Ala Asp Phe Glu Asp Val Glu Asp Asp
                625                 630                 635                 640

Lys Lys
```

<210> SEQ ID NO 7
<211> LENGTH: 921
<212> TYPE: DNA
<213> ORGANISM: Francisella tularensis
<220> FEATURE:
<221> NAME/KEY: CDS
<222> LOCATION: (1)..(921)

<400> SEQUENCE: 7

```
atg tca aaa aca gct gta gtt ttt cct ggt caa ggt tca caa aaa cta       48
Met Ser Lys Thr Ala Val Val Phe Pro Gly Gln Gly Ser Gln Lys Leu
1               5                   10                  15 ggg atg ctc caa gat tat tat gaa aat ttt gaa acg ttt aga aat ata       96
Gly Met Leu Gln Asp Tyr Tyr Glu Asn Phe Glu Thr Phe Arg Asn Ile
            20                  25                  30 gtc gat gaa gct aaa gaa cac ctt ggc tac gac tta tgg aat att att      144
Val Asp Glu Ala Lys Glu His Leu Gly Tyr Asp Leu Trp Asn Ile Ile
        35                  40                  45 caa aat gat gaa gaa act cta aat aaa aca gag ttt acc cag cca gca      192
Gln Asn Asp Glu Glu Thr Leu Asn Lys Thr Glu Phe Thr Gln Pro Ala
    50                  55                  60 tta ctt gca act agt tat gca ata tat gaa gtc tta aaa gag caa aag      240
Leu Leu Ala Thr Ser Tyr Ala Ile Tyr Glu Val Leu Lys Glu Gln Lys
65                  70                  75                  80 cca gac tta aaa ata gca tac ttt gca gga cat agt tta ggt gaa tac      288
Pro Asp Leu Lys Ile Ala Tyr Phe Ala Gly His Ser Leu Gly Glu Tyr
                85                  90                  95 act gcc cta ctt gct gct gga tgt att tca tac aaa gat gct tta caa      336
Thr Ala Leu Leu Ala Ala Gly Cys Ile Ser Tyr Lys Asp Ala Leu Gln
            100                 105                 110 ctt gta tct aca cgt ggc aaa tta atg caa aat gct gtt act gac aaa      384
Leu Val Ser Thr Arg Gly Lys Leu Met Gln Asn Ala Val Thr Asp Lys
        115                 120                 125 gaa tgt gct atg agc gca att cta ggt tta tca aat gag gat gta atc      432
Glu Cys Ala Met Ser Ala Ile Leu Gly Leu Ser Asn Glu Asp Val Ile
    130                 135                 140 aaa tct tgt caa gaa gct agt gat gct gga att gtt gaa gct gca aac      480
Lys Ser Cys Gln Glu Ala Ser Asp Ala Gly Ile Val Glu Ala Ala Asn
145                 150                 155                 160
```

```
ttt aac tca aca gga caa gtt gtc atc tct ggg gaa aaa gcc gct gtt      528
Phe Asn Ser Thr Gly Gln Val Val Ile Ser Gly Glu Lys Ala Ala Val
            165                 170                 175 gag aaa gct aat aca ata gct aaa gaa aaa ggt gca aaa cgc gcg cag      576
Glu Lys Ala Asn Thr Ile Ala Lys Glu Lys Gly Ala Lys Arg Ala Gln
180                 185                 190 ata ctt gct gtt agc gta cct tca cat tgt tct tta atg aag gat gct      624
Ile Leu Ala Val Ser Val Pro Ser His Cys Ser Leu Met Lys Asp Ala
    195                 200                 205 gca gat aaa ttt gaa gca gag tta aac aaa gta gaa ttt aaa gag cct      672
Ala Asp Lys Phe Glu Ala Glu Leu Asn Lys Val Glu Phe Lys Glu Pro
210                 215                 220 act acc gct gtt gta caa aac ttt gac gcc aaa tca cac gca aat cca      720
Thr Thr Ala Val Val Gln Asn Phe Asp Ala Lys Ser His Ala Asn Pro
225                 230                 235                 240 gct gaa ata aaa act gct gtt att aaa caa cta tac aag cca gta ctt      768
Ala Glu Ile Lys Thr Ala Val Ile Lys Gln Leu Tyr Lys Pro Val Leu
                245                 250                 255 tgg aca caa tct atc gaa gag cta gtc aaa ctt gga gtc aca gaa gtt      816
Trp Thr Gln Ser Ile Glu Glu Leu Val Lys Leu Gly Val Thr Glu Val
                260                 265                 270 atc gaa tgt ggt cct aac aag gtc tta tct gga cta atc aaa aga ata      864
Ile Glu Cys Gly Pro Asn Lys Val Leu Ser Gly Leu Ile Lys Arg Ile
            275                 280                 285 gat aaa tca ata gat ata aaa gat aca aac agt att gat agt tta gaa      912
Asp Lys Ser Ile Asp Ile Lys Asp Thr Asn Ser Ile Asp Ser Leu Glu
290                 295                 300 aat att taa                                                          921
Asn Ile
305

<210> SEQ ID NO 8
<211> LENGTH: 306
<212> TYPE: PRT
<213> ORGANISM: Francisella tularensis

<400> SEQUENCE: 8

Met Ser Lys Thr Ala Val Val Phe Pro Gly Gln Gly Ser Gln Lys Leu
1               5                   10                  15

Gly Met Leu Gln Asp Tyr Tyr Glu Asn Phe Glu Thr Phe Arg Asn Ile
            20                  25                  30

Val Asp Glu Ala Lys Glu His Leu Gly Tyr Asp Leu Trp Asn Ile Ile
        35                  40                  45

Gln Asn Asp Glu Glu Thr Leu Asn Lys Thr Glu Phe Thr Gln Pro Ala
    50                  55                  60

Leu Leu Ala Thr Ser Tyr Ala Ile Tyr Glu Val Leu Lys Glu Gln Lys
65                  70                  75                  80

Pro Asp Leu Lys Ile Ala Tyr Phe Ala Gly His Ser Leu Gly Glu Tyr
                85                  90                  95

Thr Ala Leu Leu Ala Ala Gly Cys Ile Ser Tyr Lys Asp Ala Leu Gln
            100                 105                 110

Leu Val Ser Thr Arg Gly Lys Leu Met Gln Asn Ala Val Thr Asp Lys
        115                 120                 125

Glu Cys Ala Met Ser Ala Ile Leu Gly Leu Ser Asn Glu Asp Val Ile
    130                 135                 140

Lys Ser Cys Gln Glu Ala Ser Asp Ala Gly Ile Val Glu Ala Ala Asn
145                 150                 155                 160

Phe Asn Ser Thr Gly Gln Val Val Ile Ser Gly Glu Lys Ala Ala Val
                165                 170                 175
```

```
Glu Lys Ala Asn Thr Ile Ala Lys Glu Lys Gly Ala Lys Arg Ala Gln
            180                 185                 190

Ile Leu Ala Val Ser Val Pro Ser His Cys Ser Leu Met Lys Asp Ala
        195                 200                 205

Ala Asp Lys Phe Glu Ala Glu Leu Asn Lys Val Glu Phe Lys Glu Pro
    210                 215                 220

Thr Thr Ala Val Val Gln Asn Phe Asp Ala Lys Ser His Ala Asn Pro
225                 230                 235                 240

Ala Glu Ile Lys Thr Ala Val Ile Lys Gln Leu Tyr Lys Pro Val Leu
                245                 250                 255

Trp Thr Gln Ser Ile Glu Glu Leu Val Lys Leu Gly Val Thr Glu Val
            260                 265                 270

Ile Glu Cys Gly Pro Asn Lys Val Leu Ser Gly Leu Ile Lys Arg Ile
        275                 280                 285

Asp Lys Ser Ile Asp Ile Lys Asp Thr Asn Ser Ile Asp Ser Leu Glu
    290                 295                 300

Asn Ile
305

<210> SEQ ID NO 9
<211> LENGTH: 1638
<212> TYPE: DNA
<213> ORGANISM: Francisella tularensis
<220> FEATURE:
<221> NAME/KEY: CDS
<222> LOCATION: (1)..(1638)

<400> SEQUENCE: 9 atg gct gca aaa caa gtt tta ttt tca gat gaa gct cgt gca aaa atg     48
Met Ala Ala Lys Gln Val Leu Phe Ser Asp Glu Ala Arg Ala Lys Met
1               5                   10                  15 cta gat ggt gtt aac aca cta gca aat gct gta aaa gtt act tta ggt     96
Leu Asp Gly Val Asn Thr Leu Ala Asn Ala Val Lys Val Thr Leu Gly
            20                  25                  30 cca aaa ggt cgt aat gtt gtt tta gat aaa tca ttt ggc acg cct act    144
Pro Lys Gly Arg Asn Val Val Leu Asp Lys Ser Phe Gly Thr Pro Thr
        35                  40                  45 atc act aaa gat ggt gta tct gtt gct aaa gaa att gaa cta gaa gat    192
Ile Thr Lys Asp Gly Val Ser Val Ala Lys Glu Ile Glu Leu Glu Asp
    50                  55                  60 aag ttt gag aat atg ggt gct cag ata gtt aaa gaa gta gct tca aag    240
Lys Phe Glu Asn Met Gly Ala Gln Ile Val Lys Glu Val Ala Ser Lys
65                  70                  75                  80 aca gcg gat gtt gct ggt gat ggt act act aca gcg act gta ctt gct    288
Thr Ala Asp Val Ala Gly Asp Gly Thr Thr Thr Ala Thr Val Leu Ala
                85                  90                  95 cag gca tta ttg aca gag ggt cta aaa gct gtc gct gca ggt atg aat    336
Gln Ala Leu Leu Thr Glu Gly Leu Lys Ala Val Ala Ala Gly Met Asn
            100                 105                 110 cct atg gat cta aaa aga ggt atc gac aaa gca act gct agg tta gtt    384
Pro Met Asp Leu Lys Arg Gly Ile Asp Lys Ala Thr Ala Arg Leu Val
        115                 120                 125 gaa gaa tta aaa gca ctt tct aaa cca tgt tca gat cca aaa tca att    432
Glu Glu Leu Lys Ala Leu Ser Lys Pro Cys Ser Asp Pro Lys Ser Ile
    130                 135                 140 gag caa gtt ggt act atc tct gct aac tct gat gct act gta ggt aag    480
Glu Gln Val Gly Thr Ile Ser Ala Asn Ser Asp Ala Thr Val Gly Lys
145                 150                 155                 160 ctt atc gct gac gca atg gca aaa gtt ggt aaa gaa ggt gtg att aca    528
```

```
                Leu Ile Ala Asp Ala Met Ala Lys Val Gly Lys Glu Gly Val Ile Thr
                                165                 170                 175 gtt gaa gaa ggc aaa ggc ttt gaa gat gag ctt gat gta gtt gaa ggt       576
Val Glu Glu Gly Lys Gly Phe Glu Asp Glu Leu Asp Val Val Glu Gly
            180                 185                 190 atg cag ttt gat aga ggt tat cta tct ccg tat ttt gca aca aat caa       624
Met Gln Phe Asp Arg Gly Tyr Leu Ser Pro Tyr Phe Ala Thr Asn Gln
        195                 200                 205 gag aat atg act act gat tta gag aat cca tat att cta ata gtt gat       672
Glu Asn Met Thr Thr Asp Leu Glu Asn Pro Tyr Ile Leu Ile Val Asp
    210                 215                 220 aag aaa atc tct aat atc cgc gat tta tta ccg ata tta gaa ggt gtt       720
Lys Lys Ile Ser Asn Ile Arg Asp Leu Leu Pro Ile Leu Glu Gly Val
225                 230                 235                 240 tct aaa tct ggt aga gcg tta cta ata ata gct gaa gat gta gaa agt       768
Ser Lys Ser Gly Arg Ala Leu Leu Ile Ile Ala Glu Asp Val Glu Ser
                245                 250                 255 gaa gct cta gct act tta gtt gta aat aat atg cgt ggt gta gtt aaa       816
Glu Ala Leu Ala Thr Leu Val Val Asn Asn Met Arg Gly Val Val Lys
            260                 265                 270 gta tgt gct gtc aaa gct cct ggc ttt ggt gat aga aga aaa gct atg       864
Val Cys Ala Val Lys Ala Pro Gly Phe Gly Asp Arg Arg Lys Ala Met
        275                 280                 285 cta gaa gat atc gct act cta act gga gct acg ttt gta tca gaa gac       912
Leu Glu Asp Ile Ala Thr Leu Thr Gly Ala Thr Phe Val Ser Glu Asp
    290                 295                 300 cta agc atg aag tta gaa gaa act aac atg gag cat tta ggt acg gct       960
Leu Ser Met Lys Leu Glu Glu Thr Asn Met Glu His Leu Gly Thr Ala
305                 310                 315                 320 agt aga gta caa gta aca aaa gat aat aca aca att att gat ggt gct      1008
Ser Arg Val Gln Val Thr Lys Asp Asn Thr Thr Ile Ile Asp Gly Ala
                325                 330                 335 ggt gaa aaa gaa gct atc gct aaa cga ata aat gta atc aaa gct aat      1056
Gly Glu Lys Glu Ala Ile Ala Lys Arg Ile Asn Val Ile Lys Ala Asn
            340                 345                 350 att gct gaa gct aac tct gat tat gat cgt gag aag ctg caa gaa aga      1104
Ile Ala Glu Ala Asn Ser Asp Tyr Asp Arg Glu Lys Leu Gln Glu Arg
        355                 360                 365 ttg gct aaa ctt tct ggt ggt gtc gcg gtg ata aaa gtt ggt gct gtt      1152
Leu Ala Lys Leu Ser Gly Gly Val Ala Val Ile Lys Val Gly Ala Val
    370                 375                 380 aca gaa gct gag atg aaa gag aag aaa gat cgt gtc gat gat gct tta      1200
Thr Glu Ala Glu Met Lys Glu Lys Lys Asp Arg Val Asp Asp Ala Leu
385                 390                 395                 400 cat gct act cgt gcg gct gta gaa gaa ggt att gtt gct ggt ggt ggc      1248
His Ala Thr Arg Ala Ala Val Glu Glu Gly Ile Val Ala Gly Gly Gly
                405                 410                 415 gtt gct tta att aga gca caa aaa gca tta gat ggc tta aca ggt gaa      1296
Val Ala Leu Ile Arg Ala Gln Lys Ala Leu Asp Gly Leu Thr Gly Glu
            420                 425                 430 aat gac gat caa aac tat ggt ata gcg cta ctt aga aaa gca ata gaa      1344
Asn Asp Asp Gln Asn Tyr Gly Ile Ala Leu Leu Arg Lys Ala Ile Glu
        435                 440                 445 gct cct cta aga cag ata gta tca aat gct ggc ggt gag tct tct gta      1392
Ala Pro Leu Arg Gln Ile Val Ser Asn Ala Gly Gly Glu Ser Ser Val
    450                 455                 460 gtt gtt aac caa gtt aaa gct aat caa ggt aac tat ggt tat aat gct      1440
Val Val Asn Gln Val Lys Ala Asn Gln Gly Asn Tyr Gly Tyr Asn Ala
465                 470                 475                 480 gca aat gat act tat ggt gat atg gtt gag atg ggt att tta gat cct      1488
```

```
Ala Asn Asp Thr Tyr Gly Asp Met Val Glu Met Gly Ile Leu Asp Pro
            485                 490                 495 act aaa gtt act cgt tca gct cta caa cat gct gct tca att gct gga    1536
Thr Lys Val Thr Arg Ser Ala Leu Gln His Ala Ala Ser Ile Ala Gly
        500                 505                 510 ctt atg atc act aca gag gcg atg atc ggt gag atc aaa gaa gct gct    1584
Leu Met Ile Thr Thr Glu Ala Met Ile Gly Glu Ile Lys Glu Ala Ala
    515                 520                 525 cct gct atg cct atg ggc ggt ggc atg ggc ggt atg cct ggc atg atg    1632
Pro Ala Met Pro Met Gly Gly Gly Met Gly Gly Met Pro Gly Met Met
530                 535                 540 taa tag                                                             1638

<210> SEQ ID NO 10
<211> LENGTH: 544
<212> TYPE: PRT
<213> ORGANISM: Francisella tularensis

<400> SEQUENCE: 10

Met Ala Ala Lys Gln Val Leu Phe Ser Asp Glu Ala Arg Ala Lys Met
1               5                   10                  15

Leu Asp Gly Val Asn Thr Leu Ala Asn Ala Val Lys Val Thr Leu Gly
            20                  25                  30

Pro Lys Gly Arg Asn Val Leu Asp Lys Ser Phe Gly Thr Pro Thr
        35                  40                  45

Ile Thr Lys Asp Gly Val Ser Val Ala Lys Glu Ile Glu Leu Glu Asp
    50                  55                  60

Lys Phe Glu Asn Met Gly Ala Gln Ile Val Lys Glu Val Ala Ser Lys
65                  70                  75                  80

Thr Ala Asp Val Ala Gly Asp Gly Thr Thr Thr Ala Thr Val Leu Ala
                85                  90                  95

Gln Ala Leu Leu Thr Glu Gly Leu Lys Ala Val Ala Ala Gly Met Asn
            100                 105                 110

Pro Met Asp Leu Lys Arg Gly Ile Asp Lys Ala Thr Ala Arg Leu Val
        115                 120                 125

Glu Glu Leu Lys Ala Leu Ser Lys Pro Cys Ser Asp Pro Lys Ser Ile
    130                 135                 140

Glu Gln Val Gly Thr Ile Ser Ala Asn Ser Asp Ala Thr Val Gly Lys
145                 150                 155                 160

Leu Ile Ala Asp Ala Met Ala Lys Val Gly Lys Glu Gly Val Ile Thr
                165                 170                 175

Val Glu Glu Gly Lys Gly Phe Glu Asp Glu Leu Asp Val Val Glu Gly
            180                 185                 190

Met Gln Phe Asp Arg Gly Tyr Leu Ser Pro Tyr Phe Ala Thr Asn Gln
        195                 200                 205

Glu Asn Met Thr Thr Asp Leu Glu Asn Pro Tyr Ile Leu Ile Val Asp
    210                 215                 220

Lys Lys Ile Ser Asn Ile Arg Asp Leu Leu Pro Ile Leu Glu Gly Val
225                 230                 235                 240

Ser Lys Ser Gly Arg Ala Leu Leu Ile Ile Ala Glu Asp Val Glu Ser
                245                 250                 255

Glu Ala Leu Ala Thr Leu Val Val Asn Asn Met Arg Gly Val Val Lys
            260                 265                 270

Val Cys Ala Val Lys Ala Pro Gly Phe Gly Asp Arg Arg Lys Ala Met
        275                 280                 285

Leu Glu Asp Ile Ala Thr Leu Thr Gly Ala Thr Phe Val Ser Glu Asp
```

```
                        290                 295                 300
Leu Ser Met Lys Leu Glu Glu Thr Asn Met Glu His Leu Gly Thr Ala
305                 310                 315                 320

Ser Arg Val Gln Val Thr Lys Asp Asn Thr Thr Ile Ile Asp Gly Ala
                325                 330                 335

Gly Glu Lys Glu Ala Ile Ala Lys Arg Ile Asn Val Ile Lys Ala Asn
            340                 345                 350

Ile Ala Glu Ala Asn Ser Asp Tyr Asp Arg Glu Lys Leu Gln Glu Arg
        355                 360                 365

Leu Ala Lys Leu Ser Gly Gly Val Ala Val Ile Lys Val Gly Ala Val
    370                 375                 380

Thr Glu Ala Glu Met Lys Glu Lys Lys Asp Arg Val Asp Asp Ala Leu
385                 390                 395                 400

His Ala Thr Arg Ala Ala Val Glu Glu Gly Ile Val Ala Gly Gly Gly
                405                 410                 415

Val Ala Leu Ile Arg Ala Gln Lys Ala Leu Asp Gly Leu Thr Gly Glu
            420                 425                 430

Asn Asp Asp Gln Asn Tyr Gly Ile Ala Leu Leu Arg Lys Ala Ile Glu
        435                 440                 445

Ala Pro Leu Arg Gln Ile Val Ser Asn Ala Gly Gly Glu Ser Ser Val
    450                 455                 460

Val Val Asn Gln Val Lys Ala Asn Gln Gly Asn Tyr Gly Tyr Asn Ala
465                 470                 475                 480

Ala Asn Asp Thr Tyr Gly Asp Met Val Glu Met Gly Ile Leu Asp Pro
                485                 490                 495

Thr Lys Val Thr Arg Ser Ala Leu Gln His Ala Ala Ser Ile Ala Gly
            500                 505                 510

Leu Met Ile Thr Thr Glu Ala Met Ile Gly Glu Ile Lys Glu Ala Ala
        515                 520                 525

Pro Ala Met Pro Met Gly Gly Met Gly Gly Met Pro Gly Met Met
    530                 535                 540

<210> SEQ ID NO 11
<211> LENGTH: 633
<212> TYPE: DNA
<213> ORGANISM: Francisella tularensis
<220> FEATURE:
<221> NAME/KEY: CDS
<222> LOCATION: (1)..(633)

<400> SEQUENCE: 11 atg agt gag atg ata aca aga caa cag gta aca agt ggc gag acc att    48
Met Ser Glu Met Ile Thr Arg Gln Gln Val Thr Ser Gly Glu Thr Ile
1               5                   10                  15 cat gtg aga act gat cct act gca tgt ata gga tct cat cct aat tgt    96
His Val Arg Thr Asp Pro Thr Ala Cys Ile Gly Ser His Pro Asn Cys
                20                  25                  30 aga tta ttt att gat tct tta act ata gct ggg gag aaa ctt gat aaa   144
Arg Leu Phe Ile Asp Ser Leu Thr Ile Ala Gly Glu Lys Leu Asp Lys
            35                  40                  45 aat atc gtt gct ata gat ggt gga gag gat gtc acg aaa gct gat tcg   192
Asn Ile Val Ala Ile Asp Gly Gly Glu Asp Val Thr Lys Ala Asp Ser
        50                  55                  60 gct aca gct gct gct agt gta ata cgt tta tct ata acg cca ggc tct   240
Ala Thr Ala Ala Ala Ser Val Ile Arg Leu Ser Ile Thr Pro Gly Ser
65                  70                  75                  80 ata aat cca aca ata agt att act ctt ggt gtt cta att aaa tca aat   288
Ile Asn Pro Thr Ile Ser Ile Thr Leu Gly Val Leu Ile Lys Ser Asn
```

```
                   85                  90                  95
gtt aga act aaa att gaa gag aaa gtt tcg agt ata tta caa gca agt    336
Val Arg Thr Lys Ile Glu Glu Lys Val Ser Ser Ile Leu Gln Ala Ser
            100                 105                 110 gct aca gat atg aaa att aag tta ggt aat tct aat aaa aaa caa gag    384
Ala Thr Asp Met Lys Ile Lys Leu Gly Asn Ser Asn Lys Lys Gln Glu
            115                 120                 125 tat aaa act gat gaa gca tgg ggt att atg ata gat cta tct aat tta    432
Tyr Lys Thr Asp Glu Ala Trp Gly Ile Met Ile Asp Leu Ser Asn Leu
            130                 135                 140 gag tta tat cca ata agt gct aag gct ttt agt att agt ata gag cca    480
Glu Leu Tyr Pro Ile Ser Ala Lys Ala Phe Ser Ile Ser Ile Glu Pro
145                 150                 155                 160 aca gaa ctt atg ggt gtt tca aaa gat gga atg aga tat cat att ata    528
Thr Glu Leu Met Gly Val Ser Lys Asp Gly Met Arg Tyr His Ile Ile
            165                 170                 175 tct ata gat ggt ctt aca aca tct caa gga agt ttg cca gta tgt tgc    576
Ser Ile Asp Gly Leu Thr Thr Ser Gln Gly Ser Leu Pro Val Cys Cys
            180                 185                 190 gca gct agc aca gat aaa gga gtt gct aaa ata gga tat att gca gct    624
Ala Ala Ser Thr Asp Lys Gly Val Ala Lys Ile Gly Tyr Ile Ala Ala
            195                 200                 205 gca tag taa                                                        633
Ala

<210> SEQ ID NO 12
<211> LENGTH: 209
<212> TYPE: PRT
<213> ORGANISM: Francisella tularensis

<400> SEQUENCE: 12

Met Ser Glu Met Ile Thr Arg Gln Gln Val Thr Ser Gly Glu Thr Ile
1               5                   10                  15

His Val Arg Thr Asp Pro Thr Ala Cys Ile Gly Ser His Pro Asn Cys
            20                  25                  30

Arg Leu Phe Ile Asp Ser Leu Thr Ile Ala Gly Glu Lys Leu Asp Lys
        35                  40                  45

Asn Ile Val Ala Ile Asp Gly Gly Glu Asp Val Thr Lys Ala Asp Ser
    50                  55                  60

Ala Thr Ala Ala Ala Ser Val Ile Arg Leu Ser Ile Thr Pro Gly Ser
65                  70                  75                  80

Ile Asn Pro Thr Ile Ser Ile Thr Leu Gly Val Leu Ile Lys Ser Asn
                85                  90                  95

Val Arg Thr Lys Ile Glu Glu Lys Val Ser Ser Ile Leu Gln Ala Ser
            100                 105                 110

Ala Thr Asp Met Lys Ile Lys Leu Gly Asn Ser Asn Lys Lys Gln Glu
        115                 120                 125

Tyr Lys Thr Asp Glu Ala Trp Gly Ile Met Ile Asp Leu Ser Asn Leu
    130                 135                 140

Glu Leu Tyr Pro Ile Ser Ala Lys Ala Phe Ser Ile Ser Ile Glu Pro
145                 150                 155                 160

Thr Glu Leu Met Gly Val Ser Lys Asp Gly Met Arg Tyr His Ile Ile
                165                 170                 175

Ser Ile Asp Gly Leu Thr Thr Ser Gln Gly Ser Leu Pro Val Cys Cys
            180                 185                 190

Ala Ala Ser Thr Asp Lys Gly Val Ala Lys Ile Gly Tyr Ile Ala Ala
        195                 200                 205
```

Ala

```
<210> SEQ ID NO 13
<211> LENGTH: 2226
<212> TYPE: DNA
<213> ORGANISM: Francisella tularensis
<220> FEATURE:
<221> NAME/KEY: CDS
<222> LOCATION: (1)..(2226)

<400> SEQUENCE: 13
```

| | | | | | | | | | | | | | | | | |
|---|---|---|---|---|---|---|---|---|---|---|---|---|---|---|---|---|
| atg | cta | aag | aaa | att | gta | act | gct | tta | gga | atg | tct | gga | atg | cta | cta | 48 |
| Met | Leu | Lys | Lys | Ile | Val | Thr | Ala | Leu | Gly | Met | Ser | Gly | Met | Leu | Leu | |
| 1 | | | | 5 | | | | | 10 | | | | | 15 | | |
| gct | tct | agc | aat | gct | atc | gca | gaa | gat | acc | aca | acg | aaa | aat | gat | aat | 96 |
| Ala | Ser | Ser | Asn | Ala | Ile | Ala | Glu | Asp | Thr | Thr | Thr | Lys | Asn | Asp | Asn | |
| | | | 20 | | | | | 25 | | | | | 30 | | | |
| ctt | tca | cca | cag | agc | gta | gat | tta | tca | cca | ttg | cgc | aat | tta | aat | aag | 144 |
| Leu | Ser | Pro | Gln | Ser | Val | Asp | Leu | Ser | Pro | Leu | Arg | Asn | Leu | Asn | Lys | |
| | 35 | | | | | 40 | | | | | 45 | | | | | |
| ctt | gat | agc | cca | atg | gat | aaa | gat | tat | aac | tat | cat | caa | gct | ttc | aaa | 192 |
| Leu | Asp | Ser | Pro | Met | Asp | Lys | Asp | Tyr | Asn | Tyr | His | Gln | Ala | Phe | Lys | |
| 50 | | | | | 55 | | | | | 60 | | | | | | |
| aaa | cta | gat | act | gaa | cag | ctt | aaa | aaa | gat | atg | caa | gat | ctt | tta | acc | 240 |
| Lys | Leu | Asp | Thr | Glu | Gln | Leu | Lys | Lys | Asp | Met | Gln | Asp | Leu | Leu | Thr | |
| 65 | | | | | 70 | | | | | 75 | | | | | 80 | |
| cag | tca | caa | gac | tgg | tgg | cct | gct | gat | ttt | ggc | aat | tat | ggt | cct | ttc | 288 |
| Gln | Ser | Gln | Asp | Trp | Trp | Pro | Ala | Asp | Phe | Gly | Asn | Tyr | Gly | Pro | Phe | |
| | | | | 85 | | | | | 90 | | | | | 95 | | |
| ttt | att | aga | cta | tcg | tgg | cat | gat | gct | ggt | aca | tac | aga | ata | tat | gat | 336 |
| Phe | Ile | Arg | Leu | Ser | Trp | His | Asp | Ala | Gly | Thr | Tyr | Arg | Ile | Tyr | Asp | |
| | | | 100 | | | | | 105 | | | | | 110 | | | |
| ggc | aga | gga | ggc | gct | aat | cgt | gga | caa | caa | agg | ttc | tcc | cct | tta | aat | 384 |
| Gly | Arg | Gly | Gly | Ala | Asn | Arg | Gly | Gln | Gln | Arg | Phe | Ser | Pro | Leu | Asn | |
| | 115 | | | | | 120 | | | | | 125 | | | | | |
| agc | tgg | cca | gat | aat | gtt | aat | ctt | gac | aaa | gca | agg | caa | ctt | tta | tgg | 432 |
| Ser | Trp | Pro | Asp | Asn | Val | Asn | Leu | Asp | Lys | Ala | Arg | Gln | Leu | Leu | Trp | |
| 130 | | | | | 135 | | | | | 140 | | | | | | |
| cca | atc | aaa | caa | aaa | tat | ggt | gat | gct | gtt | tca | tgg | tct | gat | ttg | att | 480 |
| Pro | Ile | Lys | Gln | Lys | Tyr | Gly | Asp | Ala | Val | Ser | Trp | Ser | Asp | Leu | Ile | |
| 145 | | | | | 150 | | | | | 155 | | | | | 160 | |
| gtt | tta | gct | ggt | act | gtt | tct | tta | gaa | tca | atg | gga | atg | aag | cct | ata | 528 |
| Val | Leu | Ala | Gly | Thr | Val | Ser | Leu | Glu | Ser | Met | Gly | Met | Lys | Pro | Ile | |
| | | | | 165 | | | | | 170 | | | | | 175 | | |
| ggg | ttt | gct | ttt | ggt | aga | gaa | gac | gac | tgg | caa | ggt | gat | gat | aca | aac | 576 |
| Gly | Phe | Ala | Phe | Gly | Arg | Glu | Asp | Asp | Trp | Gln | Gly | Asp | Asp | Thr | Asn | |
| | | | 180 | | | | | 185 | | | | | 190 | | | |
| tgg | gga | cta | tca | cct | gaa | gag | ata | atg | tct | agt | aat | gta | aga | gat | ggc | 624 |
| Trp | Gly | Leu | Ser | Pro | Glu | Glu | Ile | Met | Ser | Ser | Asn | Val | Arg | Asp | Gly | |
| | 195 | | | | | 200 | | | | | 205 | | | | | |
| aaa | ctt | gct | cct | gca | tac | gcc | gca | aca | caa | atg | ggg | cta | ata | tat | gta | 672 |
| Lys | Leu | Ala | Pro | Ala | Tyr | Ala | Ala | Thr | Gln | Met | Gly | Leu | Ile | Tyr | Val | |
| 210 | | | | | 215 | | | | | 220 | | | | | | |
| aat | cca | gaa | ggt | cct | gat | ggt | aaa | cct | gat | atc | aaa | ggt | gca | gct | agt | 720 |
| Asn | Pro | Glu | Gly | Pro | Asp | Gly | Lys | Pro | Asp | Ile | Lys | Gly | Ala | Ala | Ser | |
| 225 | | | | | 230 | | | | | 235 | | | | | 240 | |
| gaa | att | cgt | cag | gcc | ttc | cga | gct | atg | ggg | atg | aca | gat | aaa | gaa | act | 768 |
| Glu | Ile | Arg | Gln | Ala | Phe | Arg | Ala | Met | Gly | Met | Thr | Asp | Lys | Glu | Thr | |
| | | | | 245 | | | | | 250 | | | | | 255 | | |
| gtc | gcc | cta | att | gca | ggc | ggt | cat | aca | ttt | ggt | aaa | act | cat | ggt | gca | 816 |
| Val | Ala | Leu | Ile | Ala | Gly | Gly | His | Thr | Phe | Gly | Lys | Thr | His | Gly | Ala | |
| | | | 260 | | | | | 265 | | | | | 270 | | | |

```
gtt cca gag gat aaa gtc aaa caa gca att gga cct gct cct gat aag    864
Val Pro Glu Asp Lys Val Lys Gln Ala Ile Gly Pro Ala Pro Asp Lys
            275                 280                 285 gcg cct att gag cag caa ggt cta ggc tgg cac aat agt tat ggc act    912
Ala Pro Ile Glu Gln Gln Gly Leu Gly Trp His Asn Ser Tyr Gly Thr
        290                 295                 300 gga aat ggt gat gat act atg ggt agc ggt ctt gaa ggc tct tgg act    960
Gly Asn Gly Asp Asp Thr Met Gly Ser Gly Leu Glu Gly Ser Trp Thr
305                 310                 315                 320 tct act cca act ttt tgg aat cat gat ttc tta cat aac ctt tac aac   1008
Ser Thr Pro Thr Phe Trp Asn His Asp Phe Leu His Asn Leu Tyr Asn
                325                 330                 335 tta gac tgg aag aaa aca ctt agc cct gct gga gct cac caa tgg act   1056
Leu Asp Trp Lys Lys Thr Leu Ser Pro Ala Gly Ala His Gln Trp Thr
            340                 345                 350 cct aca aat gct aag cca gaa aat atg gtt cct gat gct cac aag ccg   1104
Pro Thr Asn Ala Lys Pro Glu Asn Met Val Pro Asp Ala His Lys Pro
        355                 360                 365 ggt gta aaa cat aaa cct ata atg ttt aca aca gac tta gcg cta aaa   1152
Gly Val Lys His Lys Pro Ile Met Phe Thr Thr Asp Leu Ala Leu Lys
370                 375                 380 gaa gat gat gga ttt aat aaa tat act caa gag ttc tac aat aat cct   1200
Glu Asp Asp Gly Phe Asn Lys Tyr Thr Gln Glu Phe Tyr Asn Asn Pro
                390                 395                 400
385 gaa gaa ttt aaa gaa gag ttt gct aaa gca tgg ttt aaa tta aca cat   1248
Glu Glu Phe Lys Glu Glu Phe Ala Lys Ala Trp Phe Lys Leu Thr His
            405                 410                 415 aga gat atg gga cca aaa tct aga tat ata ggt cct tgg att cct gag   1296
Arg Asp Met Gly Pro Lys Ser Arg Tyr Ile Gly Pro Trp Ile Pro Glu
        420                 425                 430 caa aac ttt att tgg cag gat cct gtt cca gca gca gac tat aag caa   1344
Gln Asn Phe Ile Trp Gln Asp Pro Val Pro Ala Ala Asp Tyr Lys Gln
435                 440                 445 gtg tct aca caa gat att gcc caa ctt gag caa gat att ata aac tct   1392
Val Ser Thr Gln Asp Ile Ala Gln Leu Glu Gln Asp Ile Ile Asn Ser
450                 455                 460 gga tta act aat cag caa ctt ata aaa act gct tgg gat tca gct tct   1440
Gly Leu Thr Asn Gln Gln Leu Ile Lys Thr Ala Trp Asp Ser Ala Ser
465                 470                 475                 480 act tat cgt aaa acc gac tat aga ggt ggc tca aat ggt gca agg att   1488
Thr Tyr Arg Lys Thr Asp Tyr Arg Gly Gly Ser Asn Gly Ala Arg Ile
            485                 490                 495 gct tta gct cca gag aaa gat tgg caa atg aat gaa cca gct aaa ctt   1536
Ala Leu Ala Pro Glu Lys Asp Trp Gln Met Asn Glu Pro Ala Lys Leu
        500                 505                 510 gaa gtt gtt ctt act aag ctt aaa gag att caa acc aac ttt aac aat   1584
Glu Val Val Leu Thr Lys Leu Lys Glu Ile Gln Thr Asn Phe Asn Asn
515                 520                 525 agc aaa act gat ggt aca aaa gta tca ttg gct gac tta ata gtg cta   1632
Ser Lys Thr Asp Gly Thr Lys Val Ser Leu Ala Asp Leu Ile Val Leu
            530                 535                 540 ggt ggt aat gtg ggt gtt gag caa gca gct aaa caa gct ggt tat aat   1680
Gly Gly Asn Val Gly Val Glu Gln Ala Ala Lys Gln Ala Gly Tyr Asn
545                 550                 555                 560 ata caa atg cct ttt gta cca ggt aga aca gat gct act caa gct caa   1728
Ile Gln Met Pro Phe Val Pro Gly Arg Thr Asp Ala Thr Gln Ala Gln
                565                 570                 575 act gac ata gag tct ttc aac tat cta aaa acc aaa tct gat ggt ttt   1776
Thr Asp Ile Glu Ser Phe Asn Tyr Leu Lys Thr Lys Ser Asp Gly Phe
            580                 585                 590
```

```
ata aac tat aca gat ggt agt gta agt gct gat aaa tta cca cag act      1824
Ile Asn Tyr Thr Asp Gly Ser Val Ser Ala Asp Lys Leu Pro Gln Thr
            595                 600                 605 tta gta gaa aaa gct agc atg ctt gac tta aat atc cca gaa atg aca      1872
Leu Val Glu Lys Ala Ser Met Leu Asp Leu Asn Ile Pro Glu Met Thr
610                 615                 620 gtg tta gtc ggt ggt atg cgt gct ctt gat gtc aat tat gat aac tca      1920
Val Leu Val Gly Gly Met Arg Ala Leu Asp Val Asn Tyr Asp Asn Ser
625                 630                 635                 640 caa gaa ggt gta tta act act act cca ggt cag ctt aat aat agc ttc      1968
Gln Glu Gly Val Leu Thr Thr Thr Pro Gly Gln Leu Asn Asn Ser Phe
                645                 650                 655 ttt gtg aac ttg cta gat atg tct act caa tgg aaa aaa tct gat aaa      2016
Phe Val Asn Leu Leu Asp Met Ser Thr Gln Trp Lys Lys Ser Asp Lys
            660                 665                 670 aaa gat ggt gag tat att ggt ata gat aga aaa act ggt aag caa aag      2064
Lys Asp Gly Glu Tyr Ile Gly Ile Asp Arg Lys Thr Gly Lys Gln Lys
675                 680                 685 tgg aca gca tcg cca gtt gat cta att ttt gga tca aac tca gag ctt      2112
Trp Thr Ala Ser Pro Val Asp Leu Ile Phe Gly Ser Asn Ser Glu Leu
690                 695                 700 aaa gca gta gct caa gtt tat gct gaa aat ggt aat gag caa aaa ttt      2160
Lys Ala Val Ala Gln Val Tyr Ala Glu Asn Gly Asn Glu Gln Lys Phe
705                 710                 715                 720 gta aat gac ttt gca aaa gct tgg cat aaa gtt atg atg ctt ggc aga      2208
Val Asn Asp Phe Ala Lys Ala Trp His Lys Val Met Met Leu Gly Arg
                725                 730                 735 ttt gat gtt caa caa taa                                              2226
Phe Asp Val Gln Gln
            740

<210> SEQ ID NO 14
<211> LENGTH: 741
<212> TYPE: PRT
<213> ORGANISM: Francisella tularensis

<400> SEQUENCE: 14

Met Leu Lys Lys Ile Val Thr Ala Leu Gly Met Ser Gly Met Leu Leu
1               5                   10                  15

Ala Ser Ser Asn Ala Ile Ala Glu Asp Thr Thr Thr Lys Asn Asp Asn
            20                  25                  30

Leu Ser Pro Gln Ser Val Asp Leu Ser Pro Leu Arg Asn Leu Asn Lys
        35                  40                  45

Leu Asp Ser Pro Met Asp Lys Asp Tyr Asn Tyr His Gln Ala Phe Lys
    50                  55                  60

Lys Leu Asp Thr Glu Gln Leu Lys Lys Asp Met Gln Asp Leu Leu Thr
65                  70                  75                  80

Gln Ser Gln Asp Trp Trp Pro Ala Asp Phe Gly Asn Tyr Gly Pro Phe
                85                  90                  95

Phe Ile Arg Leu Ser Trp His Asp Ala Gly Thr Tyr Arg Ile Tyr Asp
            100                 105                 110

Gly Arg Gly Gly Ala Asn Arg Gly Gln Gln Arg Phe Ser Pro Leu Asn
        115                 120                 125

Ser Trp Pro Asp Asn Val Asn Leu Asp Lys Ala Arg Gln Leu Leu Trp
    130                 135                 140

Pro Ile Lys Gln Lys Tyr Gly Asp Ala Val Ser Trp Ser Asp Leu Ile
145                 150                 155                 160

Val Leu Ala Gly Thr Val Ser Leu Glu Ser Met Gly Met Lys Pro Ile
```

-continued

```
                165                 170                 175
Gly Phe Ala Phe Gly Arg Glu Asp Asp Trp Gln Gly Asp Asp Thr Asn
            180                 185                 190
Trp Gly Leu Ser Pro Glu Glu Ile Met Ser Ser Asn Val Arg Asp Gly
        195                 200                 205
Lys Leu Ala Pro Ala Tyr Ala Ala Thr Gln Met Gly Leu Ile Tyr Val
    210                 215                 220
Asn Pro Glu Gly Pro Asp Gly Lys Pro Asp Ile Lys Gly Ala Ala Ser
225                 230                 235                 240
Glu Ile Arg Gln Ala Phe Arg Ala Met Gly Met Thr Asp Lys Glu Thr
                245                 250                 255
Val Ala Leu Ile Ala Gly Gly His Thr Phe Gly Lys Thr His Gly Ala
            260                 265                 270
Val Pro Glu Asp Lys Val Lys Gln Ala Ile Gly Pro Ala Pro Asp Lys
        275                 280                 285
Ala Pro Ile Glu Gln Gln Gly Leu Gly Trp His Asn Ser Tyr Gly Thr
    290                 295                 300
Gly Asn Gly Asp Asp Thr Met Gly Ser Gly Leu Glu Gly Ser Trp Thr
305                 310                 315                 320
Ser Thr Pro Thr Phe Trp Asn His Asp Phe Leu His Asn Leu Tyr Asn
                325                 330                 335
Leu Asp Trp Lys Lys Thr Leu Ser Pro Ala Gly Ala His Gln Trp Thr
            340                 345                 350
Pro Thr Asn Ala Lys Pro Glu Asn Met Val Pro Asp Ala His Lys Pro
        355                 360                 365
Gly Val Lys His Lys Pro Ile Met Phe Thr Thr Asp Leu Ala Leu Lys
    370                 375                 380
Glu Asp Asp Gly Phe Asn Lys Tyr Thr Gln Glu Phe Tyr Asn Asn Pro
385                 390                 395                 400
Glu Glu Phe Lys Glu Glu Phe Ala Lys Ala Trp Phe Lys Leu Thr His
                405                 410                 415
Arg Asp Met Gly Pro Lys Ser Arg Tyr Ile Gly Pro Trp Ile Pro Glu
            420                 425                 430
Gln Asn Phe Ile Trp Gln Asp Pro Val Pro Ala Ala Asp Tyr Lys Gln
        435                 440                 445
Val Ser Thr Gln Asp Ile Ala Gln Leu Glu Gln Asp Ile Ile Asn Ser
    450                 455                 460
Gly Leu Thr Asn Gln Gln Leu Ile Lys Thr Ala Trp Asp Ser Ala Ser
465                 470                 475                 480
Thr Tyr Arg Lys Thr Asp Tyr Arg Gly Gly Ser Asn Gly Ala Arg Ile
                485                 490                 495
Ala Leu Ala Pro Glu Lys Asp Trp Gln Met Asn Glu Pro Ala Lys Leu
            500                 505                 510
Glu Val Val Leu Thr Lys Leu Lys Glu Ile Gln Thr Asn Phe Asn Asn
        515                 520                 525
Ser Lys Thr Asp Gly Thr Lys Val Ser Leu Ala Asp Leu Ile Val Leu
    530                 535                 540
Gly Gly Asn Val Gly Val Glu Gln Ala Ala Lys Gln Ala Gly Tyr Asn
545                 550                 555                 560
Ile Gln Met Pro Phe Val Pro Gly Arg Thr Asp Ala Thr Gln Ala Gln
                565                 570                 575
Thr Asp Ile Glu Ser Phe Asn Tyr Leu Lys Thr Lys Ser Asp Gly Phe
            580                 585                 590
```

```
Ile Asn Tyr Thr Asp Gly Ser Val Ser Ala Asp Lys Leu Pro Gln Thr
            595                 600                 605

Leu Val Glu Lys Ala Ser Met Leu Asp Leu Asn Ile Pro Glu Met Thr
610                 615                 620

Val Leu Val Gly Gly Met Arg Ala Leu Asp Val Asn Tyr Asp Asn Ser
625                 630                 635                 640

Gln Glu Gly Val Leu Thr Thr Pro Gly Gln Leu Asn Asn Ser Phe
            645                 650                 655

Phe Val Asn Leu Leu Asp Met Ser Thr Gln Trp Lys Lys Ser Asp Lys
                660                 665                 670

Lys Asp Gly Glu Tyr Ile Gly Ile Asp Arg Lys Thr Gly Lys Gln Lys
            675                 680                 685

Trp Thr Ala Ser Pro Val Asp Leu Ile Phe Gly Ser Asn Ser Glu Leu
690                 695                 700

Lys Ala Val Ala Gln Val Tyr Ala Glu Asn Gly Asn Glu Gln Lys Phe
705                 710                 715                 720

Val Asn Asp Phe Ala Lys Ala Trp His Lys Val Met Met Leu Gly Arg
                725                 730                 735

Phe Asp Val Gln Gln
            740
```

```
<210> SEQ ID NO 15
<211> LENGTH: 1218
<212> TYPE: DNA
<213> ORGANISM: Francisella tularensis
<220> FEATURE:
<221> NAME/KEY: CDS
<222> LOCATION: (1)..(1218)

<400> SEQUENCE: 15
```

```
atg aga att tta ttt aca att tta gct ttt ttt gga tac agt tat ggg    48
Met Arg Ile Leu Phe Thr Ile Leu Ala Phe Phe Gly Tyr Ser Tyr Gly
1               5                   10                  15 tta gca cat gga att act aaa aca ata gta cac aac tat cct gaa aac    96
Leu Ala His Gly Ile Thr Lys Thr Ile Val His Asn Tyr Pro Glu Asn
                20                  25                  30 ata tca aaa tca ttt caa att agt aac aac aat tat gct cct tta caa   144
Ile Ser Lys Ser Phe Gln Ile Ser Asn Asn Asn Tyr Ala Pro Leu Gln
            35                  40                  45 att agt aaa cta atc cag agt gca aag aaa aat att gat att gaa gta   192
Ile Ser Lys Leu Ile Gln Ser Ala Lys Lys Asn Ile Asp Ile Glu Val
        50                  55                  60 ttc tac ata gat ata aaa aaa gac agt gtt cta gat aag atg ata att   240
Phe Tyr Ile Asp Ile Lys Lys Asp Ser Val Leu Asp Lys Met Ile Ile
65                  70                  75                  80 caa cct tta gca gca aag gct aat caa gga att aaa gtt aga att ttg   288
Gln Pro Leu Ala Ala Lys Ala Asn Gln Gly Ile Lys Val Arg Ile Leu
                85                  90                  95 gtg gat gac aaa ttt tat agc caa tac agc aac aac aaa gct agc tgt   336
Val Asp Asp Lys Phe Tyr Ser Gln Tyr Ser Asn Asn Lys Ala Ser Cys
            100                 105                 110 gat tat tta aac tct att aag aat ata act tgt aaa ccg aca aaa gaa   384
Asp Tyr Leu Asn Ser Ile Lys Asn Ile Thr Cys Lys Pro Thr Lys Glu
        115                 120                 125 ttt caa gaa gct gta atg cac tct aaa atg ata agc att gat ggt aag   432
Phe Gln Glu Ala Val Met His Ser Lys Met Ile Ser Ile Asp Gly Lys
    130                 135                 140 tct ttt tac att ggt agt cat aat ttt gat tgg ata aca ttt gaa ctt   480
Ser Phe Tyr Ile Gly Ser His Asn Phe Asp Trp Ile Thr Phe Glu Leu
145                 150                 155                 160
```

```
aat cat gag cta gga gtt att gtt aaa aat gat aag att aat gct gct        528
Asn His Glu Leu Gly Val Ile Val Lys Asn Asp Lys Ile Asn Ala Ala
            165                 170                 175 aaa ctt gaa aaa tct ttt aat gat gat tgg aac ttt act aat aaa agt        576
Lys Leu Glu Lys Ser Phe Asn Asp Asp Trp Asn Phe Thr Asn Lys Ser
        180                 185                 190 aaa aag cta aca gat aat aac ttg aat aca tac tca ctt cat gac caa        624
Lys Lys Leu Thr Asp Asn Asn Leu Asn Thr Tyr Ser Leu His Asp Gln
    195                 200                 205 gga aat caa gcg att gtg act gtt aca cct gat ata gat aaa aaa ggt        672
Gly Asn Gln Ala Ile Val Thr Val Thr Pro Asp Ile Asp Lys Lys Gly
210                 215                 220 tac cct aaa agt aat cta aaa act ttc ata tca tta att aaa tct gca        720
Tyr Pro Lys Ser Asn Leu Lys Thr Phe Ile Ser Leu Ile Lys Ser Ala
225                 230                 235                 240 aaa tca agt ata gta atc caa gca atg att gta tct gga ata gat cca        768
Lys Ser Ser Ile Val Ile Gln Ala Met Ile Val Ser Gly Ile Asp Pro
                245                 250                 255 tac atg aat gat aaa aac tgg gat gaa ttt aca aaa gcc tta tca gac        816
Tyr Met Asn Asp Lys Asn Trp Asp Glu Phe Thr Lys Ala Leu Ser Asp
            260                 265                 270 gct aat aaa cga aat gtt tat gta aaa att atg ttc tca aat tgg atg        864
Ala Asn Lys Arg Asn Val Tyr Val Lys Ile Met Phe Ser Asn Trp Met
        275                 280                 285 ttt acc aaa tct tcg tat aaa gat agt aat gat tgg cta caa aaa ctg        912
Phe Thr Lys Ser Ser Tyr Lys Asp Ser Asn Asp Trp Leu Gln Lys Leu
    290                 295                 300 att cat caa tca aat caa aat cac tta aag atc aaa tac aca tca tta        960
Ile His Gln Ser Asn Gln Asn His Leu Lys Ile Lys Tyr Thr Ser Leu
305                 310                 315                 320 ccc cat aca aaa caa tgt gta cca ttc tct gaa gta gat cat gca aaa       1008
Pro His Thr Lys Gln Cys Val Pro Phe Ser Glu Val Asp His Ala Lys
                325                 330                 335 tat gct att ttt gat ggt acc ata gca tgg gtt tct act tct aat ata       1056
Tyr Ala Ile Phe Asp Gly Thr Ile Ala Trp Val Ser Thr Ser Asn Ile
            340                 345                 350 caa aaa tcc tac ttc tat gcg gca aaa aac tat tca tac att gct gac       1104
Gln Lys Ser Tyr Phe Tyr Ala Ala Lys Asn Tyr Ser Tyr Ile Ala Asp
        355                 360                 365 gat aaa gac cta tca cgg caa ctg aca gat gtt ttt gag cag ctt tgg       1152
Asp Lys Asp Leu Ser Arg Gln Leu Thr Asp Val Phe Glu Gln Leu Trp
    370                 375                 380 gat agt aaa tat gct cat aca tat tcg caa cct gtt ggt ata ata tca       1200
Asp Ser Lys Tyr Ala His Thr Tyr Ser Gln Pro Val Gly Ile Ile Ser
385                 390                 395                 400 act ccg tct tgt acc taa                                               1218
Thr Pro Ser Cys Thr
                405

<210> SEQ ID NO 16
<211> LENGTH: 405
<212> TYPE: PRT
<213> ORGANISM: Francisella tularensis

<400> SEQUENCE: 16

Met Arg Ile Leu Phe Thr Ile Leu Ala Phe Phe Gly Tyr Ser Tyr Gly
1               5                   10                  15

Leu Ala His Gly Ile Thr Lys Thr Ile Val His Asn Tyr Pro Glu Asn
            20                  25                  30

Ile Ser Lys Ser Phe Gln Ile Ser Asn Asn Asn Tyr Ala Pro Leu Gln
```

```
                35                  40                  45
Ile Ser Lys Leu Ile Gln Ser Ala Lys Asn Ile Asp Ile Glu Val
 50                  55                  60

Phe Tyr Ile Asp Ile Lys Lys Asp Ser Val Leu Asp Lys Met Ile Ile
 65                  70                  75                  80

Gln Pro Leu Ala Ala Lys Ala Asn Gln Gly Ile Lys Val Arg Ile Leu
                 85                  90                  95

Val Asp Asp Lys Phe Tyr Ser Gln Tyr Ser Asn Asn Lys Ala Ser Cys
                100                 105                 110

Asp Tyr Leu Asn Ser Ile Lys Asn Ile Thr Cys Lys Pro Thr Lys Glu
                115                 120                 125

Phe Gln Glu Ala Val Met His Ser Lys Met Ile Ser Ile Asp Gly Lys
                130                 135                 140

Ser Phe Tyr Ile Gly Ser His Asn Phe Asp Trp Ile Thr Phe Glu Leu
145                 150                 155                 160

Asn His Glu Leu Gly Val Ile Val Lys Asn Asp Lys Ile Asn Ala Ala
                165                 170                 175

Lys Leu Glu Lys Ser Phe Asn Asp Asp Trp Asn Phe Thr Asn Lys Ser
                180                 185                 190

Lys Lys Leu Thr Asp Asn Asn Leu Asn Thr Tyr Ser Leu His Asp Gln
                195                 200                 205

Gly Asn Gln Ala Ile Val Thr Val Thr Pro Asp Ile Asp Lys Lys Gly
                210                 215                 220

Tyr Pro Lys Ser Asn Leu Lys Thr Phe Ile Ser Leu Ile Lys Ser Ala
225                 230                 235                 240

Lys Ser Ser Ile Val Ile Gln Ala Met Ile Val Ser Gly Ile Asp Pro
                245                 250                 255

Tyr Met Asn Asp Lys Asn Trp Asp Glu Phe Thr Lys Ala Leu Ser Asp
                260                 265                 270

Ala Asn Lys Arg Asn Val Tyr Val Lys Ile Met Phe Ser Asn Trp Met
                275                 280                 285

Phe Thr Lys Ser Ser Tyr Lys Asp Ser Asn Asp Trp Leu Gln Lys Leu
                290                 295                 300

Ile His Gln Ser Asn Gln Asn His Leu Lys Ile Lys Tyr Thr Ser Leu
305                 310                 315                 320

Pro His Thr Lys Gln Cys Val Pro Phe Ser Glu Val Asp His Ala Lys
                325                 330                 335

Tyr Ala Ile Phe Asp Gly Thr Ile Ala Trp Val Ser Thr Ser Asn Ile
                340                 345                 350

Gln Lys Ser Tyr Phe Tyr Ala Ala Lys Asn Tyr Ser Tyr Ile Ala Asp
                355                 360                 365

Asp Lys Asp Leu Ser Arg Gln Leu Thr Asp Val Phe Glu Gln Leu Trp
                370                 375                 380

Asp Ser Lys Tyr Ala His Thr Tyr Ser Gln Pro Val Gly Ile Ile Ser
385                 390                 395                 400

Thr Pro Ser Cys Thr
                405

<210> SEQ ID NO 17
<211> LENGTH: 579
<212> TYPE: DNA
<213> ORGANISM: Francisella tularensis
<220> FEATURE:
<221> NAME/KEY: CDS
<222> LOCATION: (1)..(579)
```

```
<400> SEQUENCE: 17 atg aaa ttt gaa tta cca aaa cta cct tac gct gtt gat gca tta gag      48
Met Lys Phe Glu Leu Pro Lys Leu Pro Tyr Ala Val Asp Ala Leu Glu
1               5                   10                  15 tca aca ata tca aaa gaa aca ata gag tat cac tat ggt aaa cat cat      96
Ser Thr Ile Ser Lys Glu Thr Ile Glu Tyr His Tyr Gly Lys His His
            20                  25                  30 caa aca tat gta act aat cta aat aat tta gtt gag ggt aca gag cac     144
Gln Thr Tyr Val Thr Asn Leu Asn Asn Leu Val Glu Gly Thr Glu His
        35                  40                  45 gat ggc aga aac cta gaa gaa atc gta aaa act tct aat ggc gga ata     192
Asp Gly Arg Asn Leu Glu Glu Ile Val Lys Thr Ser Asn Gly Gly Ile
    50                  55                  60 ttt aat aac gct gct caa gtt ttt aat cat act ttt tac tgg aat tgt     240
Phe Asn Asn Ala Ala Gln Val Phe Asn His Thr Phe Tyr Trp Asn Cys
65                  70                  75                  80 tta act cca aac aaa aca gaa gct tca agt cag tta aaa gca gca ttg     288
Leu Thr Pro Asn Lys Thr Glu Ala Ser Ser Gln Leu Lys Ala Ala Leu
                85                  90                  95 atc gag aca ttt ggt tct gta gaa aat ttt aaa gaa caa ttc tct aag     336
Ile Glu Thr Phe Gly Ser Val Glu Asn Phe Lys Glu Gln Phe Ser Lys
            100                 105                 110 gca gct att gca aca ttt ggt tct ggt tgg gct tgg tta gta aaa aat     384
Ala Ala Ile Ala Thr Phe Gly Ser Gly Trp Ala Trp Leu Val Lys Asn
        115                 120                 125 act gaa ggt aaa ctt gaa ata gta act aca agt aac gct ggt tgc cca     432
Thr Glu Gly Lys Leu Glu Ile Val Thr Thr Ser Asn Ala Gly Cys Pro
    130                 135                 140 tta aca gag aac aaa aag cca ttg cta act ttt gat gtt tgg gag cac     480
Leu Thr Glu Asn Lys Lys Pro Leu Leu Thr Phe Asp Val Trp Glu His
145                 150                 155                 160 gca tac tat att gat tat cgt aat gct aga cct aaa tat gtt gaa gca     528
Ala Tyr Tyr Ile Asp Tyr Arg Asn Ala Arg Pro Lys Tyr Val Glu Ala
                165                 170                 175 tta tgg gat atc gta aac tgg caa ttt gtt tct gag caa ttc gct gat     576
Leu Trp Asp Ile Val Asn Trp Gln Phe Val Ser Glu Gln Phe Ala Asp
            180                 185                 190 tag                                                                  579

<210> SEQ ID NO 18
<211> LENGTH: 192
<212> TYPE: PRT
<213> ORGANISM: Francisella tularensis

<400> SEQUENCE: 18

Met Lys Phe Glu Leu Pro Lys Leu Pro Tyr Ala Val Asp Ala Leu Glu
1               5                   10                  15

Ser Thr Ile Ser Lys Glu Thr Ile Glu Tyr His Tyr Gly Lys His His
            20                  25                  30

Gln Thr Tyr Val Thr Asn Leu Asn Asn Leu Val Glu Gly Thr Glu His
        35                  40                  45

Asp Gly Arg Asn Leu Glu Glu Ile Val Lys Thr Ser Asn Gly Gly Ile
    50                  55                  60

Phe Asn Asn Ala Ala Gln Val Phe Asn His Thr Phe Tyr Trp Asn Cys
65                  70                  75                  80

Leu Thr Pro Asn Lys Thr Glu Ala Ser Ser Gln Leu Lys Ala Ala Leu
                85                  90                  95

Ile Glu Thr Phe Gly Ser Val Glu Asn Phe Lys Glu Gln Phe Ser Lys
            100                 105                 110
```

```
Ala Ala Ile Ala Thr Phe Gly Ser Gly Trp Ala Trp Leu Val Lys Asn
            115                 120                 125

Thr Glu Gly Lys Leu Glu Ile Val Thr Thr Ser Asn Ala Gly Cys Pro
130                 135                 140

Leu Thr Glu Asn Lys Lys Pro Leu Leu Thr Phe Asp Val Trp Glu His
145                 150                 155                 160

Ala Tyr Tyr Ile Asp Tyr Arg Asn Ala Arg Pro Lys Tyr Val Glu Ala
                165                 170                 175

Leu Trp Asp Ile Val Asn Trp Gln Phe Val Ser Glu Gln Phe Ala Asp
            180                 185                 190

<210> SEQ ID NO 19
<211> LENGTH: 450
<212> TYPE: DNA
<213> ORGANISM: Francisella tularensis
<220> FEATURE:
<221> NAME/KEY: CDS
<222> LOCATION: (1)..(450)

<400> SEQUENCE: 19 atg aaa aaa ata att gag ctt agt ctt tta tct tta tca atc gca ggt        48
Met Lys Lys Ile Ile Glu Leu Ser Leu Leu Ser Leu Ser Ile Ala Gly
1               5                   10                  15 tta gcg agc tgt tct act cta ggg tta ggt ggc tct gat gat gca aaa        96
Leu Ala Ser Cys Ser Thr Leu Gly Leu Gly Gly Ser Asp Asp Ala Lys
                20                  25                  30 gct tca gct aaa gat act gct gct gct cag aca gct act act gag caa       144
Ala Ser Ala Lys Asp Thr Ala Ala Ala Gln Thr Ala Thr Thr Glu Gln
            35                  40                  45 gct gct gct gta tct aag cca act gca aaa gta agt tta aat aaa ctt       192
Ala Ala Ala Val Ser Lys Pro Thr Ala Lys Val Ser Leu Asn Lys Leu
        50                  55                  60 ggt cag gat aaa ata aaa gca act gta tat aca aca tac aat aat aac       240
Gly Gln Asp Lys Ile Lys Ala Thr Val Tyr Thr Thr Tyr Asn Asn Asn
65                  70                  75                  80 cca caa gga agt gta aga tta caa tgg cag gct cca gaa ggt tct aag       288
Pro Gln Gly Ser Val Arg Leu Gln Trp Gln Ala Pro Glu Gly Ser Lys
                85                  90                  95 tgc cat gat aca agc ttc cca att act aag tat gct gag aag aac gat       336
Cys His Asp Thr Ser Phe Pro Ile Thr Lys Tyr Ala Glu Lys Asn Asp
            100                 105                 110 aaa act tgg gca act gta aca gtt aag caa ggt aat aac ttc tgt agc       384
Lys Thr Trp Ala Thr Val Thr Val Lys Gln Gly Asn Asn Phe Cys Ser
        115                 120                 125 ggt aag tgg aca gct aat gta gtt tat gac aaa gaa gta atc gct tct       432
Gly Lys Trp Thr Ala Asn Val Val Tyr Asp Lys Glu Val Ile Ala Ser
130                 135                 140 gat tca ata aat att taa                                                450
Asp Ser Ile Asn Ile
145

<210> SEQ ID NO 20
<211> LENGTH: 149
<212> TYPE: PRT
<213> ORGANISM: Francisella tularensis

<400> SEQUENCE: 20

Met Lys Lys Ile Ile Glu Leu Ser Leu Leu Ser Leu Ser Ile Ala Gly
1               5                   10                  15

Leu Ala Ser Cys Ser Thr Leu Gly Leu Gly Gly Ser Asp Asp Ala Lys
                20                  25                  30
```

Ala Ser Ala Lys Asp Thr Ala Ala Gln Thr Ala Thr Thr Glu Gln
             35                  40                  45

Ala Ala Ala Val Ser Lys Pro Thr Ala Lys Val Ser Leu Asn Lys Leu
         50                  55                  60

Gly Gln Asp Lys Ile Lys Ala Thr Val Tyr Thr Tyr Asn Asn Asn
 65              70                  75                  80

Pro Gln Gly Ser Val Arg Leu Gln Trp Gln Ala Pro Glu Gly Ser Lys
                 85                  90                  95

Cys His Asp Thr Ser Phe Pro Ile Thr Lys Tyr Ala Glu Lys Asn Asp
                100                 105                 110

Lys Thr Trp Ala Thr Val Thr Val Lys Gln Gly Asn Asn Phe Cys Ser
            115                 120                 125

Gly Lys Trp Thr Ala Asn Val Val Tyr Asp Lys Glu Val Ile Ala Ser
130                 135                 140

Asp Ser Ile Asn Ile
145

<210> SEQ ID NO 21
<211> LENGTH: 62
<212> TYPE: DNA
<213> ORGANISM: Artificial Sequence
<220> FEATURE:
<223> OTHER INFORMATION: Forward Primer

<400> SEQUENCE: 21
ccgctcgagc atatgctaaa gaaaattgta actgctttag gaatgtctgg aatgctacta    60
gc                                                                   62

<210> SEQ ID NO 22
<211> LENGTH: 62
<212> TYPE: DNA
<213> ORGANISM: Artificial Sequence
<220> FEATURE:
<223> OTHER INFORMATION: Reverse Primer

<400> SEQUENCE: 22
ccgctcgagt taacaaattt attgttgaac atcaaatctg ccaagcatca taactttatg    60
cc                                                                   62

<210> SEQ ID NO 23
<211> LENGTH: 48
<212> TYPE: DNA
<213> ORGANISM: Artificial Sequence
<220> FEATURE:
<223> OTHER INFORMATION: Forward Primer - groEL

<400> SEQUENCE: 23
cgggatccca tatggctgca aaacaagttt tattttcaga tgaagctc                 48

<210> SEQ ID NO 24
<211> LENGTH: 47
<212> TYPE: DNA
<213> ORGANISM: Artificial Sequence
<220> FEATURE:
<223> OTHER INFORMATION: Reverse Primer - groEL

<400> SEQUENCE: 24
cgggatccct attacatcat gccaggcata ccgcccatgc caccgcc                  47

<210> SEQ ID NO 25
<211> LENGTH: 49

```
<212> TYPE: DNA
<213> ORGANISM: Artificial Sequence
<220> FEATURE:
<223> OTHER INFORMATION: Forward Primer - fabD

<400> SEQUENCE: 25
cgggatccca tatgtcaaaa acagctgtag tttttcctgg tcaaggttc                49

<210> SEQ ID NO 26
<211> LENGTH: 48
<212> TYPE: DNA
<213> ORGANISM: Artificial Sequence
<220> FEATURE:
<223> OTHER INFORMATION: Reverse Primer - fabD

<400> SEQUENCE: 26
cgggatcctt aaatatttc taaactatca atactgtttg tatctttt                 48

<210> SEQ ID NO 27
<211> LENGTH: 46
<212> TYPE: DNA
<213> ORGANISM: Artificial Sequence
<220> FEATURE:
<223> OTHER INFORMATION: Forward Primer - sodB

<400> SEQUENCE: 27
cgggatccgg cttaccacat gatctaattg ccgttgctgc atgcgc                  46

<210> SEQ ID NO 28
<211> LENGTH: 46
<212> TYPE: DNA
<213> ORGANISM: Artificial Sequence
<220> FEATURE:
<223> OTHER INFORMATION: Reverse Primre - sodB

<400> SEQUENCE: 28
cgggatccag ctatcaagat cacaaccact attgataaaa ccccta                  46

<210> SEQ ID NO 29
<211> LENGTH: 46
<212> TYPE: DNA
<213> ORGANISM: Artificial Sequence
<220> FEATURE:
<223> OTHER INFORMATION: Forward Primer - bfr

<400> SEQUENCE: 29
ccggatcccc atctttaaat gtacaggttg tatctagact ttctgc                  46

<210> SEQ ID NO 30
<211> LENGTH: 48
<212> TYPE: DNA
<213> ORGANISM: Artificial Sequence
<220> FEATURE:
<223> OTHER INFORMATION: Reverse Primer - bfr

<400> SEQUENCE: 30
cgggatccgt cactgaatat ctcgatagcg cattctagtg aatccaag                48
```

METHODS AND COMPOSITIONS FOR TREATING TULAREMIA

CROSS REFERENCE TO RELATED APPLICATIONS

This application is filed under 35 U.S.C. §371 and claims priority to International Application No. PCT/US07/22418, filed Oct. 22, 2007, which application claims priority from U.S. Provisional Application Ser. No. 60/854,612, filed Oct. 25, 2006, both of which are incorporated herein by reference.

STATEMENTS REGARDING FEDERALLY SPONSORED RESEARCH

The invention was funded in part by Grant No. DAMD17-03-1-0052 awarded by the Department of Defense. The government has certain rights in the invention.

TECHNICAL FIELD

The invention relates generally to an antigenic composition useful for immunization against tularemia and attenuated vectors and agents. The disclosure is a method for producing a vaccine for preventing tularemia in humans and animals, a new vaccine against tularemia in humans and animals, and a new approach to producing vaccines against tularemia.

BACKGROUND

The Gram-negative bacterium *Francisella tularensis* is the causative agent of the zoonotic disease tularemia. Humans acquire tularemia from contact with infected tissues or materials, insect bites, consumption of contaminated food or water, or inhalation of aerosols. *F. tularensis* consists of 3 subspecies—*tularensis, holarctica* and *mediasiatica*—which differ in their geographic distributions and in their virulence in humans.

A vaccine against *F. tularensis* was developed a half-century ago, but it has not been approved for general use. This vaccine, called Live Vaccine Strain (LVS), is an attenuated form of *Francisella tularensis* subspecies *holarctica*, a much less virulent subspecies of *F. tularensis* than the highly virulent subspecies of concern as a bioterrorist agent, *F. tularensis* subspecies *tularensis*. The LVS vaccine is poorly characterized, unstable in that different colonial morphology types emerge on culture, and toxic to humans vaccinated with the LVS vaccine. Moreover, the LVS vaccine may not protect against the high doses of *F. tularensis* subspecies *tularensis* that might be released in an airborne bioterrorism attack.

SUMMARY

The disclosure provides methods and compositions useful for preventing infection caused by *Francisella tularensis*, the agent of tularemia, and a potential agent of bioterrorism.

The disclosure provides an immunogenic composition comprising a substantially purified polypeptide comprising a sequence selected from the group consisting of SEQ ID NO:2, 4, 6, 8, 10, 12, 14, 16, 18, 20, an immunogenic fragment thereof, and any combination of the foregoing.

The disclosure also provides a composition comprising at least one recombinant attenuated vector (e.g., *L. monocytogenes, F. tularensis* LVS, O-Antigen-deficient *F. tularensis* or an adenoviral vector) comprising at least one polynucleotide encoding one or more *F. tularensis* polypeptides selected from the group consisting of AcpA, Bfr, DnaK, FabD, GroEL, IglC, KatG, Pld, Tul4 and SodB, such that the polypeptide is expressed in the at least one recombinant attenuated vector.

The disclosure further provides a method of inducing protective immunity in a subject comprising administering the composition above to the subject.

The disclosure provides an immunoprotective composition comprising at least one attenuated vector expressing an antigen useful for inducing an immunoprotective response against *Francisella tularensis* (*F. tularensis*), said antigen comprising an extracellular or immunogenic protein of *F. tularensis* or immunogenic fragment thereof linked to transcriptional promoter and termination signals. In one aspect, the *F. tularensis* protein or fragment thereof is selected from the group consisting of AcpA, Bfr, DnaK, FabD, GroEL, IglC, KatG, Pld, Tul4, SodB, and any combination thereof. In another aspect, the attenuated vector is *F. tularensis* including *F. tularensis* LVS strain, O-Antigen deficient *F. tularensis*, and O-Antigen-deficient *F. tularensis* LVS strain; *L. monocytogenes*; and adenovirus.

The disclosure also provides a method of protecting a susceptible host against an infection of *F. tularensis* comprising administering to said host an amount of the immunoprotective composition of the disclosure sufficient to invoke an immunoprotective response in the host.

The disclosure further provides a recombinant attenuated *L. monocytogenes* comprising a polynucleotide encoding at least one extracellular or immunogenic protein, or fragment thereof, of *F. tularensis* that induces a protective immunity against *F. tularensis*. In one aspect, the extracellular or immunogenic protein or fragment *F. tularensis* is selected from the group consisting of AcpA, Bfr, DnaK, FabD, GroEL, IglC, KatG, Pld, Tul4, SodB and any combination thereof.

The disclosure provides a recombinant attenuated viral vector comprising a polynucleotide encoding at least one extracellular or immunogenic protein, or fragment thereof, of *F. tularensis* that induces a protective immunity against *F. tularensis*. In one aspect, the extracellular or immunogenic protein or fragment *F. tularensis* is selected from the group consisting of AcpA, Bfr, DnaK, FabD, GroEL, IglC, KatG, Pld, Tul4, SodB and any combination thereof. In another aspect, the viral vector is an adenoviral vector.

The disclosure also provides a method of immunization comprising administering a prime-boost combination to a subject, wherein the prime vaccine comprises at least one attenuated vector expressing at least one *F. tularensis* antigen selected from the group consisting of acpA, Bfr, DnaK, fabD, groEL, iglC, katG, Pld, Tul4 and sodB, and wherein the boost vaccine comprises at least one attenuated vector comprising at least one *F. tularensis* antigen selected from the group consisting of AcpA, Bfr, DnaK, FabD, GroEL, IglC, KatG, Pld, Tul4 and SodB. In one aspect, the prime vaccine comprises an IglC antigen and a KatG antigen and the boost vaccine comprises an IglC antigen and a KatG antigen. In another aspect, the prime vaccine comprises *L. monocytogenes* and the boost vaccine comprises an adenovirus. In yet another aspect, the prime vaccine is an adenovirus and the boost vaccine is *L. monocytogenes*.

BRIEF DESCRIPTION OF THE FIGURES

FIG. 7 shows sequence of the disclosure.

DETAILED DESCRIPTION

Figure 1:
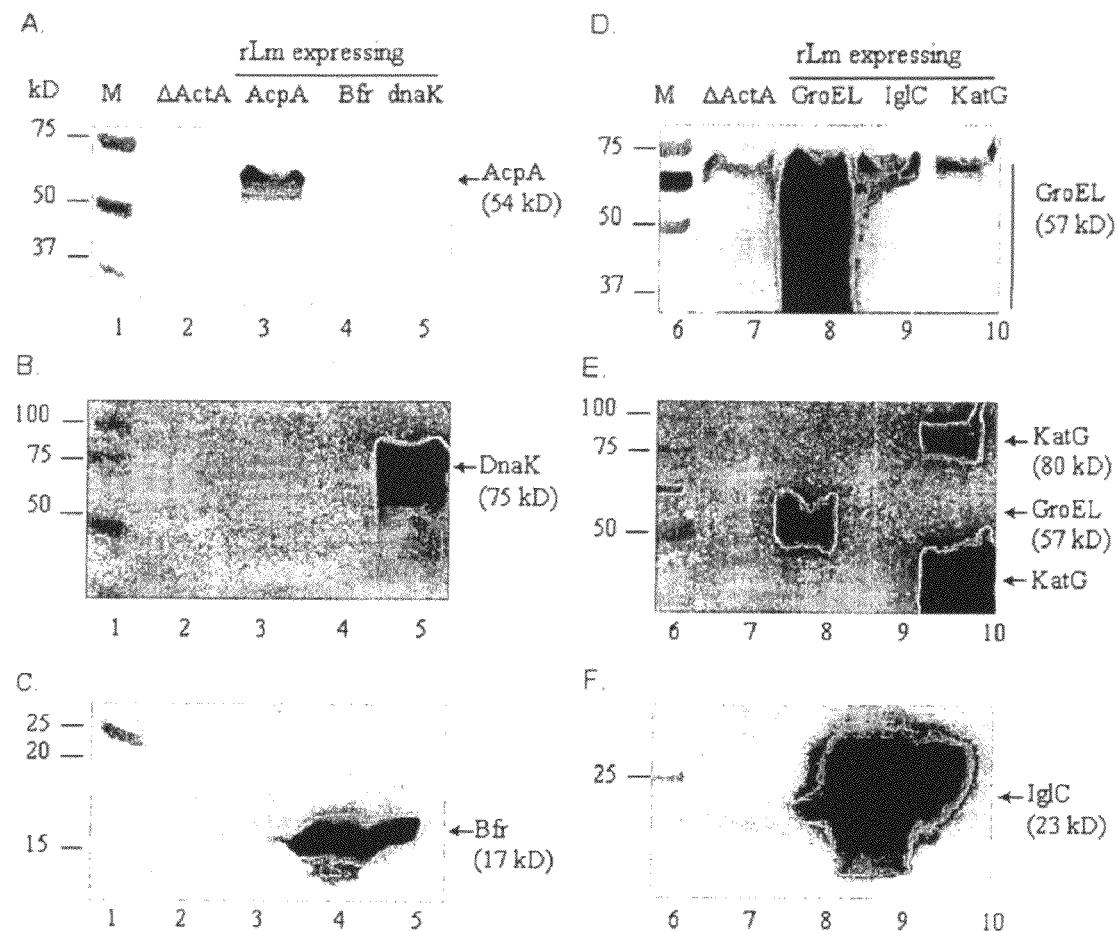
FIG. 1 shows expression of *F. tularensis* proteins by attenuated recombinant *L. monocytogenes*. Culture filtrates of each of the attenuated recombinant *L. monocytogenes* (rLM) strains were concentrated and a volume of filtrate equivalent to 1 ml of the bacterial culture was analyzed by Western blotting using rabbit polyclonal antibody to AcpA (A), Bfr (C), KatG (D), or IglC (F). The membranes for A and D were stripped and reprobed with rabbit polyclonal antibody to DnaK (B) and KatG (E), respectively. Lane 1, molecular mass standards; lane 2, filtrate of parental *L. monocytogenes* with a deletion in actA; lane 3, filtrate of *L. monocytogenes* expressing AcpA; lane 4, filtrate of *L. monocytogenes* expressing Bfr; lane 5, filtrate of *L. monocytogenes* expressing DnaK; lane 6, molecular mass standards; lane 7, filtrate of parental *L. monocytogenes* with a deletion in actA; lane 8, filtrate of *L. monocytogenes* expressing GroEL; lane 9, filtrate of *L. monocytogenes* expressing IglC; and lane 10, filtrate of *L. monocytogenes* expressing KatG. On the right border of each blot are listed the proteins of interest and their mass.

The exemplary descriptions provided herein are exemplary and explanatory only and are not restrictive of the invention, as claimed. Moreover, the disclosure is not limited to the particular embodiments described, as such may, of course, vary. Further, the terminology used to describe particular embodiments is not intended to be limiting.

With respect to ranges of values, the disclosure encompasses each intervening value between the upper and lower limits of the range to at least a tenth of the lower limit's unit, unless the context clearly indicates otherwise. Further, the disclosure encompasses any other stated intervening values. Moreover, the disclosure also encompasses ranges excluding either or both of the upper and lower limits of the range, unless specifically excluded from the stated range.

Unless defined otherwise, the meanings of all technical and scientific terms used herein are those commonly understood by one of ordinary skill in the art to which this disclosure belongs. One of ordinary skill in the art will also appreciate that any methods and materials similar or equivalent to those described herein can also be used to practice or test the disclosure. Further, all publications mentioned herein are incorporated by reference.

It must be noted that, as used herein and in the appended claims, the singular forms "a," "or," and "the" include plural referents unless the context clearly dictates otherwise. Thus, for example, reference to "a subject polypeptide" includes a plurality of such polypeptides and reference to "the agent" includes reference to one or more agents and equivalents thereof and so forth.

*Francisella tularensis* is a Category A bioterrorism agent that has previously been stock-piled as a germ-warfare agent and may have been used as such in World War II. Especially when spread by the air-borne route, *F. tularensis* can cause a highly fatal pneumonia.

*F. tularensis* is a nonmotile, nonsporulating, gram-negative coccobacillus that causes zoonotic disease in small animals such as rodents, rabbits, and beavers. Humans typically acquire tularemia by handling infected animals, by consumption of contaminated food or water, or by the bite of blood-sucking insects. *F. tularensis* consists of three main subspecies—*tularensis, holarctica*, and *mediasiatica*—which differ in their geographic distributions and in their virulence in humans. *F. tularensis* subspecies *tularensis*, found almost exclusively in North America, is highly virulent for humans. As few as 10 organisms delivered subcutaneously or 25 organisms delivered by inhalation can lead to a severe, potentially lethal, infection in humans. *F. tularensis* subspecies *holarctica* (found in North America and in Europe) and subspecies *mediasiatica* (found in Asia) are of lower virulence. Because of its high infectivity and capacity to cause severe morbidity and mortality, *F. tularensis* subspecies *tularensis* is classified as a category A potential agent of bioterrorism.

This disclosure provides vaccine antigens and vectors useful for providing protective immunity. This disclosure is based, in part, upon the identification of antigen and virulence factors present in the virulent strain tularemia compared with an attenuated LVS.

Thirteen major extracellular proteins released by the attenuated LVS and fully virulent *F. tularensis* RCI were identified. Among the major extracellular proteins identified, important differences were observed between LVS and RCI in 2-D electrophoresis profiles for 3 of these proteins—KatG, DnaK, and Bfr.

KatG and DnaK were more abundant in the RCI culture filtrate whereas Bfr was more abundant in the LVS culture filtrate. Interestingly, for both strains, there was a ~4-fold increase in the abundance of KatG in the culture filtrate as the cultures grew from 4 h to 14 h. The more abundant KatG in the culture filtrate of *F. tularensis* RCI observed at these two time points may be due to the combination of a higher production and a higher rate of export of the protein. In one experiment, catalase activity and total bacterial protein was assayed in the culture filtrate and the pellet of *F. tularensis* cultures harvested at the 14 h time point (optical density of the culture was 2.4 for RCI and 0.7 for LVS). Catalase enzymatic activity found in the bacterial pellet was 8-fold higher for RCI (i.e., RCI:LVS=8:1), while the total amount of bacterial protein in the pellet was only 3.2-fold higher for RCI. At the same time the catalase activity in the culture filtrate was 14-fold higher for RCI than for LVS, whereas the total amount of bacterial protein in the culture filtrate was only a 1.5-fold higher for RCI than for LVS. Normalizing for total bacterial protein, the RCI strain had 2.5 fold more catalase activity in the bacterial pellet and 9.3 fold more catalase activity in the culture filtrate than the LVS strain. KatG is the most abundant protein released by *F. tularensis* RCI. Both the amount of KatG released into culture filtrate and the abundance relative to other proteins is significantly less for *F. tularensis* LVS than for *F. tularensis* RCI.

Catalase-peroxidase is a bifunctional enzyme exhibiting both catalase and broad spectrum peroxidase activities. It contains a heme prosthetic group and catalyzes a multistep oxidation reaction involving hydrogen peroxide as the electron acceptor. KatG of *F. tularensis* is phylogenetically closest to that of *Yersinia pestis* (accession number AF135170) and *L. pneumophila* (accession number AF276752) both with 58% identity and 72% similarity and to that encoded on a plasmid in *E. coli* (O157:H7) (accession number X89017) with 56% identity and 72% similarity. In addition to their apparent sequence homology, the catalase-peroxidase of each of these 4 bacterial species includes a signal peptide as a unique feature, absent from other known members of the catalase-peroxidase subfamily and are probably exported via a sec-dependent pathway. The analysis of the cytosol extract from streptolysin-O permeabilized macrophages demonstrates that KatG is secreted by *F. tularensis* growing intracellularly in macrophages. KatG is located at the periphery of the bacteria, consistent with a periplasmic distribution in addition to being secreted away from the bacterium.

*L. pneumophila* produces two catalase-peroxidases, KatA and KatB. Whereas KatB is located exclusively in the bacterial cytosol, KatA possesses a signal peptide and is present in the periplasm of the bacterium. Amemura-Maekawa and co-workers proposed that the periplasmic catalase-peroxidase (KatA) protects *L. pneumophila* from oxidative stresses by inactivating the hydrogen peroxide converted from superoxide radicals by the action of SodC, a Cu—Zn-SOD which is usually located in bacterial periplasm. Gene mutation experiments demonstrated that phagosomes containing *L. pneumophila* katA or katB mutant exhibited a higher frequency of co-localization with LAMP-1 and the bacterial mutants showed a defective intracellular multiplication in primary macrophages and amoebae. *F. tularensis* and *L. pneumophila* are both intracellular pathogens that must defend against host oxidative stress. KatG of *F. tularensis* plays a role equivalent to KatA in *L. pneumophila* and contributes to the pathogenesis and intracellular life style of *F. tularensis*. At present, KatG is the only catalase-peroxidase identified in the *F. tularensis* Schu 4 genome. This disclosure identifies KatG as a virulence factor, in addition, KatG serves as an antigen.

Bfr, DnaK, FabD, GroEL, and SodB proteins identified in the early culture filtrates possess no predictable signal peptide and, based on their potential physiological function, these proteins are likely to have a major presence in the bacterial cytosol. Nevertheless, the disclosure shows that these proteins are released early into the culture filtrate by actively growing bacteria. The protein AcpA is not identified among the 12 most abundant proteins in early culture filtrate, but it contains a highly probable signal peptide (from amino acid residues #1 to #21) and therefore is expected to be exported and available for antigen processing and presentation. The protein Tul4 was not identified among the 12 most abundant proteins in early culture filtrate, but it has a lipoprotein signal peptide that leads to exportation and lipid modification of the polypeptide. As predicted by the LipoP sequence analysis and prediction server (http: ~www~cbs.dtu.dk/services/LipoP, the mature Tul4 starts at amino acid residue #20 (i.e. the first 5 amino acids are CSTLG) and is a lipoprotein (lipid modification on the first residue "cysteine" of the mature protein). Because of this Tul4 is expected to be located on the bacterial cell envelope. Shedding of fragments of bacterial envelope will make this protein available for antigen processing and presentation. The protein IglC and Pld have no apparent signal peptides and are not identified among the 12 most abundant proteins in the early culture filtrate. However, IglC has been shown to be up-regulated during infection of macrophages and is essential to bacterial virulence. Phospholipase D is an enzyme that is likely to be important in degradation of host cell phosophodiester and therefore is likely to play an important role in virulence.

Accumulated evidence has shown that in addition to their intracellular role, some cytosolic proteins are released and function on the bacterial surface as receptors. Glyceraldehyde-3-phosphate dehydrogenase is a protein of multiple functions. It is the major transferrin-binding protein in the cell wall of staphylococci. It is also identified as a major surface protein in group A streptococci that is capable of binding fibronectin, plasminogen, lysozyme, and actin. In addition, GAPDH and DnaK of *Listeria monocytogenes* are present in the cell wall and show strong binding affinity to plasminogen. Export of GroEL has been reported previously for *Bartonella bacilliformis, Helicobacter pylori*, and *L. pneumophila*. In the case of *H. pylori* and *L. pneumophila* the exported GroEL may mediate gastric colonization and adherence to HeLa cells, respectively. Analysis of the cytosol of *F. tularensis*-infected macrophages demonstrated that KatG and GroEL were released into the host cell cytosol. These proteins would thus be expected to be available for processing and presentation by the host cell. Consistent with this, T cells from LVS-infected mice proliferated strongly and released IFN-γ in response to these proteins.

Bacterioferrin (Bfr) of *F. tularensis* RCI exhibits a moderate homology of approximately 21% identity and 44% similarity to that of *Brucella melitensis* (accession number P49944) and a strict anaerobe *Desulfovibrio desulfuricans* (accession number Q93PP9). In the cases studied, bacterioferritin assembles as a spherical protein shell of 24 subunits with 12 haem-b prosthetic groups between subunit pairs surrounding a central non-heme iron-storage cavity. Bacterioferritin acts as an iron storage protein and may play a role in protection against cell-damaging free radicals generated from oxygen in the presence of free iron. *F. tularensis* LVS and RCI each have multiple Bfr isoforms. Among these various Bfr isoforms, the most abundant LVS isoform is absent from the RCI culture filtrate. Similarly, a Bfr protein spot unique to *F. tularensis* subspecies *holarctica* was recently reported in a comparative proteome analysis of the bacterial cell lysates from *F. tularensis* subspecies *holarctica* and *tularensis*. T cells also respond strongly to Bfr.

The disclosure identifies *F. tularensis* proteins that are present in abundance in the culture filtrate and demonstrated that mice infected with *F. tularensis* LVS develop a significant cell-mediated immune response to these culture filtrate proteins. The successful expression and purification of these proteins in soluble form will enable one to continue studies of the host immune response to these proteins and their vaccine potential. It is particularly noteworthy that KatG is secreted in abundance by the fully virulent *F. tularensis* but is secreted at a lower level by the attenuated LVS. It is possible that a vaccine utilizing this protein will have advantages over the LVS in conferring protection against virulent *F. tularensis*.

Intracellular pathogens follow one of three general pathways within a host cell: (a) the extraphagosomal pathway, in which the pathogen lyses the phagosomal membrane and resides freely in the host cell cytoplasm, (b) the phagolysosomal pathway, in which the pathogen resides and multiplies in an acidified phagosome that does fuse with lysosomes, and (c) a phagosomal pathway in which the pathogen resides in a phagosome that does not fuse with lysosomes. Examples of intracellular pathogens that have been reported to follow the extraphagosomal pathway by lysing their phagosome include *T. cruzi, Listeria monocytogenes, Shigellae*, and some species of *Rickettsia*. Examples of pathogens that reside in acidified phagolysosomes include *Coxiella burnetii* and *Leishmania amazonensis*. Pathogens that have been shown to reside in phagosomes that do not fuse with lysosomes at various points in their life cycle in macrophages include *Legionella pneumophila, Chlamydia psittaci*, and *M. tuberculosis*. Within these three general pathways, individual parasites exhibit additional unique variations that can be distinguished ultrastructurally and in terms of the interactions of the parasite or its vacuole with other host cell organelles and the membrane trafficking within the host cell. These unique variations that characterize the intracellular compartment and its host cell interactions provide the fundamental basis for understanding the cell biology and pathogenetic mechanisms of intracellular parasites.

The disclosure demonstrates that both the attenuated LVS strain (i.e., an attenuated form of *Francisella tularensis* subspecies *holarctica*, a much less virulent subspecies) and a virulent recent clinical isolate of *F. tularensis* subspecies *tularensis* transiently reside in a non-acidified phagosome with abundant staining for LAMPs but with little or no staining for cathepsin D. The phagosomal membranes acquire a densely staining fibrillar coating on their cytoplasmic side and subsequently undergo budding, vesiculation, and morphological disruption, giving the bacteria free access to the cytoplasm.

Although *F. tularensis* can be grown in the laboratory on enriched culture media, *F. tularensis* bacteria invade and grow productively in macrophages. It is thought that, in natural infections, the bacterium replicates intracellularly within host mononuclear phagocytes. After entry of the organism into the macrophages, *F. tularensis* initially resides in a phagosome. However, the bacterium arrests the maturation of its phagosome, and subsequently, it escapes the phagosome to the cytoplasm.

There are two arms to the immune response: a humoral (antibody) response and a cell-mediated response. Protein antigens derived from pathogens (viruses and some bacteria) that replicate intracellularly within the cytoplasm (i.e., extraphagosomally) are processed within the infected host cell releasing short peptides which are subsequently displayed on the infected cell surface in association with class I major histocompatability (MHC I) molecules. When this associated complex of MHC I and peptide is contacted by antigen-specific CD8+ T-cells the T-cell is activated, acquiring cytotoxic activity. These cytotoxic T-cells (CTLs) can lyse infected host cells, so limiting the replication and spread of the infecting pathogen. Another important arm of the immune response is controlled by CD4+ T-cells. When antigen derived from pathogens is released into phagosomes of infected host cells, they may be processed and subsequently displayed on the surface of the infected cell in association with MHC class II molecules. When this associated complex of MHCII and peptide is contacted by antigen-specific CD4+ T-cells, the T cells are activated. These activated T cells can secrete cytokines that activate host cells of the pathogen, allowing the host cells to exert an anti-microbial effect against the pathogen, e.g. killing it or limiting its replication. Antigen can also be presented to T cells via cross-priming. In this case, antigens are released by infected host cells, e.g. by host cells undergoing apoptosis, and the antigens are taken up by specialized antigen presenting cells for subsequent presentation to T cells including CD4+ and CD8+ T cells. Recognition of antigen in association with MHC class II molecules stimulates CD4+ T-cells to secrete soluble factors (cytokines) which regulate the effector mechanisms of other T-cells. Antibody is produced by B-cells. Binding of antigen to secreted antibody may neutralize the infectivity of a pathogen and binding of antigen to membrane-bound antibody on the surface of B-cells stimulates division of the B-cell so amplifying the B-cell response. In general, both antibody and cell-mediated immune responses (CD8+ and CD4+) help to control infections.

"CD8+ T cells" represent a class of T lymphocytes characterized by the possession of the CD8 cell surface marker. CD8+ T cells are MHC Class I-restricted "CTLs" or "suppressor T cells."

"CD4+ T cells" represent a class of T lymphocytes characterized by the possession of the CD4 cell surface marker. CD4+ T cells are MHC Class II-restricted T lymphocytes. There are two types of CD4+ T cells referred to as type 1 or type 2 "helper T cells."

The driving force behind the development of these two types of immune responses is cytokines, a number of identified protein messengers which serve to help the cells of the immune system and steer the eventual immune response to either a Th1 or Th2 response. Thus, high levels of Th1-type cytokines tend to favor the induction of cell mediated immune responses to the given antigen, while high levels of Th2-type cytokines tend to favor the induction of humoral immune responses to the antigen. It is important to remember that the distinction of Th1 and Th2-type immune responses is not absolute. In reality, an individual will support an immune response which is described as being predominantly Th1 or predominantly Th2. Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of IL-4, IL-5, IL-6, IL-10 and tumor necrosis factor-β (TNF-β).

The disclosure provides polynucleotides, polypeptide, vectors and attenuated vectors useful for generating protective immunity to *F. tularensis*. A polynucleotide of the disclosure encodes an antigenic polypeptide or fragment thereof that, when expressed, provides an immunogenic response. The polynucleotide can be delivered directly or via an attenuated vector. In another aspect, a polypeptide that induces an antigenic response can be used to immunize a subject.

A "polynucleotide" generally refers to any polyribonucleotide (RNA) or polydeoxyribonucleotide (DNA), which may be unmodified or modified RNA or DNA. Polynucleotides include, without limitation, single-stranded and double-stranded DNA, DNA that is a mixture of single-stranded and double-stranded regions, single-stranded and double-stranded RNA, and RNA that is a mixture of single-stranded and double-stranded regions. Polynucleotides also include hybrid molecules comprising DNA and RNA that may be single-stranded or, more typically, double-stranded or a mixture of single-stranded and double-stranded regions. In addition, "polynucleotide" refers to triple-stranded regions comprising RNA or DNA or both RNA and DNA. Polynucleotides also include DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. Oligonucleotides are relatively short polynucleotides.

A "polypeptide" refers to any polypeptide comprising two or more amino acids joined to each other by peptide bonds or modified peptide bonds. "Polypeptide" refers to both short chains, commonly referred to as peptides, oligopeptides or oligomers, and to longer chains. Polypeptides may contain amino acids other than those normally encoded by a codon.

Polypeptides include amino acid sequences modified either by natural processes, such as post-translational processing, or by chemical modification techniques that are known in the art. Modifications may occur anywhere in a polypeptide, including the peptide backbone, the amino acid side-chains and the amino or carboxyl termini. Such modifications may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The disclosure provides *F. tularensis* antigens that are immunoprotective. Such antigens can be delivered in a number of ways to the host so as to stimulate a protective immune response against *F. tularensis*. *F. tularensis* antigens useful in the methods and compositions of the disclosure comprise a polypeptide selected from the group consisting of AcpA, Bfr, DnaK, FabD, GroEL, IglC, KatG, Pld, Tul4, and SodB or any fragment thereof. A polypeptide can be used alone or in combination with other polypeptide antigens or adjuvants. In addition, the methods and compositions of the disclosure comprise a polynucleotide or a fragment thereof encoding a AcpA, Bfr, DnaK, FabD, GroEL, IglC, KatG, Pld, Tul4, and SodB or fragments thereof. Examples of polynucleotides encoding *F. tularensis* antigens of the disclosure are set forth in SEQ ID NOs: 1, 3, 5, 7, 9, 11, 13, 15, 17 and 19 (or fragments thereof encoding antigenic epitopes). Examples of polypeptides useful in the methods and compositions of the disclosure comprise the *F. tularensis* polypeptides set forth in SEQ ID Nos: 2, 4, 6, 8, 10, 12, 14, 16, 18, 20 or fragments thereof.

An "antigen" is a substance capable of generating an immune response in a subject exposed to the antigen. Antigens are usually polypeptides and are the focus of the host's immune response. An "epitope" or "antigenic determinant" is that part of an antigen to which T cells and antibodies specifically bind. An antigen may contain multiple epitopes. Antigens of the disclosure comprise *F. tularensis* extracellular or immunogenic polypeptides. In specific aspect, the *F. tularensis* polypeptides comprise AcpA, Bfr, DnaK, FabD, GroEL, IglC, KatG, Pld, SodB, and Tul4 (SEQ ID NOs: 2, 4, 6, 8, 10, 12, 14, 16, 18, and 20 respectively).

A "vaccine" as used herein refers to a composition comprising a molecule, vector, or organism that, when administered to a subject, induces an immune response. Vaccines can comprise polynucleotide molecules, polypeptide molecules, and carbohydrate molecules, as well as derivatives and combinations of each, such as glycoproteins, lipoproteins, carbohydrate-protein conjugates, fusions between two or more polypeptides or polynucleotides, and the like. A vaccine may further comprise a diluent, an adjuvant, a carrier, or combinations thereof, as would be readily understood by those in the art.

A vaccine may be comprised of separate components. As used herein, "separate components" refers to a situation wherein the term vaccine comprises two discrete vaccines to be administered separately to a subject. In that sense, a vaccine comprised of separate components may be viewed as a kit or a package comprising separate vaccine components. For example, in the context of the disclosure, a package may comprise a first immunogenic composition comprising an attenuated bacterial vector and a second immunogenic composition comprising an attenuated viral vector comprising the same or different *F. tularensis* antigens (e.g., AcpA, Bfr, DnaK, FabD, GroEL, IglC, KatG, Pld, Tul4 and SodB).

A vaccine "induces" an immune response when the antigen or antigens present in the vaccine cause the vaccinated subject to mount an immune response to that antigen or antigens. The vaccinated subject will generate an immune response, as evidenced by activation of the immune system, which includes the production of vaccine antigen-specific T cells, vaccine antigen-specific B cells, vaccine antigen-specific antibodies, and cytokines. The resulting immune response may be measured by several methods including ELISPOT, ELISA, chromium release assays, intracellular cytokine staining, FACS analysis, and MHC tetramer staining (to identify peptide-specific cells). A skilled artisan may also use these methods to measure a primary immune response or a secondary immune response.

The antigens can be delivered via an attenuated vector comprising a polynucleotide encoding an antigenic polypeptide of *F. tularensis* that results in presentation of the encoded polypeptide via MHC class I or MHC class II. Examples of attenuated vectors useful in the disclosure include *L. monocytogenes*, *F. tularensis*, *F. tularensis* lacking a functional O-Antigen, *F. tularensis* Live Vaccine Strain (LVS), *F. tularensis* LVS lacking a functional O-Antigen, or another attenuated bacterial vector such as *Mycobacterium bovis* BCG, *Shigela flexneri* and *Escherichia coli*. The term "attenuated," when used with respect to a bacteria, means that the bacteria has lost some or all of its ability to proliferate and/or cause disease or other adverse effect when the bacteria infects an organism. For example, an "attenuated" bacteria can be unable to replicate at all, or be limited to one or a few rounds of replication, when present in an organism in which a wild-type or other pathogenic version of the attenuated bacteria can replicate. Alternatively or additionally, an "attenuated" bacteria might have one or more mutations in a gene or genes (e.g., encoding a functional O-antigen) that are involved in pathogenicity of the bacteria. Many genes, loci, or operons are known, mutations in which will result in an attenuated bacteria. Examples of attenuated bacteria used as live vaccines include *S. typhi* carrying a mutation in its galE or htrA gene, and *V. cholerae* carrying mutations in its ctxA gene. For example, the recombinant *Listeria monocytogenes* strains expressing *F. tularensis* IglC and KatG (rLM/IglC or rLM/KatG) were demonstrated to protect against aerosol challenge with the highly virulent Type A *F. tularensis* subspecies *tularensis* Schu4 Strain.

Microorganisms which are used to express an *F. tularensis* antigen for use in immunoprotective compositions include, without limitation, *Campylobacter* sp., *Yersinia* sp., *Helicobacter* sp., *Gastrospirillum* sp., *Bacteroides* sp., *Klebsiella* sp., *Lactobacillis* sp., *Streptococcus gordonii*, *Enterobacter* sp., *Salmonella* sp., *Shigella* sp., *Aeromonas* sp., *Vibrio* sp., *Clostridium* sp., *Enterococcus* sp. and *Escherichia coli* (see e.g. U.S. Pat. Nos. 5,858,352, and 6,051,416, and Levine et al., in "New Generation Vaccines Second Edition" ed. Levine et al., Marcel Dekker, Inc. pp 351-361 (1997), Levine et al., in "New Generation Vaccines Second Edition" ed. Levine et al., Marcel Dekker, Inc. pp 437-446 (1997), Butterton et al., in "New Generation Vaccines Second Edition" ed. Levine et al., Marcel Dekker, Inc. pp 379-385 (1997) and Fennelly et al., in "New Generation Vaccines Second Edition" ed. Levine et al., Marcel Dekker, Inc. pp 363-377 (1997)). For example, *Campylobacter jejuni*, *Campylobacter coli*, *Listeria monocytogenes*, *Yersinia enterocolitica*, *Yersinia pestis*, *Yersinia pseudotuberculosis*, *Escherichia coli*, *Shigella flexneri*, *Shigella sonnei*, *Shigella dysenteriae*, *Shigella boydii*, *Helicobacter pylori*, *Helicobacter fells*, *Gastrospirillum hominus*, *Vibrio cholerae*, *Vibrio parahaemolyticus*, *Vibrio vulnificus*, *Bacteroides fragilis*, *Clostridium difficile*, *Salmonella typhimurium*, *Salmonella typhi*, *Salmonella gallinarum*, *Salmonella pullorum*, *Salmonella choleraesuis*, *Salmonella enteritidis*, *Klebsiella pneumoniae*, *Enterobacter cloacae*, and *Enterococcus faecalis*. *Escherichia coli* include but are not limited to entero-toxic, entero-hemorrhagic, entero-invasive, entero-pathogenic or other strains can be used in the disclosure.

The disclosure also provides an immunogenic composition and vaccine that uses an antigen delivery method that deliveries *F. tularensis* immunogenic antigens in a manner that is similar to delivery in a natural infection. *F. tularensis* antigens are delivered in one or more vectors capable of inducing presentation via Major Histocompatability Complex (MHC) I.

In one aspect, the disclosure provides an immunogenic composition and vaccine that utilize a live attenuated recombinant *Listeria monocytogenes* vector to deliver *F. tularensis* immunogenic antigens. A rationale for using live attenuated *L. monocytogenes* as a vector is the similarity in the infective process between *L. monocytogenes* and *F. tularensis* (other attenuated bacterial vectors having a similar infective process can be used). Like *F. tularensis*, *L. monocytogenes* is an intracellular bacterium that resides in host mononuclear phagocytes. Importantly, *L. monocytogenes* escapes the phagosome in which it initially resides and subsequently inhabits the cytoplasm of the host cell. *F. tularensis* also escapes the phagosome and resides in the cytoplasm of the host cell. Thus, *F. tularensis* releases potentially immunoprotective antigens into the host cell cytoplasm, after which they are processed and presented to the immune system. Such antigens are presented to the immune system via MHC class I molecules, resulting in the priming of CD8 T-cells. When *L. monocytogenes* is utilized as a vector for the release of *F. tularensis* immunogenic antigens, the antigens are processed and presented in a way that mimics their processing and presentation by *F. tularensis* and thereby stimulate an immunoprotective response. In another aspect, an attenuated *F. tularensis* lacking a wild-type O-antigen is used. In another aspect, the attenuated *F. tularensis* LVS strain is used.

The disclosure provides a live attenuated *Listeria monocytogenes* and *F. tularensis* vectors useful for inducing immune reactions in a subject directed to a target antigen. In one aspect, the disclosure provides a live attenuated *Listeria monocytogenes* expressing *F. tularensis* polypeptide antigens. For example, the disclosure provides the following live attenuated *L. monocytogenes* recombinant vaccines:

(a) *L. monocytogenes* expressing *F. tularensis* IglC;
(b) *L. monocytogenes* expressing *F. tularensis* KatG;
(c) *L. monocytogenes* expressing *F. tularensis* AcpA;
(d) *L. monocytogenes* expressing *F. tularensis* Bfr;
(e) *L. monocytogenes* expressing *F. tularensis* GroEL;
(f) *L. monocytogenes* expressing *F. tularensis* Pld; and
(g) *L. monocytogenes* expressing *F. tularensis* DnaK.

The disclosure provides the following live attenuated *F. tularensis* recombinant vaccines:

(a) *F. tularensis* LVS expressing AcpA (rFtLVS/AcpA);
(b) *F. tularensis* LVS expressing Bfr (rFtLVS/Bfr);
(c) *F. tularensis* LVS expressing DnaK (rFtLVS/DnaK);
(d) *F. tularensis* LVS expressing GroEL (rFtLVS/GroEL);
(e) *F. tularensis* LVS expressing IglC (rFtLVS/IglC);
(f) O-antigen-deficient *F. tularensis* LVS (rFtLVSΔOAg); and
(g) O-antigen-deficient *F. tularensis* LVS expressing IglC (rFtLVSΔOAg/IglC).

In one aspect, the *F. tularensis* LVS vector over-expresses the antigenic polypeptide. In another aspect, the *F. tularensis* lacks a functional O-antigen.

Alternatively, or in addition to, a non-bacterial attenuated vector such as a replication-deficient viral vector may be used in the methods and compositions of the disclosure. Such viral vectors useful in the methods and compositions of the disclosure include, but are not limited to, Vaccinia, Avipox, Adenovirus, AAV, Vaccinia virus NYVAC, Modified vaccinia strain Ankara (MVA), Semliki Forest virus, Venezuelan equine encephalitis virus, and herpes viruses. Gene transfer techniques using these viruses are known to those skilled in the art. Retrovirus vectors, for example, may be used to stably integrate the polynucleotide of the disclosure into the host genome. Replication-defective adenovirus vectors by contrast remain episomal and therefore allow transient expression. In a specific embodiment, the adenovirus used as a live vector is a replication defective human or simian adenovirus. Typically these viruses contain at least an E1 deletion and may be grown on cell lines that are transformed with an E1 gene. Suitable Simian adenoviruses are, for example, viruses isolated from Chimpanzee. Examples of viruses suitable for use in the disclosure include C68 (also known as Pan 9) (U.S. Pat. No. 6,083,716, incorporated herein by reference) and Pan 5, 6 and Pan 7 (WO 03/046124 incorporated herein by reference). Thus, these vectors can be manipulated to insert a heterologous polynucleotide coding for an antigen such that the product is expressed. The use formulation and manufacture of such recombinant adenoviral vectors is set forth in detail in WO 03/046142, which is incorporated by reference. Naked DNA vectors can also be used in addition to antigenic proteins alone or in combination with an adjuvant.

In one aspect, the disclosure provides a replication-deficient adenovirus expressing *F. tularensis* polypeptide antigens. For example, the disclosure provides:

(a) Replication-deficient adenovirus serotype 5 expressing *F. tularensis*, KatG, AdvΔE1E3/Ft KatG;
(b) Replication-deficient adenovirus serotype 5 expressing *F. tularensis* IglC, AdvΔE1E3/Ft IglC;
(c) Replication-deficient adenovirus serotype 5 expressing *F. tularensis* KatG and IglC, AdvΔE1E3/Ft KatG-IglC;
(d) Replication-deficient adenovirus serotype 5 expressing *F. tularensis* IglC and katG, AdvΔE1E3/Ft IglC-katG; and In addition, the disclosure envisions immunization utilizing a homologous or heterologous prime-boost vaccination strategy. The heterologous strategy may include priming with one vector, e.g. *L. monocytogenes* expressing one or more proteins, and boosting with another vector, e.g., adenovirus expressing the same protein or proteins, or vice versa. Boosting may also include immunizing with an *F. tularensis* protein or proteins or fragments thereof in an adjuvant. The specific examples provided herein demonstrate the delivery of the antigens to an animal host utilizing various vaccination strategies and the resulting immunoprotection against *F. tularensis* challenge.

The strains provided herein allow broadening of the approach to vaccination against tularemia in a number of ways. First, each of the vaccines could be used individually in a homologous vaccination protocol, e.g. vaccinating two or three times with the individual vaccines at intervals of time. Second, the vaccines could be used in combination with the other vaccines in a heterologous prime-boost vaccination protocol. For example, one can prime with one of the *F. tularensis* based vaccines and boost with a recombinant *Listeria monocytogenes* vaccine or recombinant adenovirus vaccine. A few examples of heterologous prime-boost vaccination strategies that can be employed are provided in Table 1 below:

TABLE 1

| Prime | Boost |
|---|---|
| FtLVSΔOAg | rLM/IglC and/or rLM/KatG and/or rLM/Tul4 and/or rLM/AcpA and/or rLM/Bfr and/or rLM/GroEL and/or rLM/Pld and/or rLM/DnaK |
| FtLVSΔOAg | rAdv/IglC and/or rAdv/KatG or rAdv/IglC-KatG or rAdv/KatG-IglC |
| rFtLVSΔOAg/IglC | rLM/IglC |
| rFtLVS/AcpA | rLM/AcpA |
| rFtLVS/Bfr | rLM/Bfr |
| rFtLVS/DnaK | rLM/DnaK |
| rFtLVS/GroEL | rLM/GroEL |
| rFtLVS/IglC | rLM/IglC |
| rLM/Tul4 | rAdv/Tul4 |
| rLM/IglC | rAdv/IglC |
| rLM/KatG | rAdv/KatG |
| rLM/IglC and rLM/KatG | rAdv/IglC-KatG or rAdv/KatG-IglC |
| rFtLVSΔOAg/IglC | rAdv/IglC |
| rLM/IglC and/or rLM/KatG and/or rLM/Tul4 and/or rLM/AcpA and/or rLM/Bfr and/or rLM/GroEL and/or rLM/Pld and/or rLM/DnaK | The purified protein(s) expressed by the prime vaccine in a suitable carrier with a suitable adjuvant |
| rFtLVSΔOAg/IglC | IglC in a suitable carrier with a suitable adjuvant |
| rFtLVS/IglC | IglC in a suitable carrier with a suitable adjuvant |
| rFtLVS/AcpA and/or rFtLVS/Bfr and/or rFtLVS/DnaK and/or rFtLVS/GroEL | AcpA and/or Bfr and/or DnaK and/or GroEL a suitable carrier with a suitable adjuvant |

The disclosure thus provides several types of vaccines. One group of vaccines consists of attenuated *L. monocytogenes* expressing one or more *F. tularensis* antigens. Another group of vaccines consists of attenuated *F. tularensis* expressing or overexpressing one or more *F. tularensis* antigens. Other vaccines of the disclosure comprise *F. tularensis* antigens in a suitable adjuvant. Another group of vaccines of the disclosure comprise a viral vector (e.g., adenovirus) expressing one or more *F. tularensis* antigens.

Each vaccine is administered, e.g. intradermally, subcutaneously, intramuscularly, intranasally, inhaled, or even orally to a mammalian host. The vaccine can be administered as part of a homologous or heterologous prime-boost strategy. The vaccine induces a strong cell-mediated immune response to pathogen antigens in the vaccine. Most importantly, the vaccine protects the mammalian hosts against infection with *F. tularensis*.

The priming vaccine used in the method of the disclosure comprises an *F. tularensis* antigen (e.g., IglC as the prime vaccine). The priming vaccine may be an antigenic epitope of an *F. tularensis* antigen, the full-length antigen, a vector comprising a polynucleotide encoding the antigen and the like. In one aspect, the priming vaccine comprises a polynucleotide encoding an antigen under control of a foreign promoter within a bacterium or virus. The polynucleotide of the priming vaccine is present in a suitable delivery vector such as a plasmid or other vector such as a bacterial or viral vector. The polynucleotide may be under the control of a suitable promoter such as a promoter derived from the HCMV IE gene. The priming vaccine is administered in an amount effective for priming an immune response to the *F. tularensis* antigen. As used herein, "priming" of an immune response occurs when an antigen is presented to T cells or B cells. As a result, primed cells can respond to the same antigen again as memory cells in a second, subsequent immune response. Thus, priming generates both the primary immune response and establishes immunological memory. One skilled in this art appreciates that a primary immune response represents the adaptive immune response upon initial exposure to an antigen in a particular context such as in the pathogen or in a vaccine. However, it will also be appreciated that the disclosure is not limited to use of the priming vaccine in the context of immunologically naive individuals. Rather, priming may also occur in individuals who have been exposed to the antigen but who have not received the priming vaccine. In a specific embodiment, the priming vaccine comprises an IglC antigen expressed by an *L. monocytogenes* vector.

The priming immunogenic (vaccine) composition may be administered once before administration of the boosting immunogenic (vaccine) composition. In another embodiment, the priming vaccine may be administered several times.

The boosting vaccine used in the method of the disclosure may comprise at least one *F. tularensis* antigen polypeptide. The boosting vaccine may comprise the same or a different vector. In one aspect, the boosting vaccine comprises an *F. tularensis* polypeptide antigen to enhance the immunogenicity of the subject to *F. tularensis*. For example in one aspect, the boosting vaccine comprises an *F. tularensis* antigen expressed in a viral vector. The *F. tularensis* antigen can be selected from the group consisting of AcpA, Bfr, DnaK, FabD, GroEL, IglC, KatG, Pld, Tul4, SodB or any combination thereof. In a specific embodiment, the boosting vaccine comprises KatG and/or IglC expressed in an adenovirus vector. In a specific embodiment, a vaccine combination of the disclosure comprises a prime vaccine of *L. monocytogenes* expressing IglC and/or KatG and a boosting vaccine of adenovirus expressing IglC and/or KatG, respectively.

The boosting vaccine is administered in an amount effective for "boosting" a primed immune response to the *F. tularensis* antigen. As used herein, "boosting" an immune response means to induce a secondary immune response in a subject that has been primed (i.e., already exposed) by an initial exposure to an antigen. A secondary immune response is characterized by the activation and expansion of specific memory T cells and B cells. Thus, boosting a specific immune response augments the primed immune response by inducing immune cells to proliferate and differentiate upon subsequent exposure to that antigen. The boosting vaccine may achieve one or more of the following effects: induces CD4+ T cells, induces anti-*F. tularensis* antibodies, boosts the activity of the CD8+ T cells primed by the priming vaccine, and induces additional CD8+ T cells not originally identified in the initially primed immune response. The boosting vaccine may also induce CD4+ T cells and induce anti-*F. tularensis* antibodies.

Certain vaccine adjuvants are particularly suited to the stimulation of either Th1 or Th2-type cytokine responses. Traditionally, the best indicators of the Th1:Th2 balance of the immune response after a vaccination or infection includes direct measurement of the production of Th1 or Th2 cytokines by T lymphocytes in vitro after restimulation with antigen, and/or the measurement of the IgG1:IgG2a ratio of antigen specific antibody responses. Thus, a Th1-type adjuvant is one which stimulates isolated T-cell populations to produce high levels of Th1-type cytokines when re-stimulated with antigen in vitro, and induces antigen specific immunoglobulin responses associated with Th1-type isotype.

Methods of stimulating an immune response in a subject against *F. tularensis* by administering to the subject an immunogenic amount of an *F. tularensis* antigen(s) or vector comprising an *F. tularensis* antigen, wherein the administration results in the production of an immune response. The *F. tularensis* antigen(s) preparation can be administered in combination with an immunostimulant adjuvant.

The disclosure further relates to antibodies for the prevention and/or treatment of an *F. tularensis* infection or tularemia. In a first embodiment, an antibody is raised against an *F. tularensis* antigen of the disclosure. Such antibodies are produced by administering an antigenic composition comprising a vector expression, or a purified preparation of, an *F. tularensis* antigen as a vaccine.

The antibodies according to the disclosure will be administered in one or more dosages, and the amount needed will depend on during which phase of the disease the therapy is given as well as on other factors. In order to produce such novel antibodies, the antigenic composition according to the disclosure will be administered to a subject in order to induce the production of the above described antibodies characteristic for *F. tularensis*. The antibodies can be monoclonal antibodies. Once designed, such novel antibodies may be produced by conventional techniques and used in therapy. In general, a monoclonal antibody to an epitope of an antigen can be prepared by using a technique which provides for the production of antibody molecules from continuous cell lines in culture and methods of preparing antibodies are well known to the skilled in this field (see e.g. Coligan (1991) Current Protocols in Immunology, Wiley/Greene, NY; Harlow and Lane (1989) Antibodies: A Laboratory Manual, Cold Spring Harbor Press, NY; and Goding (1986) Monoclonal Antibodies: Principles and Practice (2.sup.nd ed) Academic Press, New York, N.Y.). For therapeutic purposes, there may be an interest in using human antibodies.

For therapeutic purposes, the present antibody is formulated with conventional pharmaceutically or pharmacologically acceptable vehicles for administration, conveniently by injection. Vehicles include deionized water, saline, phosphate-buffered saline, Ringer's solution, dextrose solution, Hank's solution, etc. Other additives may include additives to provide isotonicity, buffers, preservatives, and the like. The antibody may be administered parenterally, typically intravenously or intramuscularly, as a bolus, intermittently or in a continuous regimen.

Methods for ameliorating *F. tularensis* in a subject by administering to the subject an *F. tularensis* antigen(s) or a vector comprising an *F. tularensis* antigen, in a pharmaceutically acceptable carrier, are also provided. In addition, methods for ameliorating *F. tularensis* in a subject, by administering to the subject antibodies that bind to *F. tularensis* antigens, in a pharmaceutically acceptable carrier, are also provided.

Attenuated vaccines can be administered directly to the mammal. The immunogenic compositions and vaccines obtained using the methods of the disclosure can be formulated as pharmaceutical compositions for administration in any suitable manner. One route of administration is oral. Other routes of administration include rectal, intrathecal, buccal (e.g., sublingual) inhalation, intranasal, intradermal, intramuscular, and transdermal and the like (see e.g. U.S. Pat. No. 6,126,938). Although more than one route can be used to administer a particular composition, a particular route can often provide a more immediate and more effective reaction than another route.

The immunoprotective compositions to be administered are provided in a pharmaceutically acceptable solution such as an aqueous solution, often a saline or buffered solution, or they can be provided in powder form. There is a wide variety of suitable formulations of pharmaceutical compositions of the disclosure. See, e.g., Lieberman, Pharmaceutical Dosage Forms, Marcel Dekker, Vols. 1-3 (1998); Remington's Pharmaceutical Science, 17th ed., Mack Publishing Company, Easton, Pa. (1985) and similar publications. The compositions may also include an adjuvant. Examples of known suitable adjuvants include alum, aluminum phosphate, aluminum hydroxide, and MF59 (4.3% w/v squalene, 0.5% w/v Tween 80, 0.5% w/v Span 85)—these are the only ones currently licensed for use in humans. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion, or Bacille Calmette-Guerin (BCG). The effectiveness of an adjuvant may be determined by measuring the amount of antibodies directed against the immunogenic antigen.

The concentration of immunogenic antigens of the disclosure in the pharmaceutical formulations can vary widely, e.g., from less than about 0.10, usually at or at least about 2% to as much as 20% to 500 or more by weight, and will be selected primarily by fluid volumes, viscosities, and the like, in accordance with the particular mode of administration selected.

Formulations suitable for oral administration can comprise (a) liquid solutions, such as an effective amount of the recombinant bacteria suspended in diluents, such as buffered water, saline or PEG 400; (b) capsules, sachets or tablets, each containing a predetermined amount of the active ingredient, as lyophilized powder, liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. It is recognized that the attenuated vaccines, when administered orally, must be protected from digestion. This is typically accomplished either by complexing the vaccines with a composition to render it resistant to acidic and enzymatic hydrolysis or by packaging the vaccines in an appropriately resistant carrier such as a liposome or enteric coated capsules. Means of protecting the attenuated bacteria from digestion are well known in the art. The pharmaceutical compositions can be encapsulated, e.g., in liposomes, or in a formulation that provides for slow release of the active ingredient.

The attenuated vaccines, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

The dose administered to a subject, in the context of the disclosure should be sufficient to effect a beneficial therapeutic and/or prophylactic response in the subject over time. The dose will be determined by the efficacy of the particular attenuated vaccine employed and the condition of the subject, as well as the body weight or vascular surface area of the subject to be treated. The size of the dose also will be determined by the existence, nature, and extent of any adverse side-effects that accompany the administration of a particular vaccine in a particular subject.

In determining the effective amount of the vaccine to be administered in the treatment or prophylaxis of an infection or other condition, the physician evaluates vaccine toxicities, progression of the disease, and the production of anti-vaccine vector antibodies, if any.

The compositions are administered to an animal that is at risk from acquiring an infection caused by *F. tularensis* or to prevent or at least partially arrest the development of the infection and its complications. An amount adequate to accomplish this is defined as a "therapeutically effective dose." Amounts effective for therapeutic use will depend on, e.g., the antigen composition, the manner of administration, the weight and general state of health of the subject, and the judgment of the prescribing physician. Single or multiple doses of the antigen compositions may be administered depending on the dosage and frequency required and tolerated by the subject, and route of administration. In addition, a booster may be administered in the same or different formulation. For example, the method contemplates administration of a first composition comprising an *F. tularensis* antigen in an attenuated bacterial vector and a second composition comprising an *F. tularensis* antigen in an attenuated non-bacterial vector. The second composition may be administered simultaneously or subsequent to administration of the first immunogenic composition.

In particular embodiments, a therapeutically effective dose of the immunoprotective composition is administered to a subject. Amounts of live attenuated bacteria or non-bacteria expressing the *F. tularensis* or other antigens present in the initial immunization generally range from about $5\times10^5$ to $5\times10^{11}$ organisms per subject, and more commonly from about $5\times10^8$ to $5\times10^9$ organisms per subject.

The existence of an immune response to the first dose of the immunoprotective composition may be determined by known methods (e.g., by obtaining serum from the individual before and after the initial immunization, and demonstrating a change in the individual's immune status, for example an immunoprecipitation assay, or an ELISA, or a bactericidal assay, or a Western blot, or flow cytometric assay, or the like) prior to administering a subsequent dose. The existence of an immune response to the first dose may also be assumed by waiting for a period of time after the first immunization that, based on previous experience, is a sufficient time for an immune response and/or priming to have taken place. Boosting dosages of an immunoprotective composition can be administered as needed.

The immunoprotective compositions are typically administered to an individual that is immunologically naive with respect to *F. tularensis*. Usually, 2-4 doses of an immunological composition of the disclosure may be sufficient, however additional doses may be required to achieve a high level of immunity. Additional booster doses may be given every 1-5 years, as necessary, to maintain a high level of immunity.

In general, administration to any individual should begin prior to the first sign of disease, or possibly at the first sign of possible or actual exposure to *F. tularensis*.

The toxicity and therapeutic efficacy of the attenuated vaccines provided by the disclosure are determined using standard pharmaceutical procedures in cell cultures or experimental animals. One can determine the $ED_{50}$ (the dose therapeutically effective in 500 of the population) using procedures presented herein and those otherwise known to those of skill in the art.

The attenuated vaccines of the disclosure can be packaged in packs, dispenser devices, and kits for administering genetic vaccines to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition. For example, the label may state that the active compound within the packaging is useful for treating a particular infectious disease, enteric disorder, or for preventing or treating other diseases or conditions that are mediated by, or potentially susceptible to, a mammalian immune response.

The following specific examples are meant to be illustrative and non-limiting. Those of skill in the art will recognize various modification and substitutions that can be made in the compositions and methods that follow. Such modification and substitutions do not depart from the disclosure and are encompassed herein.

EXAMPLES

Cultivated *F. tularensis* in a chemically defined medium demonstrated that *F. tularensis* RCI grows more rapidly and to a higher culture density than *F. tularensis* LVS in a 24 h period. This difference in growth rate is highly reproducible and can not be explained by a lower number of viable *F. tularensis* LVS in the initial inoculum. However, this divergence in growth rates is absent for the first 4 h during which time both strains grow from an initial OD of 0.1 to an OD of ~0.4. It is conceivable that the nutrients stored in *F. tularensis* from growth on solid chocolate agar are sufficient to support two generations of bacterial division. After the initial growth phase, the growth rate of *F. tularensis* LVS lags behind that of *F. tularensis* RCI by at least two-fold. Although growing significantly slower in the defined medium, with an extended cultivation time, *F. tularensis* LVS can still achieve the same ultimate cell density as that of *F. tularensis* RCI. In one experiment, for example, the *F. tularensis* RCI culture reached an OD of 3.5 in 20 h, whereas it took 45 h for *F. tularensis* LVS to reach a similar culture density. The slower growth rate of *F. tularensis* LVS in Chamberlain medium could be due to slower adaptation or to less efficient transport or utilization of certain nutrient(s) in the defined medium. *F. tularensis* LVS is a strain used widely in tularemia research and presumably has gone through many passages in laboratories over the years. It is possible that the slower growth of LVS in Chamberlain medium is merely the result of extensive passages on enriched agars and media. Alternatively, the differential growth rate of *F. tularensis* LVS and RCI in Chamberlain medium may reflect a fundamental difference between *F. tularensis* subspecies *holarctica* and the more virulent subspecies *tularensis*.

Bacteria. *F. tularensis* live vaccine strain (LVS) and a virulent recent clinical isolate (NY 96-3369; RCI) were obtained from the Centers for Disease Control and Prevention (Atlanta, Ga.). Bacteria were cultivated on chocolate II agar (BD BBL, Sparks, Md.), passaged through THP-1 cells, a human monocytic cell line (American Type Culture Collection) and stored at −80° C.

Culture media. Chemically defined Chamberlain medium was prepared. All ingredients used in preparation of the medium were purchased from Sigma (St. Louis, Mo.). The medium was stirred overnight and sterilized by passing through a 0.2 μm filtration unit. The final medium had a pH of 6.3-6.5. Mueller Hinton broth (BD BBL) was supplemented with 0.0250 ferric pyrophosphate and 20 IsoVitaleX (BD BBL). Brain heart infusion broth (BD BBL) was supplemented with 1% β-cyclodextrin (Sigma). Tryptic soy broth (BD BBL) was supplemented with 0.10 cysteine hydrochloride (Sigma).

Bacterial cultures. Overnight cultures of *F. tularensis* on chocolate II agar plates were scraped and washed twice in normal saline and resuspended in Chamberlain medium to an optical density (OD) of 0.1 at 540 nm. Bacterial cultures were grown at 37° C. in Erlenmeyer flasks equipped with 0.2 μm filter caps (Corning Incorporated, Corning, N.Y.), rotated at 200 rpm, and harvested at selected time points by centrifugation at 3500 rpm, 4° C. for 30 min. Culture supernate was passed sequentially through 0.45 μm and 0.2 μm filters. Culture supernates of volume 200 ml or less were concentrated using 5 kDa cut-off Centricon Plus-20 Centrifugal Filter Devices (Millipore Corporation, Bedford, Mass.). Culture supernates of volume greater than 200 ml were first concentrated using an Amicon ultrafiltration cell with a YM10 membrane (Millipore) and then further concentrated using a Centricon Plus-20 Centrifugal Filter Device. Bacterial pellets were resuspended in Dulbecco's phosphate buffered saline (PBS) and subjected to sonication on ice with a W-375 sonication Ultrasonic processor (Heat Systems-Ultrasonics, Inc., Farmingdale, N.Y.) at 50% duty cycle with pulse and strength setting 5 for three 1 min sessions. Insoluble material and unbroken bacteria were removed by centrifugation. Protein concentration in the culture filtrate and in the clear lysate obtained from bacterial sonication was determined by bicinchonic acid (BCA) protein assay (Pierce Biotechnology, Rockford, Ill.) with albumin as standard.

Radiolabeling of culture filtrate proteins. *F. tularensis* RCI was cultured in Chamberlain medium for 4 h at 37° C. to an $OD_{540}$ of 0.4-0.5. The bacteria were pelleted by centrifugation, washed once in normal saline, and suspended in methionine-free Chamberlain medium. [$^{35}$S]-methionine (Amersham Pharmacia Biotech., Little Chalfont, England) was added to the culture to a final concentration of 100 μCi/ml, the culture was incubated for 1 h, and the radiolabeled culture filtrate was obtained and processed as described above for non-radiolabeled bacterial cultures.

Lactate dehydrogenase assay. Activity of lactate dehydrogenase was measured by a modification of the method of Reeves and Fimognari. Concentrated protein samples from 20 ml equivalent of culture filtrate or 1 ml equivalent of bacterial lysate were added to 0.85 ml of PBS, 50 µl of NADH (2.5 mg/ml), and 50 µl of sodium pyruvate (2.5 mg/ml). The decrease in optical density at 340 nm was measured over a 2-min period at room temperature in an optical cuvette with 1.0 cm path length. One unit of lactate dehydrogenase activity is defined as the amount of enzyme required to produce 1.0 µmole of lactate within a minute.

Protease assays. Protease activity was analyzed both by zymogram and a quantitative colorimetric protease assay. Proteins concentrated from 40 ml of culture filtrate were analyzed by zymogram using polyacrylamide gels embedded with 10% casein or 12% gelatin (Bio-Rad Laboratories, Hercules, Calif.) according to the manufacturer's instructions. Proteinase K (Epicentric, Madison, Wis.), 1 µg, was loaded onto the same zymogram gel as a positive control. Culture filtrate proteins harvested from 200 ml bacteria cultures were desalted by passing through an Excellulose GF-5 column (Pierce). Protein effluent was monitored at 280 nm, combined and concentrated for use in the assay. Protease was quantified using the QuantiCleave Protease Assay kit (Pierce). A standard curve was prepared using TPCK trypsin at concentrations of 0.5 mg/ml to 0.5 ng/ml.

Two-dimensional polyacrylamide gel electrophoresis (2-DE). Culture filtrate proteins (200 µg) were dissolved in sample buffer containing 8 M urea, 2% CHAPS, 50 mM dithiothreitol (DTT) and 0.20 (w/v) Bio-Lyte 3/10 ampholytes and separated using a 16 cm×1.5 mm isoelectric focusing (IEF) tube gel (Biolyte 5/7 ampholytes:Biolyte 3/10 ampholytes=4:1) at 200 V for 2 h, 500 V for 2 h, and 800 V for 14 h. The IEF gel was equilibrated 15 min each with buffer I containing 6 M urea, 2% SDS, 0.375 M Tris-HCl (pH 8.8), 200 glycerol, and 20 (w/v) DTT and buffer II containing 6 M urea, 2% SDS, 0.375 M Tris-HCl (pH 8.8), 20% glycerol, and 2.50 (w/v) iodoacetamide. Each equilibrated IEF gel was loaded onto a 16 cm×16 cm×1 mm 12.5% SDS-PAGE gel. The second dimension gel system was run at 20 mA for the stacking gel and 30 mA for the separating gel. The gels were fixed in 40% ethanol and 10% acetic acid for 1 h, stained with 0.1% (w/v) Coomassie Brilliant Blue G, 10% ethanol, 20 phosphoric acid, and 10 (w/v) ammonium sulfate for 4 h, and destained with 3-4 changes of 10% acetic acid.

N-terminal amino acid sequencing. Proteins separated by one- or two-dimensional polyacrylamide (2-D) gel electrophoresis were transferred to a PVDF membrane in 10 mM CAPS, pH 11 and stained with Coomassie Brilliant Blue R-250. Protein spots cut from the membrane were subjected to N-terminal amino acid sequencing by Edman degradation at the Molecular Structure Facility, University of California, Davis.

Protein homology search. *F. tularensis* (Schu 4) genome was downloaded from the website (http:)//artedi.ebc.uu.se/Projects/Francisella/data. A collection of open reading frames of length≧50 amino acids were translated using the computer program Artemis and searched for N-terminal amino acid sequences obtained for individual protein spots. An open reading frame was assigned to a particular protein spot only if it met all three of the following criteria: (a) the open reading frame encoded a polypeptide whose N-terminus (within the first 3 methionines of the open reading frame) matched the sequence of the first 7 (or more) amino acid residues of the protein spot; (b) this matched sequence was the only one found in the entire collection of open reading frames; and (c) the calculated molecular mass of the polypeptide predicted by the open reading frame approximated the size of the protein spot observed on SDS-PAGE. A blast search was then conducted in the GenBank database using the entire protein sequence. A potential identity was assigned to an open reading frame based on its high percentage of identity or similarity in primary sequence to a protein of a known physiological function and/or by virtue of its possessing one or more conserved domain(s) of such a protein.

Amplification of *F. tularensis* genes. Genomic DNA of *F. tularensis* RCI was isolated. *F. tularensis* RCI cultured in Chamberlain medium was pelleted by centrifugation and incubated at 50° C. for 12 h in a lysis solution containing 10 mM NaCl, 20 mM Tris-HCl, pH 8, 1 mM EDTA, 0.5% SDS, and 0.7 mg/ml protease. Bacterial lysate was treated with sodium perchlorate at room temperature for 1 h and extracted three times with an equal volume of phenol-chloroform-isoamyl alcohol (25:24:1). Nucleic acids were precipitated from the aqueous phase, resuspended, and treated with RNase at 37° C. for 1 h. After another round of extraction with phenol-chloroform-isoamyl alcohol, genomic DNA was precipitated and dissolved in buffer containing 10 mM Tris-HCl, pH 8, and 1 mM EDTA. Primer pairs used for amplification of individual genes from the isolated *F. tularensis* RCI genomic DNA were as follows: 5'-CCGCTCGAGCATATGCTAAAGAAAATTGTAACTGCTTTAGG AATGTCTGGAATGCTACTAGC-3' (SEQ ID NO:21) and 5'-CCGCTCGAGTTAACAAATTTATTGTTGAACATCAAATCTGCCAAGC ATCATAACTTTATGCC-3' (SEQ ID NO:22) for katG; 5'-CGGGATCCCATATG GCTGCAAAACAAGTTTTATTTTCAGATGAAGCTC-3' (SEQ ID NO:23) and 5'-CGGGATCCCTATTACATCATGCCAGGCATACCGCCCATGCCACCGCC-3' (SEQ ID NO:24) for groEL; 5'-CGGGATCCCATATGTC AAAAACAGCTGTAGTTTTTCCTGGTCAAGGTTC-3' (SEQ ID NO:25) and 5'-CGGGATCCTTAAATATTTTCTAAACTATCAATACTGTTTGTATCTTTT-3' (SEQ ID NO:26) for fabD; 5'-CGGGATCCGGCTTACCACATGATCT AATTGCCGTTGCTGCATGCGC-3' (SEQ ID NO:27) and 5'-CGGGATCC AGCTATCAAGATCACAACCACTATTGATAAAACCCCTA-3' (SEQ ID NO:28) for sodB; and 5'-CCGGATCCCCATCTTTAAATGTACAGGTTG TATCTAGACTTTCTGC-3' (SEQ ID NO:29) and 5'-CGGGATCCG TCACTGAATATCTCGATAGCGCATTCTAGTGAATCCAAG-3' (SEQ ID NO:30) for bfr. DNA polymerase from the PfuUltra Hotstart (Stratagene, La Jolla, Calif.) or FailSafe (Epecentric, Madison, Wis.) system was used in the amplification reactions under a typical condition of 1 cycle at 95° C. for 1 min; 30 cycles at 95° C. for 1 min, 50° C. for 1 min, 72° C. for 1-2 min depending on the length of the target gene, and 1 cycle at 72° C. for 10 min. The amplified product was gel purified and ligated with pZero (Invitrogen, Carlsbad, Calif.). The identity of each cloned gene was confirmed by nucleotide sequencing. Nucleotide sequencing was carried out by the UCLA sequencing core facility. The nucleotide sequences for genes of *F. tularensis* RCI have been submitted to Genbank under the accession numbers: AY662299 (katG), AY662300 (groEL), AY662301 (fabD), AY662302 (sodB), AY662303 (bfr).

Cloning and expression of *F. tularensis* genes. Genes for groEL and fabD were subcloned directly from pZero into pET15b (Novagen, Madison, Wis.) between NdeI and BamHI restriction sites. Genes for sodB and bfr were amplified from the corresponding pZero constructs with proper restriction sites and inserted between the NdeI and BamHI restriction sites on pET15b. For expression of katG in full length, the gene was released from pZero with NdeI and XhoI and ligated with pET22b (Novagen) treated with the same enzymes. *F. tularensis* genes cloned into the expression vector pET15b produce recombinant proteins with a thrombin cleavable histidine tag at the N-terminus, and the katG gene cloned into pET22b produces a recombinant protein with the histidine tag fused to its C-terminus. *E. coli* BL21 CodonPlus (DE3)-RIL (Stratagene) transformed with the pET15b or pET22b constructs were first grown in LB medium to an absorbance of 0.4 at 540 nm and then induced with 1 mM isopropyl-β-D-thiogalacto-pyranoside (IPTG) for 5 h before harvesting. The culture filtrate and the soluble and insoluble fractions from the bacterial sonicate were analyzed on 12.5% SDS-PAGE gels to assess the expression and solubility of the recombinant proteins.

The attenuated *L. monocytogenes* host strain, *L. monocytogenes* Strain 10403S (serotype 1/2a) with a deletion in the gene for actin polymerization (Act A-deficient) was used (Shen et al. 1995 and Craft et al. 2005). The iglC gene of *F. tularensis* was cloned into pKB199 downstream of the hemolysin promoter and leader sequence (PLhly) of *L. monocytogenes*. The expression cassette of PLhly-iglC was excised from pKB199 and cloned into the site-specific integration vector pDP4189 to generate pDP4189-iglC. The plasmid pDP4189-iglC was transformed into SM10, the *E. coli* conjugation donor strain. Through conjugation, the plasmid was mobilized and transferred from its *E. coli* SM10 host into the recipient *L. monocytogenes* ΔactA strain. The conjugation mixture was selected on plates containing streptomycin and chloramphenicol. The ΔactA strain is insensitive to streptomycin since it is derived from the *L. monocytogenes* strain 10403S, a spontaneous mutant resistant to streptomycin. *E. coli* SM10 is sensitive to streptomycin, therefore was not able to grow on the selective plate. The plasmid pDP4189 carries the chloramphenicol resistance gene and is unable to replicate in *Listeria*. Under the selection pressure from chloramphenicol, the plasmid pDP4189-iglC integrated in the 3' end of an arginine tRNA gene on the chromosome of *L. monocytogenes* ΔactA strain. The resulting *L. monocytogenes* ΔactA strain carries a single copy of the iglC gene from *F. tularensis* and is stable in the absence of antibiotic selection. *L. monocytogenes* expressing *F. tularensis* katG. The strain was constructed by the same approach as described above. *L. monocytogenes* expressing *F. tularensis* AcpA. The strain was constructed by the same approach as described above. *L. monocytogenes* expressing *F. tularensis* Bfr. The strain was constructed by the same approach as described above. *L. monocytogenes* expressing *F. tularensis* GroEL. The strain was constructed by the same approach as described above. *L. monocytogenes* expressing *F. tularensis* Pld. The strain was constructed by the same approach as described above. *L. monocytogenes* expressing *F. tularensis* DnaK. The strain was constructed by the same approach as described above.

Recombinant Protein Expression in Recombinant *L. monocytogenes* Strains. A single colony of *L. monocytogenes* ΔactA strain integrated with the iglC gene of *F. tularensis* was inoculated into 3 ml Brain-Heart Infusion (BHI) medium containing streptomycin (50 μg/ml) and chloramphenicol (7.5 μg/ml) and grown overnight at 37° C., 250 rpm. The overnight culture was inoculated into 40 ml fresh MOPS-buffered BHI medium containing streptomycin and chloramphenicol at an initial optical density of 0.05 at 540 nm. The culture was grown at 37° C., rotating at 250 rpm for 5 h, before it was harvested by centrifugation at 3500 rpm, 4° C. for 30 min. The supernatant was passed through a 0.2 μm filter membrane, and proteins in the culture filtrate were precipitated by trichloro-acetic acid. The expression of IglC was analyzed by separating the protein precipitates on SDS-PAGE, transblotting to a nitrocellulose membrane, and probing with a rabbit antibody specific to the IglC of *F. tularensis*. The antibody reacted with a protein band of 23 kDa in size corresponding to that of *F. tularensis* IglC. The antibody also detected a second protein band slightly smaller in size and most likely a breakdown product of IglC. Both immunoreactive protein bands were absent from the *Listeria* parental strain. This confirmed that the recombinant *L. monocytogenes* expresses IglC.

Protein purification and antibody production. Recombinant Bfr, FabD, SodB, DnaK, Tul4, AcpA, Pld, KatG, and GroEL were purified by Ni-NTA metal-affinity chromatography and by elution with imidazole. N-terminal histidine tag was cleaved off from the recombinant proteins by digestion with biotinylated thrombin, which was subsequently removed with streptavidin agarose (Novagen). Residual recombinant proteins still bearing the histidine tag were removed by a second round of Ni-NTA chromatography. Purification of recombinant KatG was carried out with a combination of Ni-NTA and Q-sepharose chromatography. Purity of the recombinant proteins was assessed by SDS-PAGE. Similarly, purified IglC was prepared except that it was linked to a chitin tag instead of a histidine tag. Purified recombinant proteins (Bfr, FabD, SodB, DnaK, Tul4, AcpA, Pld, KatG, GroEL, and IglC) were used to immunize rabbits for antibody production (Covance, Denver, Pa.).

Western blot analysis. Proteins separated by 10% or 12.5% SDS-PAGE were transblotted in Tris-glycine buffer at 45 V for 5 h onto a 0.45 μm nitrocellulose membrane (Bio-Rad). For colorimetric detection of recombinant proteins, the membrane blot was probed first with an anti-histidine tag monoclonal antibody (Amersham Pharmacia) at a dilution of 1:3000 and then with alkaline phosphatase-conjugated goat anti-mouse antibodies (Sigma). Immunoreactive protein bands were visualized with developing reagent containing 5-bromo-4-chloro-3-indoyl phosphate p-toluidine salt and p-nitro blue tetrazolium chloride. For chemiluminescent detection, the membrane blot was reacted with antibodies specific to KatG, GroEL or Bfr at a dilution of 1:5000 and subsequently with a 1:25000 dilution of horseradish peroxidase conjugated goat anti-rabbit IgG (Bio-Rad). Signals were developed by incubating with chemiluminescent substrate (Pierce) and detected by exposing X-ray film. The anti-GroEL antibody was pre-absorbed with acetone extracts of THP-1 cells to remove antigen cross-reactivity.

Analysis of bacterial proteins released during infection of macrophages. Differentiated THP-1 cells ($10^7$) were infected with *F. tularensis* RCI ($10^8$) in RPMI medium containing 10% human serum type AB for 90 min at 37° C. and 5% $CO_2$, washed 3 times with PBS, and incubated in RPMI medium containing gentamicin (2 μg/ml) and 10% heat-inactivated fetal bovine serum (HI-FBS). The monolayer was washed after 10 h incubation and harvested by scraping into homogenization buffer containing 250 mM sucrose, 20 mM HEPES-KOH, pH 7.3 and 0.5 mM EGTA and centrifuged at 600×g, 4° C. for 15 min. The pelleted cells were resuspended in ice-cold homogenization buffer containing DTT activated streptolysin-O (25 U/ml). The cells were incubated on ice for 15 min and subsequently at 37° C. for another 15 min to effect permeabilization, and then centrifuged at 14000×g, 10 min. The supernate was passed through a protein desalting spin column (Pierce) and analyzed by SDS-PAGE and Western immunoblotting.

Lymphocyte proliferation assay. Female BALB/c mice purchased from Charles River Laboratories were injected intradermally with $5\times10^4$ live or heat-killed *F. tularensis* LVS or PBS alone. Mice were euthanized 5, 9 and 15 weeks later. Splenocytes were prepared and cultured in 96-well U-bottom plates at a concentration of $2\times10^6$ cells per 0.1 ml per well in RPMI medium containing 10% HI-FBS, polymyxin B (100 U/ml) and purified recombinant proteins (10 μg/ml). After 72 h of incubation, splenocytes were pulsed with 0.25 μCi of methyl-[$^3$H]thymidine (Amersham Pharmacia Biotech) per well and harvested 16 h later with a cell harvester (Skatron). The amount of incorporated [$^3$H]thymidine was determined by counting in a liquid scintillation counter. The stimulation index (SI) was defined as the ratio of the counts-per-minute value obtained from cells incubated with the purified protein antigen divided by the counts-per-minute value obtained from cells incubated without antigen.

Intracellular cytokine staining. BALB/c mice were immunized intradermally with $5\times10^4$ live or heat-killed *F. tularensis* LVS or PBS alone. Spleens were harvested 9 weeks later from the immunized mice. Red blood cells were lysed with PharmLyse (BD Pharmingen, San Diego, Calif.). Splenocytes were washed and seeded at a density of $2\times10^6$ cells per 0.1 ml per well in RPMI medium containing 10% HI-FBS and IL-2 (50 U/ml) and incubated with or without purified protein antigen (10 μg/ml) for 24 h at 37° C., 5% $CO_2$. Golgi-Plug (BD Pharmingen) was added and the cells incubated an additional 12 h. Cells were pelleted at 250×g, 4° C. for 5 min and resuspended in PBS containing 3% FBS, 0.09% sodium azide (staining buffer), and Fc-Block (BD Pharmingen). After incubation at 4° C. for 15 min, cells were stained with anti-CD4-FITC or anti-CD8-CyC at 1:100 dilution on ice for 30 min. Cells were washed twice in staining buffer, fixed with Cytofix solution for 20 min at 4° C., and washed twice with Perm/Wash solution. Cells were then stained for intracellular IFN-γ with rat anti-mouse IFN-γ-PE or a PE-labeled isotypic control IgG at a dilution of 1:100. Stained cells were washed, resuspended in staining buffer and analyzed on a FACSCalibur flow cytometer using CellQuest software.

Generation of O-antigen deficient *F. tularensis* LVS. Lipopolysaccharide (LPS) is a complex molecule associated with the outer membrane of Gram-negative bacteria such as *F. tularensis*. The LPS molecule consists of the lipid component (Lipid A) and the polysaccharide component (O-antigen). Immunogenicity of the LPS is associated with the O-antigen component of the molecule. The chemical structure of the O-antigen of *F. tularensis* subspecies *tularensis* has been determined to be multiple repeats of a single subunit, which consists a linear linkage of 4 sugars (-1,2→QuiNAc4Fm-1, 4→GalNAcAN-1,4→GalNAcAN-1,3→QuiNAc-1,2→). To disrupt biosynthesis and formation of the O-antigen repeat subunit of *F. tularensis*, a knock-out of three consecutive genes, wbtD, wbtE and wbtF, which are involved in the biosynthesis of the O-antigen were performed. The wbtE and wbtF genes are involved in the biosynthesis of the sugar residue GalNAcAN, while the wbtD gene codes for a sugar transferase and is responsible for linking GalNAcAN to the first sugar residue, QuiNAc, of an O-antigen repeat subunit.

The suicide plasmid, pSMT22::wbtDEFΔ (pSMT22-RT1) comprising a cassette of mutated wbtD (missing the stop codon) and wbtF (missing both the start and stop codons) genes flanking either side of the chloramphenicol acetyltransferase gene (cat) was used. *Escherichia coli* S17-1 carrying the plasmid was mixed with the *F. tularensis* Live Vaccine Strain (LVS) of *F. tularensis* at a ratio of 1:10 (*E. coli*:LVS) and incubated at room temperature overnight to allow bacterial conjugation to occur. The suicide plasmid was transferred from *E. coli* to LVS through the bacterial conjugation. Following an overnight incubation, the bacterial mixture was selected on chocolate II agar containing chloramphenicol (2.5 μg ml$^{-1}$) and polymyxin B (100 μg ml$^{-1}$). The suicide plasmid is not able to replicate in *Francisella tularensis* and is usually lost after several rounds of bacterial division. However, the plasmid can integrate into the bacterial chromosome through homologous recombination and be maintained within its bacterial host. The LVS strain is sensitive to chloramphenicol and insensitive to polymyxin B at the above concentrations. Under the selective pressure of chloramphenicol, only LVS with the plasmid integrated into its chromosome can multiply. The *E. coli* donor is sensitive to polymyxin B and thus cannot grow on the selective agar. Colonies of the LVS mutant appeared 4-6 days after plating on the selective medium and were screened by PCR amplification for the cat gene to confirm integration of the suicide plasmid into the bacterial chromosome. The LVS mutants were then subjected to a second round of selection on chocolate II agar containing 5% sucrose and chloramphenicol to force a second homologous recombination event to occur. The sacB gene on the suicide plasmid produces toxic effects to the bacteria in the presence of sucrose. Therefore, the only LVS mutants that can grow under such a dual selection of sucrose and chloramphenicol are the ones that have lost the rest of the suicide plasmid along with the parental copy of the wbtDEF genes but have kept the mutated copy of the wbtD and wbtF genes and the cat gene. LPS molecules made by the LVS mutants lack a functional O-antigen and have, at most, a single QuiNAc sugar residue attached to the Lipid A moiety of the LPS molecule.

*L. monocytogenes* expressing *F. tularensis* KatG. Expression of the *F. tularensis* KatG protein in the *L. monocytogenes* ΔactA strain was analyzed by the same method as described above using a rabbit antibody specific to the KatG of *F. tularensis*. Two protein bands were detected by the antibody on immunoblots of the recombinant *Listeria* strain. Both of these bands were absent from the immunoblots of the *Listeria* parental strain. The first immunoreactive band had a molecular mass corresponding to that of *F. tularensis* KatG (80 kDa). The second immunoreactive band was approximately 40 kDa in size and presumed to be the breakdown product of KatG. This confirmed that the recombinant *L. monocytogenes* expresses KatG.

*L. monocytogenes* expressing *F. tularensis* AcpA. Expression of the *F. tularensis* AcpA protein in the *L. monocytogenes* ΔactA strain was analyzed by the same method as described above using a rabbit antibody specific to the AcpA of *F. tularensis*. The antibody reacted with a protein band of similar size to that of *F. tularensis* AcpA (54 kDa). The antibody also detected two other protein bands of a smaller size and most likely the breakdown products of AcpA. All three immunoreactive protein bands were absent from the immunoblots of the *Listeria* parental strain. This confirmed that the recombinant *L. monocytogenes* expresses AcpA.

*L. monocytogenes* expressing *F. tularensis* Bfr. Expression of the *F. tularensis* Bfr protein in the *L. monocytogenes* ΔactA strain was analyzed by the same method as described above using a rabbit antibody specific to the Bfr of *F. tularensis*. The antibody reacted strongly with a protein band on immunoblots of the recombinant *Listeria* strain that was absent on immunoblots of the *Listeria* parental strain. The immunoreactive band had a molecular mass corresponding to that of *F. tularensis* Bfr (17 kDa). This confirmed that the recombinant *L. monocytogenes* expresses Bfr.

*L. monocytogenes* expressing *F. tularensis* GroEL. Expression of the *F. tularensis* GroEL protein in the *L. monocytogenes* ΔactA strain was analyzed by the same method as described above using a rabbit antibody specific to the GroEL of *F. tularensis*. The antibody detected a strong protein band of approximately 57 kDa in size on the immunoblots of the recombinant *L. monocytogenes* strain; this band was absent on the immunoblots of the parental *L. monocytogenes* strain. This confirmed that the recombinant *L. monocytogenes* expresses GroEL.

*L. monocytogenes* expressing *F. tularensis* Pld. Expression of the *F. tularensis* Pld protein in the *L. monocytogenes* ΔactA strain was analyzed by the same method as described above using a rabbit antibody specific to the Pld of *F. tularensis*. The antibody detected multiple protein bands of approximately 40-50 kD, which are close to the estimated 43 kD molecular weight of Pld. This confirmed that the recombinant *L. monocytogenes* expresses Pld.

*L. monocytogenes* expressing *F. tularensis* DnaK. Expression of the *F. tularensis* DnaK protein in the *L. monocytogenes* ΔactA strain was analyzed by the same method as described above using a rabbit antibody specific to the DnaK of *F. tularensis*. The antibody detected a large band of ~75 kD on immunoblots of the recombinant *L. monocytogenes* strain. This confirmed that the recombinant *L. monocytogenes* expresses DnaK.

FIG. 1 depicts immunoblots showing expression of *F. tularensis* proteins by the various recombinant *L. monocytogenes* strains described above.

Replication-deficient adenovirus expressing *F. tularensis* KatG, AdvΔE1E3/Ft KatG. The replication-deficient recombinant adenovirus strain that expresses *F. tularensis* KatG was constructed using an AdenoVator system (Q Biogen). The KatG gene of *F. tularensis* was first cloned into a transfer vector of pAdenoVator-CMV5 downstream of a modified immediate-early promoter of cytomegalovirus (CMV5), which allows for the production of high levels of heterologous proteins in mammalian cells. The transfer vector contains a kanamycin-resistant gene that allows for selection of recombinant adenoviral DNAs. The transfer vector containing the KatG coding sequence was then co-transformed into *E. coli* together with an adenoviral plasmid DNA with deletions in viral early genes E1 and E3, pAdenoVatorΔE1/E3. The E1 but not the E3 gene is essential for adenovirus growth in mammalian cells. Thus the recombinant adenoviruses with E1 and E3 deletions are replication-deficient and can grow only on cells that express the E1 gene. Through homologous recombination between the transfer vector and the adenoviral plasmid DNA in *E. coli*, the KatG gene driven by the CMV5 promoter was introduced into the deleted E1 region of the adenoviral plasmid DNA. Recombinant adenoviral DNAs were selected with kanamycin and confirmed by restriction enzyme analysis. A positive recombinant adenoviral DNA that was confirmed to contain the appropriate insert, pAdvΔE1E3/Ft KatG, was linearized with restriction enzyme (PacI) and transfected into mammalian cells (293A) that express the E1 protein. The resultant replication-deficient recombinant adenoviruses were plaque purified and amplified in 293A cells for up to 4 passages. The expression of *F. tularensis* KatG by the recombinant adenovirus, AdvΔE1E3/Ft KatG, was confirmed by Western blotting using a rabbit polyclonal antibody to KatG. The replication-deficient recombinant adenovirus stock was prepared from $6 \times 10^8$ 293A cells and purified by two rounds of ultracentrifugation on CsCl gradients. The amount of virus particles in the virus stock was measured by assessing the DNA content of lysed virus in solution and utilizing the extinction coefficient of $1.1 \times 10^{12}$ virus particles per $OD_{260}$ unit. The amount of infectious virus in the virus stock was measured by determining the tissue culture infectious dose 50 ($TCID_{50}$) in 293A cells.

Replication-deficient adenovirus expressing *F. tularensis* IglC, AdvΔE1E3/Ft IglC. This strain was generated in a way that was similar to that described above for AdvΔE1E3/Ft KatG. The expression of *F. tularensis* IglC was confirmed by the identification of a 23 kD protein on Western blots using a rabbit polyclonal antibody against IglC generated in this laboratory.

Replication-deficient adenovirus expressing *F. tularensis* KatG-IglC fusion protein, AdvΔE1E3/Ft KatG-IglC. A transfer vector that contained the sequence encoding *F. tularensis* KatG and IglC was obtained and used. The sequence encoding KatG and the sequence encoding IglC were directly ligated without a linker sequence; thus the IglC is fused to the C-terminus of KatG. The insertion of the sequence encoding both KatG and IglC was confirmed by sequence analysis of the transfer plasmid DNA. The expression of the KatG-IglC fusion protein by the transfer vector was confirmed by Western blotting using a polyclonal antibody against *F. tularensis* KatG, which detected a band of approximate 100 kD. The replication-deficient adenovirus expressing KatG-IglC was constructed using the method described above for AdvΔE1E3/Ft KatG.

Replication-deficient adenovirus expressing *F. tularensis* IglC-katG fusion protein, AdvΔE1E3/Ft IglC-katG. As a control for AdvΔE1E3/Ft KatG-IglC, a recombinant adenoviruses is constructed that express KatG fused to IglC at its C-terminus. A shuttle vector that contains sequences encoding IglC and KatG is used. The protein expression of IglC-katG is confirmed.

Identification of abundant *F. tularensis* proteins likely to be highly immunogenic. Proteins released in abundance by *F. tularensis* were hypothesized to be prime vaccine candidates because their release inside the host cells would make them available for processing and presentation to the immune system. Such proteins would therefore induce a strong T-cell response and be highly immunogenic. To identify abundantly released proteins of *F. tularensis*, a [$^{35}$S]-metabolic radiolabeling, one and two-dimensional polyacrylamide gel electrophoresis, and N-terminal amino acid sequencing was used to evaluate the proteins released by *F. tularensis* growing in a defined medium. By this approach, a total of 12 major proteins released by *F. tularensis* were identified (Lee et al. 2006).

The protein profiles obtained from a virulent recent clinical isolate (RCI) of *F. tularensis* subspecies *tularensis* with that from the LVS strain by two-dimensional polyacrylamide gel electrophoresis were also analyzed. KatG, DnaK, GroEL, and Bfr are among the most abundant proteins in the culture filtrate of the two *F. tularensis* strains. DnaK and GroEL are present at about the same level in the culture filtrate of both strains. KatG is much more abundant (~14 fold) in the RCI than LVS culture filtrate. Bfr is more abundant in the culture filtrate of the LVS strain (Lee et al. 2006).

Expression of *F. tularensis* proteins in Recombinant *E. coli*. The iglC encoding gene was amplified from the genomic DNA of *F. tularensis* RCI and cloned into pZero. Identity of the amplified gene product in pZero was confirmed by nucleotide sequencing. The iglC gene was subsequently cloned into expression vector pTWIN1 in such a way that it fused to the 3' end of a chimeric gene sequence on the plasmid vector to generate pTWIN-iglC. The chimeric gene on pTWIN1 consists the coding sequence for a chitin binding domain (CBD) from *B. circulans* and the dnaB intein from *Synechocystis* sp. The construct was verified by restriction enzyme digestions and transformed into the expression host *E. coli* BL21 CodonPlus (DE3)-RIL.

The expression test of IglC was conducted by inoculating 0.5 ml of an overnight culture of the recombinant *E. coli* into 10 ml LB medium supplemented with 1% glucose and 100 µg/ml carbenicillin. The culture was grown for 3 h at 28° C. for 3 h. The expression inducer IPTG was added to the culture to a final concentration of 0.5 mM. The culture was grown for another 3 h and then harvested by centrifugation. The bacterial pellet from the centrifugation was suspended in PBS and sonicated to break open the bacterial cell envelope. Soluble proteins released from the bacterial cytoplasm due to sonication were separated from the insoluble materials by centrifugation. Both fractions, containing either the soluble or the insoluble materials generated from the bacterial culture, were analyzed by SDS-PAGE and coomassie blue staining. The expression of IglC was evident by the presence of an intense protein band corresponding to the molecular mass of the CBD-DnaB intein-IglC fusion protein. Most importantly, the fusion protein was found predominantly in the soluble fraction. The analysis indicated that the recombinant E. coli expressed IglC of F. tularensis at high level as a soluble protein.

The gene coding for katG was amplified by PCR from the genomic DNA of F. tularensis RCI, and cloned into pZero. Identity of the amplified gene product was confirmed by nucleotide sequencing. The katG gene containing both the sequence coding for its signal peptide and the mature protein was subsequently cloned into the expression vector pET22b and transformed into E. coli BL21 CodonPlus (DE3)-RIL. The expression construct is designed to produce and export F. tularensis KatG with a short tag of 6 histidine residues at the C-terminus by the recombinant E. coli.

The expression of KatG was tested by inoculating 0.5 ml of an overnight culture of the recombinant E. coli into 10 ml LB medium containing carbenicillin. The culture was grown for 2 h with rotation before addition of IPTG to a final concentration of 1 mM. The culture was continued for an additional 5 h before harvesting by centrifugation. The culture supernatant was passed through a 0.2 µm filter membrane, and the pellet was sonicated to release bacterial proteins that were soluble. Analysis from SDS-PAGE and coomassie blue staining indicated that the KatG protein was expressed and released by the recombinant E. coli into its culture medium. N-terminal amino acid sequencing of the recombinant KatG protein released by E. coli revealed a sequence of the mature protein identical to that of KatG from the culture filtrate of F. tularensis RCI.

The gene for acpA was amplified from the genomic DNA of F. tularensis RCI and confirmed by nucleotide sequencing. The acpA was cloned into the expression vector pET20b immediately downstream of the E. coli pelB leader sequence. The plasmid construct pET20b-acpA was transformed into E. coli BL21 CodonPlus (DE3)-RIL and tested for expression.

A fresh bacterial culture was initiated by inoculating an overnight culture of the recombinant E. coli into LB medium containing 20 glucose, carbenicillin (100 µg/ml) and chloramphenicol (50 µg/ml). The culture was grown at 28° C. for 2 h, and then IPTG was added to the culture to a final concentration of 0.5 mM. The culture was continued for another 4 h before harvesting by centrifugation. The bacterial pellet was sonicated and subjected to analysis by SDS-PAGE and coomassie blue staining. The expression of AcpA was apparent by the presence of a major protein band, corresponding to the molecular mass of AcpA, after electrophoresis of the soluble fraction of the recombinant E. coli culture induced with IPTG; by SDS-PAGE, the amount of this protein was significantly less in the soluble fraction of the recombinant E. coli culture not induced with IPTG.

The gene coding for Bfr was amplified from the genomic DNA of F. tularensis RCI and confirmed by nucleotide sequencing. The bfr gene was cloned into the expression vector pET15b and transformed into the E. coli expression host BL21 CodonPlus (DE3)-RIL. The expression gene cassette is designed to produce F. tularensis Bfr by the E. coli expression host as a fusion protein with 6 histidine residues at its N-terminus.

Expression of F. tularensis Bfr was assessed by inoculating 0.5 ml of an overnight recombinant E. coli culture into fresh 10 ml LB medium containing carbenicillin (100 µg/ml) in duplicate. The E. coli cultures were grown at 37° C., 250 rpm for 2 h before the addition of IPTG to a final concentration of 1 mM to one of the two cultures. The E. coli cultures were allowed to grow for an additional 5 h before harvesting by centrifugation. The bacterial pellet was suspended in PBS, sonicated on ice, and centrifuged for 10 min at 12,000 rpm. The resulting supernate and the insoluble pellet were subjected to SDS-PAGE analysis and stained with coomassie blue.

The expression of Bfr was evident by the presence of a strong coomassie blue protein band on SDS-PAGE gels prepared from the culture induced with IPTG that was absent on SDS-PAGE gels prepared from the culture that was not induced with IPTG. In addition, proteins harvested from the IPTG-induced recombinant E. coli culture were separated by SDS-PAGE, transferred to a nitrocellulose membrane and probed with anti-histidine tag monoclonal antibody. The antibody reacted strongly to a band corresponding to the major coomassie blue protein band. Moreover, the fact that the Bfr protein was found to be present abundantly in the supernate of the E. coli sonicate indicates that the recombinant E. coli expresses F. tularensis Bfr at high level as a soluble protein.

The gene encoding GroEL was amplified from the genomic DNA of F. tularensis RCI and confirmed by nucleotide sequencing. Two different GroEL expressing E. coli BL21 CodonPlus (DE3)-RIL strains were generated, and both strains expressed soluble F. tularensis GroEL at a high level.

The first construct was made by inserting the groEL gene into pET15b and transforming into E. coli BL21 CodonPlus (DE3)-RIL. The pET15b-groEL construct was designed to produce the recombinant GroEL by the E. coli expression host as a fusion protein with 6 histidine residues at its N-terminus. GroEL expression by the recombinant E. coli was tested essentially by the same method described above for Bfr. Expression of the recombinant GroEL with a N-terminal histidine tag was evident from the analysis of an IPTG-induced recombinant E. coli culture by SDS-PAGE and immunoblotting. A predominant protein band corresponding to the molecular mass of GroEL of F. tularensis was observed on the SDS-PAGE gel stained with coomassie blue. Furthermore, this protein band reacted with a monoclonal antibody specific to the histidine tag.

The second construct was made by inserting the groEL gene into pET22b and transforming into E. coli BL21 CodonPlus (DE3)-RIL. The pET22b-groEL construct was designed to produce the recombinant GroEL by the E. coli expression host as a fusion protein with 6 histidine residues at its C-terminus. The recombinant GroEL was expressed abundantly by the E. coli host induced with IPTG. Furthermore, the recombinant protein was able to interact with Ni-NTA resin, the signature feature of a histidine tag.

The gene for Pld was amplified from the genomic DNA of F. tularensis RCI and confirmed by nucleotide sequencing. The pld gene was cloned into the expression vector pET20b immediately downstream of the E. coli pelB leader sequence. The plasmid construct pET20b-pld was transformed into E. coli BL21 CodonPlus (DE3)-RIL. The expression cassette on pET20b is designed to produce the recombinant Pld of F. tularensis as a fusion protein with a histidine tag at its C-terminus and to be exported by the E. coli expression host into the periplasmic space.

A fresh bacterial culture was initiated by inoculating an overnight culture of the recombinant E. coli into LB medium containing 0.8% glucose, carbenicillin and chloramphenicol. The culture was grown at 30° C. for 2 h, and then IPTG was added to the culture to a final concentration of 0.5 mM. The culture was incubated at 30° C. for an additional 5 h before harvesting by centrifugation. The bacterial pellet was sonicated and subjected to analysis by SDS-PAGE and coomassie blue staining. The expression of Pld was apparent by the presence of a major protein band corresponding to the molecular mass of Pld on gels prepared from the soluble fraction of the recombinant *E. coli* culture induced with IPTG. In addition, the recombinant Pld protein exhibited the ability to bind the Ni-NTA affinity column indicating the presence of a histidine tag on the recombinant protein.

The gene coding for DnaK was amplified by PCR from the genomic DNA of *F. tularensis* RCI, and directly cloned into the expression vector pET15b. The sequence coding for DnaK in the expression vector was confirmed by restriction enzyme analysis and nucleotide sequencing. The expression vector for DnaK was then transformed into the *E. coli* expression host BL21 CodonPlus (DE3)-RIL. The expression gene cassette was designed to produce *F. tularensis* DnaK as an N-terminal fusion protein to a short tag of 6-histidine residues followed by a thrombin cleavage site in the *E. coli* expression host. The thrombin site allows the cleavage of the 6-histidine residues from the DnaK protein after purification.

Expression of the *F. tularensis* DnaK in the *E. coli* host was tested similarly as described above for the *F. tularensis* Bfr. Briefly, 1.0 ml of an overnight recombinant *E. coli* culture was inoculated into fresh 25 ml LB medium containing carbenicillin (100 μg/ml). The *E. coli* culture was grown at 37° C., 250 rpm for 1 h before the addition of IPTG to a final concentration of 1 mM. The *E. coli* culture was then allowed to grow for an additional 4 h before harvesting by centrifugation. The bacterial pellet was suspended in lysis buffer for native purification, further lysed by lysozyme and sonication on ice, and centrifuged for 30 min at 10,000×g at 4° C. The resulting supernate and the insoluble pellet were subjected to SDS-PAGE analysis and stained with coomassie blue.

The expression of DnaK was evident by the presence of a strong coomassie blue protein band of ca. 75 kD on gels prepared from the culture induced with IPTG but absent from gels prepared from a duplicate culture not induced by IPTG. In addition, proteins harvested from the recombinant *E. coli* culture induced by IPTG were transferred to a nitrocellulose membrane and probed with anti-histidine tag monoclonal antibody. The antibody reacted strongly to a band corresponding to the major coomassie blue protein band. Moreover, the fact that the DnaK protein was found to be present in abundance in the supernate of the *E. coli* sonicate indicates that the recombinant *E. coli* expresses *F. tularensis* DnaK at high level as a soluble protein.

*E. coli* BL21 CodonPlus (DE3)-RIL expressing *F. tularensis* FabD (Lee et al. 2006). The gene coding for fabD was amplified from the genomic DNA of *F. tularensis* RCI and confirmed by nucleotide sequencing. The fabD gene was cloned into the expression vector pET15b and transformed into *E. coli* BL21 CodonPlus (DE3)-RIL. The gene cassette is designed to produce *F. tularensis* FabD by the *E. coli* expression host as a fusion protein with 6 histidine residues at its N-terminus.

FabD Expression by the recombinant *E. coli* was tested essentially by the same method described above for the Bfr. FabD expression was evident by the presence of a strong coomassie blue protein band corresponding to the molecular mass of *F. tularensis* FabD in both soluble and insoluble fractions prepared from the sonicated recombinant *E. coli*. FabD expression was further confirmed by immunoblotting analysis with an anti-histidine tag monoclonal antibody. The recombinant FabD protein was present in abundance in the soluble bacterial fraction. This result suggested that the recombinant *E. coli* expresses *F. tularensis* FabD at high level as a soluble protein.

The gene coding for SodB was amplified from the genomic DNA of *F. tularensis* RCI and confirmed by nucleotide sequencing. The sodB was cloned into the expression vector pET15b and transformed into *E. coli* BL21 CodonPlus (DE3)-RIL. The gene cassette is designed to produce *F. tularensis* SodB by the *E. coli* expression host as a fusion protein with a tag of 6 histidine residues at its N-terminus.

SodB Expression by the recombinant *E. coli* was tested essentially by the same method described above for Bfr. SodB expression was evident by the presence of a major coomassie blue protein band corresponding to the molecular mass of *F. tularensis* SodB in both the soluble and insoluble fractions prepared from the recombinant *E. coli* culture. SodB expression was further confirmed by immunoblotting analysis with an anti-histidine tag monoclonal antibody. The finding that SodB protein was present abundantly in the soluble bacterial fraction indicated that the recombinant *E. coli* expressed *F. tularensis* SodB at high level as a soluble protein.

Recombinant *E. coli* expressing IglC was cultured in 1 liter of medium with 0.5 mM IPTG for 3 h to induce IglC expression, and the bacteria were harvested by centrifugation. The bacterial pellet was suspended in buffer containing 20 mM HEPES, pH 8.5, 0.5 M NaCl, and 1 mM EDTA and sonicated on ice for a total of 5 cycles, each cycle consisting of 3 min sonication and 7 min rest on ice. The bacterial lysate was centrifuged twice at 12,000 rpm, 4° C. for 30 min to remove insoluble materials and unbroken bacteria. The supernatant was applied to the chitin affinity column. The column was washed extensively to remove unbound bacterial proteins. Proteins bound to the column were eluted sequentially with the same sample loading buffer of decreasing pH, first with pH 7 and second with pH 6.5. When the buffer pH was near or below neutral, the DnaB intein became active and began to cleave itself at the C-terminus. As a result, the recombinant CBD-DnaB intein-IglC protein was separated into two parts: the N-terminal part consisting of chitin binding domain-DnaB intein and the C-terminal part consisting of IglC. Fractions collected from the chitin affinity column were analyzed by SDS-PAGE. The fractions containing significant amounts of IglC were pooled, concentrated, and dialyzed against buffer containing 50 mM Tris, pH7.5. The dialyzed sample was next applied to a Q-Sepharose column with a buffer gradient of increasing NaCl concentration from 0 mM to 500 mM. Fractions collected from the column were analyzed by SDS-PAGE with coomassie blue staining. The IglC containing fractions contained a single protein band of the same molecular mass as that of *F. tularensis* IglC. The amount of the purified IglC product was assayed by the Bradford method and was determined to be 5.8 mg.

The recombinant *E. coli* strain carrying pET22b-katG was cultured in 14 liters of medium and the culture filtrate harvested by centrifugation. The supernatant was passed through a 0.2 μm filter membrane, concentrated, and dialyzed against buffer containing 50 mM Tris, pH7.9 and 150 mM NaCl. The dialyzed culture filtrate was supplemented with NaCl and imidazole to a final concentration of 0.5 M and 5 mM, respectively, and applied to the Ni-NTA affinity column. Proteins bound to the column were eluted first with a linear gradient of imidazole from 5 mM to 100 mM followed by a second linear gradient of imidazole from 100 mM to 500 mM. Fractions collected from the Ni-column were analyzed by SDS-PAGE and staining with coomassie blue. Fractions containing significant amounts of the recombinant KatG were combined, concentrated, and dialyzed against buffer containing 50 mM Tris, pH 7.4. The dialyzed sample was further purified with an ion-exchange column (Q-Sepharose) and two gel filtration columns (Superdex 75 and Sepharcel 400HR). The purified KatG on SDS-PAGE had a major protein band corresponding to the molecular mass of *F. tularensis* KatG and several protein bands of lower molecular mass. The low molecular mass protein bands were presumably the breakdown products of KatG since the antibody specific to KatG of *F. tularensis* recognized not only the major protein band but also the low-molecular-mass protein bands. The yield of the purified recombinant KatG was determined by the Bradford protein assay to be 4.8 mg.

The recombinant *E. coli* strain carrying pET20b-acpA was induced with 0.5 mM IPTG for 4 h at 28° C. in a 4-liter culture and then harvested by centrifugation. The bacterial pellet (26 g wet weight) was suspended in buffer containing 50 mM Tris, pH7.9 with PMSF, a protease inhibitor, and sonicated on ice for a total of 8 cycles. NaCl and imidazole were added to the sonicated bacterial suspension to a final concentration of 0.5 M and 0.5 mM, respectively. The suspension was centrifuged twice at 12,000 rpm, 4° C. for 30 min to remove insoluble materials and unbroken bacteria. The resulting supernatant was filtered through a 0.2 µm membrane and applied to the Ni-NTA affinity column. Fractions collected from the Ni-column were analyzed by SDS-PAGE with coomassie blue staining, and the fractions containing significant amounts of AcpA were pooled. The pooled fractions were dialyzed against PBS and applied to a Q-Sepharose column with a NaCl concentration gradient from 100 mM to 500 mM. The AcpA containing fractions collected from the Q-Sepharose column were assessed by SDS-PAGE with coomassie blue staining and contained a massive band of the same molecular mass as AcpA of *F. tularensis* and numerous protein bands of lower molecular mass, probably the breakdown products of the recombinant AcpA. The amount of purified AcpA was assayed by the Bradford method and was determined to be 83 mg.

Bfr-expressing *E. coli* were induced with 1 mM IPTG for 4.5 h and harvested by centrifugation. The bacterial pellet (15 g wet weight) was suspended in 100 ml of 50 mM Tris buffer, pH7.9 with protease inhibitors and sonicated on ice for a total of 7 cycles; each cycle consisted of 3 min sonication and 7 min rest on ice. NaCl and imidazole were added to the sonicated bacterial suspension to a final concentration of 0.5 M and 0.5 mM, respectively. The suspension was centrifuged twice at 12,000 rpm, 4° C. for 30 min to remove insoluble materials and unbroken bacteria. The resulting supernate was filtered through a 0.2 µm membrane and applied to an affinity column packed with Ni-NTA resin. During the passage, recombinant Bfr with a N-terminal histidine tag was captured by the Ni-column. The column was washed extensively with 50 mM Tris buffer, pH7.9, 0.5 M NaCl, and 5 mM imidazole to remove excess non-recombinant proteins originating from the bacterial host. The proteins bound to the Ni-column were then eluted first with a linear gradient of imidazole from 5 mM to 100 mM followed by a second linear gradient of imidazole from 100 mM to 500 mM. Fractions collected from the Ni-column were analyzed by SDS-PAGE and staining with coomassie blue. Recombinant Bfr appeared to be the dominant protein band in virtually all of the fractions. Fractions containing the most abundant recombinant Bfr were combined, concentrated, and dialyzed against buffer containing 20 mM Tris, pH 8 and 150 mM NaCl. The yield of the recombinant Bfr recovered from the affinity Ni-column purification was determined by the Bradford protein assay to be 65 mg.

A portion of the Ni-column purified recombinant Bfr protein (20 mg) was treated with avidin-thrombin to cleave the N-terminal histidine tag off the recombinant Bfr protein. Thrombin was then captured and removed from the cleavage mixture by incubating with agarose coated with streptavidin, which binds avidin specifically with high affinity. The remaining cleavage mixture was loaded onto the Ni-NTA column a second time. Recombinant Bfr with the histidine-tag removed is unable to bind Ni-NTA resin and therefore passed through the column directly. This purification step efficiently separated the tagless Bfr from any recombinant Bfr with the histidine tag still attached as well as from a few other minor bacterial proteins that were able to bind Ni-NTA resin and thus co-elute with recombinant Bfr in the first round of Ni-affinity column purification. SDS-PAGE analysis of fractions collected from the second Ni-column indicated that these fractions, which contained molecules that passed through the column without binding, contained a single protein corresponding to Bfr. Those fractions were combined and dialyzed extensively against PBS. The amount of Bfr protein in the final preparation was determined by the Bradford protein assay to be 15 mg.

Recombinant *E. coli* expressing *F. tularensis* GroEL with a N-terminal Histidine tag was cultivated (3 liters), induced with IPTG, and sonicated to generate the crude bacterial lysate as described above for Bfr. Recombinant GroEL with a histidine tag at its N-terminus was purified by the affinity Ni-NTA column. Fractions collected from the column were analyzed by SDS-PAGE and staining with coomassie blue. The fractions with highly purified GroEL exhibited a single protein band on the coomassie blue stained gel; these fractions were combined and dialyzed extensively against PBS. The amount of the final recombinant GroEL product was assayed by the Bradford method and was determined to be 26 mg.

Recombinant *E. coli* expressing *F. tularensis* GroEL with a C-terminal Histidine tag was cultivated (4 liters), induced with IPTG, and sonicated to generate the crude bacterial lysate. The lysate containing the recombinant GroEL was first applied to the affinity Ni-NTA column. Fractions collected from the column were analyzed by SDS-PAGE and staining with coomassie blue. The fractions with significant amounts of mostly pure GroEL were combined and dialyzed extensively against 50 mM Tris, pH7.5. The dialyzed recombinant protein was further purified with a Q-Sepharose column with an increasing NaCl gradient from 0 mM to 500 mM. Fractions collected from the column were assessed by SDS-PADE with coomassie blue staining. Fractions containing the pure recombinant protein were pooled, concentrated, and dialyzed extensively against PBS. The amount of the final recombinant GroEL product was assayed by the Bradford method and was determined to be 19.5 mg.

Recombinant *E. coli* carrying pET20b-pld was induced with 0.5 mM IPTG for 5 h in a 4-liter culture and harvested by centrifugation. The bacterial pellet (28 g wet weight) was suspended in buffer containing 50 mM Tris, pH7.9 with PMSF, a protease inhibitor, and sonicated on ice for a total of 8 cycles. The recombinant Pld was purified on a Ni-NTA affinity column and a Q-Sepharose column as described above for AcpA. The purified Pld contained a massive band of the same molecular mass as the Pld of *F. tularensis* and several minor protein bands of lower molecular mass that were most likely breakdown products of Pld as assessed by SDS-PAGE with coomassie blue staining. The amount of purified Pld was assayed by the Bradford method and was determined to be 13.6 mg.

The Dnak protein was isolated and purified from the soluble portion of the recombinant *E. coli* culture. 20 ml LB medium containing carbenicillin (100 µg/ml) and chloramphenicol (50 µg/ml) was inoculated with stocks of the recombinant *E. coli* expressing DnaK and cultured overnight at 37° C., 250 rpm. The 20 ml overnight culture was then inoculated into fresh 1 Liter LB medium containing carbenicillin (100 µg/ml) and grown at 37° C., 250 rpm for 2 h before the addition of IPTG to a final concentration of 1 mM. The recombinant *E. coli* culture was then allowed to grow for an additional 4 h before harvesting by centrifugation. The bacterial pellet was suspended in 10 ml lysis buffer for native purification, lysed for 30 min on ice in the presence of lysozyme, sonicated, and the lysate centrifuged for 30 min at 10,000×g at 4° C. The cleared lysate was then allowed to bind to a Ni-NTA column and the DnaK protein was eluted with elution buffers containing different concentration of imidazole. The N-terminal 6-histidine tag was cleaved from the DnaK protein using a Thrombin cleavage capture kit (Novagen) following the instructions of the manufacturer so that the purified DnaK protein would be free of 6-histidine tags and thrombin enzyme.

The purity of the DnaK protein was confirmed by the presence of a strong coomassie blue protein band that could not be recognized by a monoclonal antibody to the 6-histidine tag by Western blotting.

Recombinant *E. coli* expressing *F. tularensis* FabD protein was cultivated in 6 liters of medium, induced with IPTG, and sonicated to generate the crude bacterial lysate as described above for Bfr. Recombinant FabD with a histidine tag at its N-terminus was purified by the affinity Ni-NTA column. Fractions containing significant amounts of relatively pure FabD as assessed by coomassie blue stained SDS-PAGE were pooled, concentrated, and dialyzed against buffer containing 20 mM Tris, pH 8 and 150 mM NaCl. The yield of the recombinant FabD recovered from the affinity Ni-column purification was determined by the Bradford protein assay to be 66 mg.

The Ni-column purified recombinant FabD protein (60 mg) was treated with avidin-thrombin to cleave off its N-terminal histidine tag and then purified further by the same procedures described above. The purified FabD appeared to have a single protein band as assessed by SDS-PAGE. The amount of FabD protein after the final purification was assayed by the Bradford method and was determined to be 47 mg.

Recombinant *E. coli* expressing *F. tularensis* SodB was cultivated in 6 liters of medium, induced with IPTG, and sonicated to generate the crude bacterial lysate as described above for Bfr. Recombinant SodB with a histidine tag at its N-terminus was purified by the affinity Ni-NTA column. Fractions containing significant amounts of relatively pure SodB as assessed by coomassie blue stained SDS-PAGE were pooled, concentrated, and dialyzed against buffer containing 20 mM Tris, pH 8 and 150 mM NaCl. The yield of the recombinant SodB recovered from the affinity Ni-column purification was determined by the Bradford protein assay to be 105 mg.

A portion of the Ni-column purified recombinant SodB protein (20 mg) was treated with avidin-thrombin to cleave off its N-terminal histidine tag and then purified further by the same procedures described above. The purified SodB appeared to have a single protein band as assessed by SDS-PAGE. The amount of SodB protein after the final purification was assayed by the Bradford method and was determined to be 15 mg.

To assess whether culture filtrate proteins of *F. tularensis* are targets of the host immune system during a natural infection, mice were infected with *F. tularensis* LVS by the intradermal route and at 5, 9, and 15 weeks post-infection, T-cell proliferation was assayed against *F. tularensis* culture filtrate proteins (KatG, GroEL, FabD, SodB, and Bfr) that were purified to homogeneity from recombinant *E. coli*. Control mice were immunized with heat-killed LVS or sham-immunized (injected with saline only).

Specific-pathogen free 6-8-week old female Balb/C mice from Charles River Laboratories, in groups of 3 were immunized intradermally (i.d.) or intravenously (i.v.) twice, 5 weeks apart, with 20 µg *F. tularensis* protein antigen purified from *E. coli* in the adjuvant SAF (Syntex Adjuvant Formulation) or with $10^6$ CFU of live attenuated recombinant *L. monocytogenes* expressing *F. tularensis* protein antigens as listed below:

Group 1: Buffer/Adjuvant Control (0.9% NaCl with SAF adjuvant), abbreviated Sham, i.d.
Group 2: *F. tularensis* Live vaccine strain (LVS), i.d.
Group 3: AcpA purified from *E. coli* with SAF adjuvant, abbreviated AcpA, i.d.
Group 4: Bfr purified from *E. coli* with SAF adjuvant, abbreviated Bfr, i.d.
Group 5: GroEL purified from *E. coli* with SAF adjuvant, abbreviated GroEL, i.d.
Group 6: IglC purified from *E. coli* with SAF adjuvant, abbreviated IglC, i.d.
Group 7: KatG purified from *E. coli* with SAF adjuvant, abbreviated KatG, i.d.
Group 8: Pld purified from *E. coli* with SAF adjuvant, abbreviated Pld, i.d.
Group 9: Vector Control (Parental *L. monocytogenes* with ActA deletion), abbreviated Lm/ΔactA, i.d.
Group 10: Lm/ΔactA expressing *F. tularensis* AcpA, abbreviated Lm/AcpA, i.d.
Group 11: Lm/ΔactA expressing *F. tularensis* Bfr, abbreviated Lm/Bfr, i.d.
Group 12: Lm/ΔactA expressing *F. tularensis* GroEL, abbreviated Lm/GroEL, i.d.
Group 13: Lm/ΔactA expressing *F. tularensis* IglC, abbreviated Lm/IglC, i.d.
Group 14: Lm/ΔactA expressing *F. tularensis* KatG, abbreviated Lm/KatG, i.d.
Group 15: Lm/ΔactA expressing *F. tularensis* Pld, abbreviated Lm/Pld, i.d.
Group 16: Lm/ΔactA, i.v.
Group 17: Lm/AcpA, i.v.
Group 18: Lm/Bfr, i.v.
Group 19: Lm/GroEL, i.v.
Group 20: Lm/IglC, i.v.
Group 21: Lm/KatG, i.v.
Group 22: Lm/Pld, i.v.

Nine weeks after the first immunization, mice were anaesthetized with Isoflurane and spleens were removed. A single cell suspension of splenocytes was prepared. Red cells were lysed with 1× PharmLyse (BD Biosciences). Splenocytes were incubated with or without *F. tularensis* protein antigens and allowed to proliferate for 48 hours. The amount of lymphocyte proliferation was detected by adding radioactive $^3$H (tritiated) thymidine for 2 hours, which was incorporated into the newly synthesized DNA of the dividing cells. The amount of radioactivity incorporated into DNA was measured in a scintillation counter and is proportional to the number of proliferating cells, which in turn is a function of the number of lymphocytes that were stimulated by a given antigen to proliferate.

Figure 2:
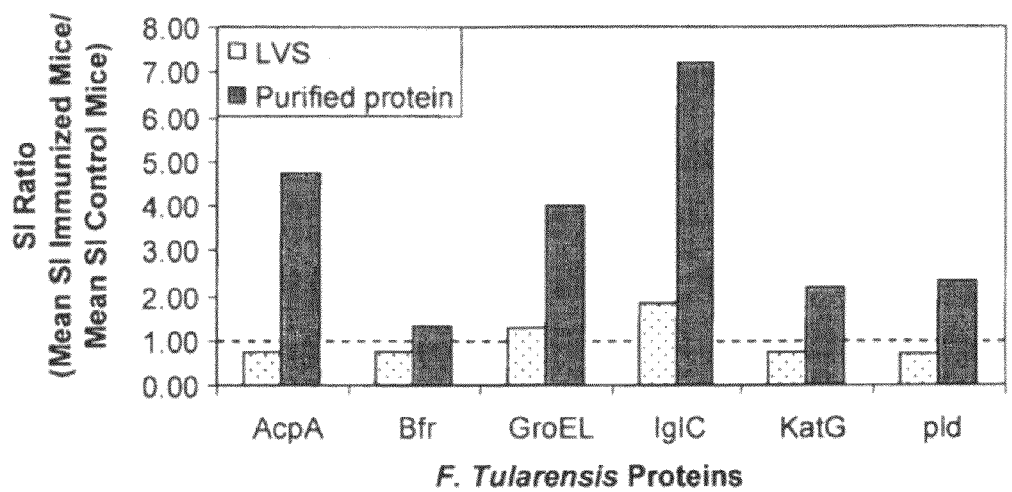
FIG. 2A-B shows the immunogenicity of *F. tularensis* protective antigens. (A) Balb/c mice were sham-immunized or immunized intradermally twice with purified *F. tularensis* proteins at weeks 0 and 5. (B) Balb/c mice were immunized intradermally or intravenously twice with the recombinant *L. monocytogenes* expressing *F. tularensis* proteins at weeks 0 and 5. Mice immunized once with LVS at week 0 served as a control in both A and B. Spleen cells were harvested at week 9, cultured in vitro in the presence or absence of 10 µg/ml of the corresponding *F. tularensis* protein for 48 h as shown on the horizontal scale of the graphs, and pulsed with 0.25 µCi of [$^3$H]thymidine/ml for 3 h. The Stimulation Index (SI) for triplicate wells was then computed and was equal to the mean CPM in the presence of the corresponding protein divided by the mean CPM in the absence of protein. The SIs for three mice per group were then averaged and then the ratio of the mean SI for immunized mice to the mean SI for Control mice was computed as follows. For mice immunized with purified proteins or with LVS, the ratio was equal to the mean SI of mice immunized with the purified protein or with LVS divided by the mean SI for sham-immunized mice. For mice immunized with attenuated *L. monocytogenes* expressing *F. tularensis* proteins, the ratio was equal to the mean SI for mice immunized with attenuated *L. monocytogenes* expressing the *F. tularensis* protein divided by the mean SI for mice immunized with the empty vector. Hence, values larger than 1 (as shown by a dashed line in each graph) indicate positive immunogenicity elicited by the specific vaccines vs. controls.
Figure 2:
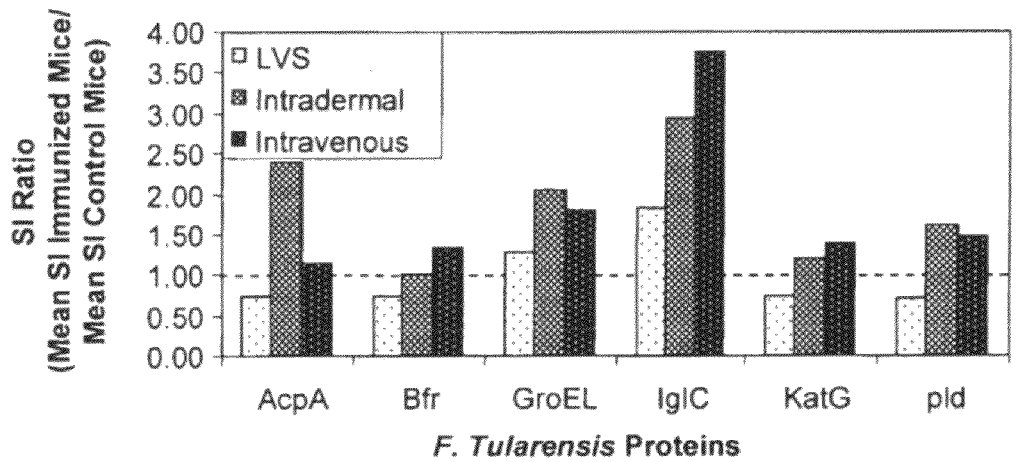
Figure 3:
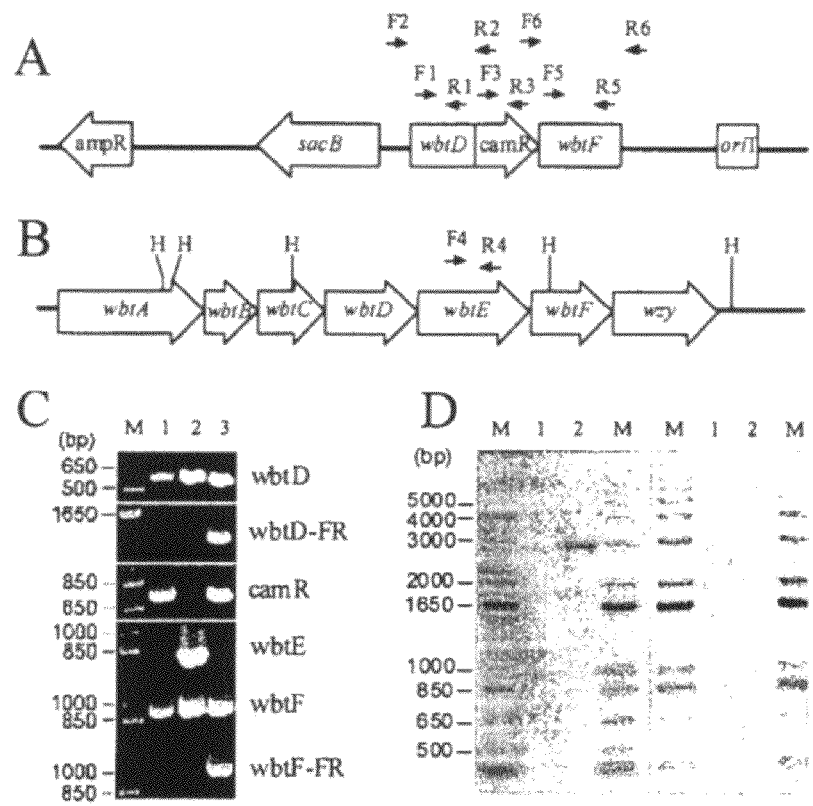
FIG. 3A-D shows generation and confirmation of the LVS ΔwbtDEF mutant. (A) The 8.9 kb suicide plasmid, pSMP22::wbtDEFΔ contains the 3' two-thirds of the wbtD gene with no stop codon, a frameshifted wbtF gene missing both the start and stop codons and a chloramphenicol resistant gene cassette inserted in between the mutated wbtD and wbtF genes. Location of each of the primer pairs used for amplification of the various regions on the plasmid vector or the chromosome is indicated. (B) Genetic organization of a portion (9 kb) of the *F. tularensis* LVS O-antigen gene cluster (17 kb). H, HindIII. (C) PCR analysis of the LVS ΔwbtDEF mutant (lane 1), the parental LVS strain (lane 2), and the suicide plasmid, pSMP22::wbtDEFΔ (lane 3). M, 1-kb plus DNA ladder in basepairs (bp). Primer pairs used for PCR amplification of wbtD, cat (the gene confers chloramphenicol resistance; camR) and wbtF genes are F1/R1, F3/R3 and F5/R5, depicted in (A), respectively. Primer pairs used for PCR amplification of the wbtD and wbtF genes from their respective flanking regions on the suicide plasmid are F2/R2 and F6/R6, depicted in (A). Primer pairs used for PCR amplification of the wbtE gene are F4/R4, depicted in (A). (D) Southern hybridization analysis of the HindIII-digested genomic DNA of the LVS ΔwbtDEF mutant (lane 1) and the parental LVS strain (lane 2). Left Panel: A 3-kb HindIII genomic DNA fragment was detected with an oligonucleotide probe to wbtE in the parental LVS strain but not in the ΔwbtDEF mutant. Right Panel: A 2.5-kb HindIII genomic DNA fragment was detected with an oligonucleotide probe to the cat cassette in the ΔwbtDEF mutant but not in the parental LVS strain. M, biotin-labeled 1-kb plus DNA ladder.

All of the six *F. tularensis* proteins (AcpA, Brf, GroEL, IglC, KatG and Pld) elicited strong immune responses in mice against the proteins tested when compared with the sham or LVS-immunized animals (FIG. 2A).

All of the six proteins delivered by attenuated *L. monocytogenes* administered intradermally or intravenously induced strong immune responses in mice against the relevant protein compared with the immune responses in mice immunized with the vector or with LVS (FIG. 2B).

In comparison with T-cells from sham-immunized mice, T-cells from mice infected with live LVS proliferated strongly in response to the culture filtrate proteins of *F. tularensis*. Stimulation indices for T-cell proliferation reached statistical significance for Bfr, GroEL and KatG. In contrast, T-cells from mice immunized with heat-killed LVS proliferated marginally in response to culture filtrate proteins. Moreover, Bfr, GroEL and KatG stimulated IFN-γ secretion from both CD4 and CD8 T-cells in mice immunized with live LVS but stimulated little IFN-γ secretion in mice immunized with the heat-killed bacteria. These results indicate that during an infection the culture filtrate proteins are actively produced by the live bacterium and are processed and presented by the infected cells to the host immune system. The fact that Bfr, GroEL and KatG stimulate functional CD4 and CD8 T-cell responses suggests that these protein antigens are promising candidates for inclusion in a vaccine.

Specific-pathogen free 6-8-week old female Balb/C mice from Charles River Laboratories, in groups of 8, were immunized intradermally twice, 4 weeks apart, with 20 μg *F. tularensis* protein antigens purified from *E. coli* in 50 μL adjuvant (SAF) or with $10^6$ CFU of recombinant attenuated *L. monocytogenes* expressing *F. tularensis* protein antigens as listed below:

Group 1: Buffer/Adjuvant Control (0.9% NaCl with SAF adjuvant), abbreviated Sham.
Group 2: *F. tularensis* Live vaccine strain (LVS).
Group 3: AcpA purified from *E. coli* with SAF adjuvant, abbreviated AcpA.
Group 4: Bfr purified from *E. coli* with SAF adjuvant, abbreviated Bfr.
Group 5: DnaK purified from *E. coli* with SAF adjuvant, abbreviated DnaK.
Group 6: GroEL purified from *E. coli* with SAF adjuvant, abbreviated GroEL.
Group 7: IglC purified from *E. coli* with SAF adjuvant, abbreviated IglC.
Group 8: KatG purified from *E. coli* with SAF adjuvant, abbreviated KatG.
Group 9: Pld purified from *E. coli* with SAF adjuvant, abbreviated Pld.
Group 10: Vector Control (Parental *L. monocytogenes* with actA deletion), abbreviated Lm/ΔactA or Lm.
Group 11: Lm/ΔactA expressing *F. tularensis* AcpA, abbreviated Lm/AcpA.
Group 12: Lm/ΔactA expressing *F. tularensis* Bfr, abbreviated Lm/Bfr.
Group 13: Lm/ΔactA expressing *F. tularensis* GroEL, abbreviated Lm/GroEL.
Group 14: Lm/ΔactA expressing *F. tularensis* IglC, abbreviated Lm/IglC.
Group 15: Lm/ΔactA expressing *F. tularensis* KatG, abbreviated Lm/katG.
Group 16: Lm/ΔactA expressing *F. tularensis* Pld, abbreviated Lm/Pld.

Eight weeks after the 1st immunization, mice were challenged intranasally with 100 $LD_{50}$ ($3 \times 10^6$ CFU/mouse) in a total volume of 20 μl. The mice were then observed for 3 weeks for illness and death.

Protective Immunity Results

TABLE 2

| Groups (8 mice/group) | Vaccines | Number Mice Surviving | Survival Rate (%) | For Non-survivors, Median Time to Death (Days) |
|---|---|---|---|---|
| 1 | Sham | 2 | 25 | 5.5 |
| 2 | LVS | 8 | 100 | — |
| 3 | AcpA | 5 | 62.5 | 6 |
| 4 | Bfr | 4 | 50 | 9 |
| 5 | DnaK | 3 | 37.5 | 10 |
| 6 | GroEL | 4 | 50 | 9 |
| 7* | IglC | 3 | 37.5 | 9 |
| 8 | KatG | 5 | 62.5 | 11 |
| 9 | Pld | 3 | 37.5 | 8 |
| 10 | Lm/ΔactA | 2 | 25 | 9 |
| 11 | Lm/AcpA | 0 | 0 | 10.5 |
| 12 | Lm/Bfr | 4 | 50 | 7 |
| 13 | Lm/DnaK | 2 | 25 | 7.5 |
| 14 | Lm/GroEL | 2 | 25 | 10 |
| 15* | Lm/IglC | 6 | 75 | 10.5 |
| 16 | Lm/KatG | 5 | 62.5 | 10 |
| 17 | Lm/Pld | 4 | 50 | 10 |

*N.B. In contrast to mice in other groups, mice surviving in these groups showed little or no illness after challenge.

In animals immunized with purified proteins (Groups 3-9), all animals had greater survival than sham-immunized animals. In animals immunized with recombinant *L. monocytogenes* (Groups 11-17), the animals immunized with *L. monocytogenes* expressing Bfr, IglC, KatG, or Pld showed greater survival than the animals immunized with the vector control (Group 10). Although the animals immunized with *L. monocytogenes* expressing AcpA, DnaK, or GroEL did not show greater survival than the animals immunized with the vector control, the median time to death was greater for these animals than for the sham-immunized controls, indicating some protection. Moreover, the animals immunized with the vector control survived longer than the sham immunized animals, indicating that the vector control itself may have offered some protection against *F. tularensis* challenge. This was confirmed in a subsequent experiment (see below)

Specific-pathogen free 6-8-week old female Balb/C mice from Taconic (Hudson, N.Y.), in groups of 8, were immunized intradermally once at 0 or 4 weeks, or immunized twice at both 0 and 4 weeks as described in Table 2. Recombinant *L. monocytogenes* was administered at a dose of $10^6$ CFU for each strain. *F. tularensis* LVS was administered at the maximum tolerated dose of 104 CFU. Proteins were administered at a dose of 20 μg in 50 μL SAF. A separate control group of animals (Group 21) was unimmunized. At week 8, the mice were challenged intranasally with a super lethal dose of $6 \times 10^6$ CFU *F. tularensis* LVS (~100 $LD_{100}$) as shown in Table 3:

TABLE 3

| Group # | Vaccines (1st // 2nd) | 1st immunization (I.D.) Week 0 | 2nd immunization (I.D.) Week 4 | Challenge (I.N.) Week 8 |
|---|---|---|---|---|
| 1 | LVS | LVS | — | LVS (~100 $LD_{100}$) |
| 2 | Lm/ΔactA vector control | Lm/ΔactA | — | LVS (~100 $LD_{100}$) |
| 3 | Lm/IglC | Lm/IglC | — | LVS (~100 $LD_{100}$) |
| 4 | Lm/KatG | Lm/KatG | — | LVS (~100 $LD_{100}$) |
| 5 | Lm/IglC + Lm/KatG | Lm/IglC + Lm/KatG | — | LVS (~100 $LD_{100}$) |
| 6 | Lm/ΔactA vector control | — | Lm/ΔactA | LVS (~100 $LD_{100}$) |
| 7 | Lm/IglC | — | Lm/IglC | LVS (~100 $LD_{100}$) |
| 8 | Lm/katG | — | Lm/KatG | LVS (~100 $LD_{100}$) |
| 9 | Lm/IglC + Lm/katG | — | Lm/IglC + Lm/KatG | LVS (~100 $LD_{100}$) |
| 10 | Lm/ΔactA vector control | Lm/ΔactA | Lm/ΔactA | LVS (~100 $LD_{100}$) |
| 11 | Lm/IglC | Lm/IglC | Lm/IglC | LVS (~100 $LD_{100}$) |
| 12 | Lm/KatG | Lm/KatG | Lm/KatG | LVS (~100 $LD_{100}$) |
| 13 | Lm/IglC + Lm/KatG | Lm/IglC + Lm/KatG | Lm/IglC + Lm/KatG | LVS (~100 $LD_{100}$) |
| 14 | Lm/ΔactA vector control // Adjuvant control | Lm/ΔactA | SAF 50 μL | LVS (~100 $LD_{100}$) |
| 15 | Lm/ΔactA vector control // IglC | Lm/ΔactA | IglC 20 μg | LVS (~100 $LD_{100}$) |
| 16 | Lm/ΔactA vector control // KatG | Lm/ΔactA | KatG 20 μg | LVS (~100 $LD_{100}$) |
| 17 | Lm/ΔactA vector control // IglC + KatG | Lm/ΔactA | IglC 20 μg + KatG 20 μg | LVS (~100 $LD_{100}$) |
| 18 | Lm/IglC // IglC | Lm/IglC | IglC 20 μg | LVS (~100 $LD_{100}$) |
| 19 | Lm/KatG // KatG | Lm/KatG | KatG 20 μg | LVS (~100 $LD_{100}$) |
| 20 | Lm/KatG + Lm/IglC //IglC + KatG | Lm/KatG + Lm/IglC | IglC 20 μg + KatG 20 μg | LVS (~100 $LD_{100}$) |
| 21 | Unimmunized Control | — | — | LVS (~100 $LD_{100}$) |

Protective Immunity Results

TABLE 4

| Groups (8mice/group) | Vaccines | No. Immunizations | Immunization Week | Number Survivors | Survival Rate (%) | For Non-survivors, Median Time to Death (Days) |
|---|---|---|---|---|---|---|
| 21 | Unimmunized Control | 0 | — | 0 | 0 | 4.5 |
| 1 | LVS | 1 | 0 | 3 | 37.5 | 5 |
| 2 | Lm/ΔactA vector control (Lm) | 1 | 0 | 3 | 37.5 | 7.5 |
| 3 | Lm/IglC | 1 | 0 | 3 | 37.5 | 6.5 |
| 4 | Lm/KatG | 1 | 0 | 2 | 25 | 8.5 |
| 5 | Lm/IglC + Lm/KatG | 1 | 0 | 3 | 37.5 | 6.5 |
| 6 | Lm/ΔactA vector control | 1 | 4 | 4 | 50 | 8 |
| 7 | Lm/IglC | 1 | 4 | 5 | 62.5 | 9.5 |
| 8 | Lm/KatG | 1 | 4 | 5 | 62.5 | 5.5 |
| 9 | Lm/IglC + Lm/IglC | 1 | 4 | 5 | 62.5 | 8 |
| 10 | Lm/ΔactA vector control | 2 | 0, 4 | 5 | 62.5 | 4.5 |
| 11 | Lm/IglC | 2 | 0, 4 | 6 | 75 | 4.5 |
| 12 | Lm/KatG | 2 | 0, 4 | 6 | 75 | 2 |
| 13 | Lm/IglC + Lm/KatG | 2 | 0, 4 | 8 | 100 | — |
| 14 | Lm/ΔactA vector control // Adjuvant control | 2 | 0, 4 | 4 | 50 | 5.5 |
| 15 | Lm/ΔactA vector control // IglC | 2 | 0, 4 | 5 | 62.5 | 8 |
| 16 | Lm/ΔactA vector control | 2 | 0, 4 | 6 | 75 | 12 |

TABLE 4-continued

| Groups (8mice/ group) | Vaccines | No. Immunizations | Immunization Week | Number Survivors | Survival Rate (%) | For Non-survivors, Median Time to Death (Days) |
|---|---|---|---|---|---|---|
| 17 | // KatG Lm/ΔactA vector control // IglC + KatG | 2 | 0, 4 | 5 | 62.5 | 6 |
| 18 | Lm/IglC // IglC | 2 | 0, 4 | 6 | 75 | 12.5 |
| 19 | Lm/KatG // katG | 2 | 0, 4 | 5 | 62.5 | 5.5 |
| 20 | Lm/IglC + Lm/KatG // IglC + KatG | 2 | 0, 4 | 6 | 75 | 7.5 |

All immunized groups showed greater survival than unimmunized controls (group 21), which had no survivors. Hence, all vaccines offered some protection. LVS administered once at the maximum tolerated dose gave only 37.5% protection (group 1).

Animals immunized once at week 0 with a recombinant L. monocytogenes strain expressing either IglC (group 3) or a combination of recombinant L. monocytogenes strains expressing IglC and KatG (group 5) showed protection comparable to animals immunized with LVS. Animals immunized once at week 0 with the recombinant L. monocytogenes strain expressing KatG (group 4) showed slightly less survival than animals immunized with LVS, but the median time to death was considerably longer. Interestingly, animals immunized once at week 0 with the vector control (group 2) showed greater survival than unimmunized animals (group 21), and survival comparable to LVS-immunized animals, confirming that the vector control alone has some protective capacity.

Animals immunized once at week 4 with recombinant L. monocytogenes strains expressing IglC or KatG, or IglC and KatG (groups 7-9) all had greater survival than animals immunized with either the vector control (group 6) or LVS. Again, animals immunized once at week 4 with the vector control showed greater survival than both the LVS and unimmunized animals, again confirming that the vector control alone has some protective capacity.

Animals immunized twice at Weeks 0 and 4 with recombinant L. monocytogenes strains expressing IglC or KatG, or IglC and KatG (groups 11-13) showed a high level of protection. All these groups had greater survival than the animals immunized twice with the vector control (group 10), or the animals immunized with LVS or the unimmunized animals. Animals immunized twice with the vector control also had better survival than animals immunized with LVS or unimmunized animals, and moreover, the median time to death was longer. Impressively, animals immunized twice with the recombinant L. monocytogenes strains expressing IglC and KatG (group 13) had 100% survival.

Animals immunized at week 0 with the vector control and at week 4 with purified protein (IglC or KatG or the combination of IglC and KatG) (groups 15-17) showed greater survival than animals immunized with the vector control at week 0 and sham-immunized at week 4 with adjuvant only (group 14), showing that immunization with these proteins is protective. The animals immunized at week 0 with the vector control and at week 4 with purified protein (IglC or KatG or the combination of IglC and KatG) (groups 15-17) also showed greater survival than animals immunized with LVS and unimmunized animals.

Animals primed by immunization at week 0 with recombinant L. monocytogenes expressing IglC or KatG or both of these strains and then boosted at week 4 with the relevant protein (IglC or KatG or the combination of IglC and KatG, resp.) (groups 18-20) showed better survival than animals primed with the same strain at week 0 but not later boosted (Groups 3-5). Animals primed by immunization at week 0 with recombinant L. monocytogenes expressing IglC or KatG or both of these strains and then boosted at week 4 with the relevant protein (IglC or KatG or the combination of IglC and KatG, resp.) also showed better survival than animals primed with the vector control and sham-boosted (Group 14). Animals primed by immunization at week 0 with recombinant L. monocytogenes expressing IglC or KatG or both of these strains and then boosted at week 4 with the relevant protein (IglC or KatG or the combination of IglC and KatG, resp.) showed better survival than animals immunized with LVS or unimmunized animals (Groups 1 and 21, resp.).

Figure 4:
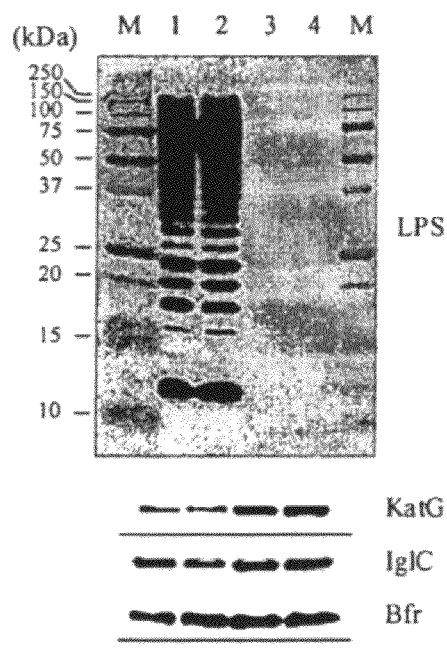
FIG. 4 shows disruption of O-antigen biosynthesis in the O-antigen deficient LVS mutants. Whole cell lysates from the parental LVS strain (lane 1) and ΔwbtDEF mutant (lane 4) were subjected to immunoblot analysis using monoclonal antibody FB11 specific to *F. tularensis* LVS or polyclonal antibodies to *F. tularensis* proteins KatG, IglC and Bfr. M, all blue precision plus protein standards in kilodaltons. Lanes 2 and 3 are other *F. tularensis* strains.

Characterization of F. tularensis LVS O-antigen deficient mutant. Genomic DNA isolated from the parental LVS strain and the ΔwbtDEF mutant (FtLVSΔOAg) as well as the suicide plasmid DNA by PCR and Southern hybridization was analyzed. Unlike the parental LVS strain, there was no PCR product amplified from the ΔwbtDEF mutant genomic DNA using a pair of primers designed specifically for the wbtE gene. Similarly unlike the suicide plasmid, there was no PCR product for the wbtD or the wbtF gene when amplified from the primers annealing to the immediate 5' and 3' flanking regions of the suicide plasmid. These results indicate that, as expected, two homologous recombination events occurred in the mutant. Southern hybridization analysis confirmed chromosomal integration of the cat gene and loss of the wbtE gene in the LVS ΔwbtDEF mutant (FtLVSΔOAg) (FIG. 3).

Immunodetection of O-antigen and proteins in the LVS ΔwbtDEF mutant strain (FtLVSΔOAg). The disruption of O-antigen biosynthesis in the LVS ΔwbtDEF mutant was assessed by immunoblot analysis using a monoclonal antibody specific to *F. tularensis* LPS. A typical ladder pattern of LPS dictated by the number of O-antigen repeat units present in the molecules from the parental LVS strain but not from the ΔwbtDEF mutant was detected. The absence of O-antigen signals from the ΔwbtDEF mutant was not due to inadequate sample loading since similar intensities of the catalase-peroxidase (KatG), intracellular growth locus C (IglC) and bacterioferritin (Bfr) signals for the LVS parental and the Δwbt- DEF mutant strains were detected (FIG. 4). This result demonstrates that the ΔwbtDEF mutant is O-antigen deficient.

In general, O-antigen deficient bacterial mutants become sensitive to complement-mediated killing. Without the protection of O-antigen, serum complement fixes onto the surface of the bacterial mutants and leads to bacterial lysis. C7 deficient serum allows fixation of complement factor C3 on the surface of the bacteria, but not the formation of a terminal attack complex. Bacteria were incubated with either normal or C7 deficient human serum for 10 min at 37° C., and then serially diluted and plated on agar plates. Whereas the parental LVS strain was resistant to lysis mediated by serum complement, the O-antigen deficient strain suffered 4 logs of killing by 10 min incubation in serum containing an intact complement pathway (Table 5). This result demonstrates that the LVS ΔwbtDEF mutant is highly sensitive to complement-mediated killing.

TABLE 5

| Strain | Serum | CFU/mL ± Standard Deviation |
|---|---|---|
| LVS | C7 deficient | $5.8 \times 10^7 \pm 6.4 \times 10^6$ |
| LVS | Normal serum | $7.0 \times 10^7 \pm 6.4 \times 10^6$ |
| LVSΔwbtDEF | C7 deficient | $5.8 \times 10^7 \pm 1.3 \times 10^7$ |
| LVSΔwbtDEF | Normal serum | $5.0 \times 10^3 \pm 7.1 \times 10^3$ |

Figure 5:
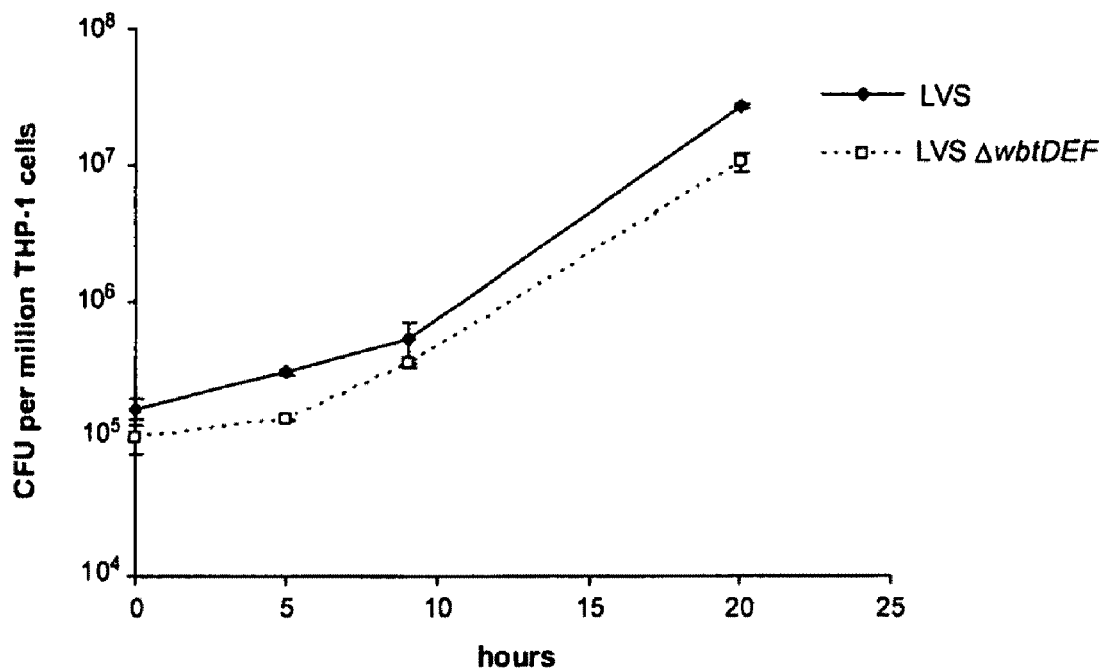
FIG. 5 is a graph showing growth of *F. tularensis* LVS and the O-antigen deficient mutant in monolayers of human macrophages. Bacteria were pre-opsonized with C7 deficient serum and centrifuged onto the THP-1 monolayers at 1000×g for 30 min at 4° C. The THP-1 monolayers were incubated at 37° C. for 90 min to allow uptake of the bacteria, washed to remove extracellular bacteria, and incubated in culture medium containing gentamicin (0.1 µg/ml). Under these conditions, there is no growth of the bacteria in the culture medium in the absence of THP-1 cells. At sequential times after infection, the culture supernate was removed and the macrophage monolayers were scraped and disrupted with glass beads by vortexing 10 times with 2 second pulses each time. The numbers of bacteria per monolayer was determined by plating serial dilutions on chocolate agar.

Because *F. tularensis* is an intracellular bacterium that infects and multiplies in macrophages, the necessity of the O-antigen for the bacterial growth in human macrophages was examined. THP-1 cells were infected with parental LVS or ΔwbtDEF mutant strain pre-opsonized with C7 deficient serum and determined the number of intracellular bacteria over time. Although there was a delay in the growth of the LVS ΔwbtDEF mutant compared with the parental LVS strain during the first 9 hours, the mutant eventually grew with a doubling time of 2 hours that matched that of the parental LVS strain (FIG. 5). This result demonstrates that the O-antigen deficient mutant is capable of intracellular multiplication and that it multiplies almost as well as the parental LVS strain. Thus, the O-antigen is not critical for bacterial growth in human macrophages.

Using the O-antigen deficient LVS mutant as a parental strain, an O-antigen deficient LVS mutant over-expressing the virulent *F. tularensis* antigen IglC was generated. The LVS mutant deficient in O-antigen is attenuated, however it does not provide protection against virulent *F. tularensis* subspecies *tularensis* challenge. To improve the immunoprotectivity of the O-antigen deficient LVS mutant, an O-antigen deficient LVS mutant over-expressing the virulent *F. tularensis* subsp. *tularensis* antigen IglC was generated.

The gene for virulent *F. tularensis* IglC was PCR amplified from *F. tularensis* subspecies *tularensis* RCI genomic DNA and cloned into the downstream of the *F. tularensis* GroE operon promoter in a transfer vector pFNLTP6, which contained a kanamycin resistant gene and was engineered to grow in *F. tularensis* LVS, *F. novicida* 112 and in *E. coli* (Maier, Havig et al. 2004). The resultant plasmid with the insertion of an expression cassette for virulent *F. tularensis* IglC, pFNLTP6/pGro-iglC, was electroporated into the O-antigen deficient LVS mutant. The bacteria mixture was selected on chocolate agar containing kanamycin (10 μg ml$^{-1}$). The parental O-antigen-deficient LVS mutant is sensitive to kanamycin and therefore cannot grow in the presence of kanamycin. Under the selective pressure of kanamycin, only LVS mutants carrying the transfer vector pFNLTP6/pGro-iglC were able to grow on the chocolate agar containing kanamycin (10 μg ml$^{-1}$). After 3 days incubation, the colonies were screened by PCR amplification using two pairs of primers. The first pair was designed to anneal to the 3' end of the GroE promoter and the 5' end of iglC coding sequence, which would amplify a PCR product of approximately 670 bp from the LVS mutant carrying the transfer vector. As expected, a 670-bp PCR product was amplified from the selected LVS mutants, but was missing from the parental LVS strain. The second pair of primers was designed to anneal specifically to the 5' and 3' ends of the GroE promoter, which would generate a 421-bp PCR product from the parental transfer vector pFNLTP6 and 1035 bp PCR product from the transfer vector with the IglC expression cassette. As expected, the selected LVS strains generated a PCR product of 1035 bp. These results indicated that the selected O-antigen deficient LVS strain contained the transfer vector pFNLTP6/pGro-iglC. The selected strain was named FtLVSΔOAg/IglC.

The gene for virulent *F. tularensis* AcpA was PCR amplified from *F. tularensis* subspecies *tularensis* RCI genomic DNA and cloned into the transfer vector pFNLTP6, as described above for pFNLTP6/pGro-iglC. The resultant plasmid, pFNLTP6/pGro-acpA was electroporated into the *F. tularensis* LVS strain. The LVS strains containing the transfer vector, pFNLTP6/pGro-acpA, were selected and confirmed as described above for FtLVSΔOAg/IglC mutant. The resultant LVS strain was named FtLVS/AcpA.

Recombinant LVS over-expressing virulent Bfr. The strain, designated FtLVS/Bfr, was constructed in a way similar to that of FtLVS/AcpA.

Recombinant LVS over-expressing virulent DnaK. The strain, designated FtLVS/Dnak, was constructed in a way similar to that of FtLVS/AcpA.

Recombinant LVS over-expressing virulent GroEL. The strain, designated FtLVS/GroEL, was constructed in a way similar to that of FtLVS/AcpA.

Recombinant LVS over-expressing virulent IglC. The strain, designated FtLVS/IglC, was constructed in a way similar to that of FtLVS/AcpA.

Growth kinetics and protein expression profiles of recombinant *F. tularensis* LVS strains over-expressing virulent *F. tularensis* antigens. The growth kinetics of the LVS strains and the protein expression profiles in these LVS strains were examined in defined Chamberlain medium. The recombinant LVS strain carrying each of these plasmids grew similarly to the parental LVS strain in defined Chamberlain medium. The expression levels of AcpA, Bfr, and IglC were higher in LVS strains carrying the corresponding plasmid than in the parental LVS strain.

*F. tularensis* Tul4, encoded by lpnA, is a membrane lipoprotein and conserved among *F. tularensis* strains. The gene encoding the mature peptide of Tul4 was amplified from the *F. tularensis* RCI genomic DNA and cloned into pZErO vector. The identity of the inserted Tul4 coding sequence was confirmed by nucleotide sequencing. The Tul4 coding sequence was then subcloned into the BamHI and PacI sites of pKB199, in such a way that the Tul4 coding sequence was fused to the hemolysin signal sequence downstream of the hemolysin promoter of *L. monocytogenes*. The expression cassette of the hly-tul4 fusion protein driven by the hemolysin promoter was excised from the resultant vector and subsequently cloned into a site-specific integration vector pDP4189. The integration vector was transformed into SM10, the *E. coli* conjugation donor strain. The conjugation and selection of recombinant *L. monocytogenes* expressing Tul4 was performed as described for recombinant *L. monocytogenes* expressing IglC.

Recombinant protein expression in macrophage-like cell lines. The intracellular expression of IglC and KatG by the attenuated recombinant *L. monocytogenes* strains was examined in human macrophage-like THP-1 cells (ATCC TIB-202). THP-1 cells were maintained in RPMI supplemented with 10% FBS, penicillin and streptomycin. For infection, THP-1 cells were differentiated into a macrophage monolayer in 24-well plates ($2 \times 10^5$ cells/well) in the presence of 10 nM PMA (phorbol 12-myristate 13-acetate) and the absence of antibiotics. The recombinant *L. monocytogenes* strains were grown to late logarithmic phase (optical density at 540 nm, 1.0) in Brain Heart Infusion broth. The bacterial culture was then used to infect the THP-1 cell monolayer at an MOI of 50:1. After infection for 1 h at 37° C., the monolayer was washed twice with RPMI before the addition of 1 ml medium containing gentamicin (10 µg ml$^{-1}$) to kill any remaining extracellular bacteria. At 24 hours post infection, cells were harvested, washed once with PBS and lysed in Laemmli buffer. Cell extracts were boiled for 7 min before they were loaded on an SDS PAGE gel. The intracellular expression of IglC and KatG by the recombinant *L. monocytogenes* strains was confirmed by Western blot analysis using a polyclonal antibody to the relevant protein. A single protein band of 23 kDa was detected from THP-1 cells infected with rLM/IglC, but not from the mock-infected cells or cells infected with rLM/ΔActA. Similarly, a major protein band of 80 kDa was detected only from cells infected with rLM/KatG. These results indicated that the recombinant *L. monocytogenes* strains were taken up by the human macrophage-like cells and the *F. tularensis* proteins were properly expressed by the intracellular recombinant *L. monocytogenes* strains.

Replication-defective adenovirus expressing virulent *F. tularensis* antigen Tul4. The gene encoding the mature peptide of Tul4 was subcloned from pZErO vector into a transfer vector of pAdenoVator-CMV5 downstream of a modified immediate-early promoter of cytomegalovirus (CMV5), which allows for the production of high levels of heterologous proteins in mammalian cells. The replication-defective adenovirus expressing *F. tularensis* Tul4 protein will be generated in a way that was similar to that described for AdvΔE1E3/Ft KatG in the previous application.

Expression of *F. tularensis* Tul4 protein in recombinant *E. coli*. The nucleotide sequence encoding the mature peptide of tul4 was amplified from the genomic DNA of *F. tularensis* RCI and cloned into pZErO vector (Invitrogen). Identity of the amplified gene in pZErO was confirmed by nucleotide sequencing. The Tul4 coding gene was subsequently cloned into the NdeI and BamHI sites of the expression vector pET-15b (Novagen), which was then transformed into *E. coli* BL21 CodonPlus (DE3)-RIL strain. The expression construct is designed to produce and export *F. tularensis* Tul4 with a short tag of 6 histidine residues at the N-terminus by the recombinant *E. coli*.

The expression of Tul4 was tested by inoculating 1.0 ml of an overnight culture of the recombinant *E. coli* into 25 ml LB medium containing carbenicillin. The culture was grown for 3 h with rotation before addition of 1 mM IPTG. The culture was continued for an additional 4 h before harvesting by centrifugation. The cell pellet was sonicated and subjected to analysis by SDS-PAGE and coomassie blue staining and by Western blotting. The induction of Tul4 by IPTG in the soluble fraction of the recombinant *E. coli* culture was apparent by the presence of a major protein band, corresponding to the molecular mass of mature Tul4 plus the 6-His tag (~17 kD). The expression of His-tagged Tul4 was further confirmed by Western blot analysis using a monoclonal antibody to the 6-His tag or a monoclonal antibody to the Tul4 protein.

Isolation of purified *F. tularensis* Tul4 protein and generation of polyclonal antibody to Tul4. The Tul4 protein was isolated and purified from the soluble portion of the recombinant *E. coli* culture. 100 ml LB medium containing carbenicillin (100 µg ml$^{-1}$) and chloramphenicol (50 µg ml$^{-1}$) was inoculated with 0.5 ml stock of the recombinant *E. coli* expressing Tul4 and cultured overnight at 37° C., 250 rpm. The 100 ml overnight culture was then inoculated into fresh 2 liter LB medium containing carbenicillin and chloramphenicol and grown at 37° C., 250 rpm for 2 h before the addition of 1 mM IPTG. The recombinant *E. coli* culture was then allowed to grow for an additional 4 h before harvesting by centrifugation. The bacterial pellet was suspended in 100 ml native lysis buffer supplemented with 20 µM PMSF, lysed for 30 min on ice in the presence of lysozyme, sonicated, and the lysate centrifuged for 30 min at 10,000×g at 4° C. The cleared lysate was then allowed to bind to a Ni-NTA column. Proteins bound to the column were eluted first with a linear gradient of imidazole from 20 mM to 100 mM followed by a second linear gradient of imidazole from 100 mM to 250 mM. Fractions collected from the Ni-column were analyzed by SDS-PAGE and staining with coomassie blue. Fractions containing the most abundant recombinant Tul4 were combined, concentrated, and dialyzed against buffer containing 50 mM Tris, pH 7.5. The yield of the recombinant Tul4 recovered from the affinity Ni-column purification was determined by the Bradford protein assay to be 36 mg.

A portion of the Ni-column purified recombinant Tul4 protein was treated with avidin-thrombin to cleave the N-terminal 6-His tag off the recombinant Tul4 protein. Thrombin was then captured and removed from the cleavage mixture by incubating with agarose coated with streptavidin, which binds avidin specifically with high affinity. The remaining cleavage mixture was loaded onto the Ni-NTA column a second time. Recombinant Tul4 with the histidine-tag removed was unable to bind Ni-NTA resin and therefore passed through the column directly. The purity of the Tul4 protein after this purification step was confirmed by SDS-PAGE analysis of fractions collected from the second Ni-column, which contained one major protein band of 16 kDa corresponding to Tul4 and a minor band of 35 kDa. The identity of the 35-kDa band was unknown but it was recognized by a monoclonal antibody to Tul4. The fractions containing the major Tul4 protein were combined and dialyzed extensively against PBS. The final product of the Tul4 protein was aliquoted and stored at −80° C. A small portion of the purified Tul4 protein (1250 µg) was used to immunize two rabbits for generation of the polyclonal antibody to Tul4 (Covance).

In vivo Immunogenicity of recombinant *Listeria monocytogenes* strains expressing *F. tularensis* proteins. BALB/c mice (3 mice/group) were immunized intradermally twice at weeks 0 and 3 with normal saline (sham), LVS (1~10$^4$ CFU/mouse, positive control), the parental rLM strain (rLM/ΔactA), or rLM expressing virulent *F. tularensis* antigens IglC (rLM/IglC), KatG (rLM/KatG) or the combination of rLM/IglC and rLM/KatG (1×10$^6$ CFU of each vaccine/mouse). One week after the final immunization, mice were sacrificed; Splenocytes were prepared and tested for expression of IFNγ.

Figure 6:
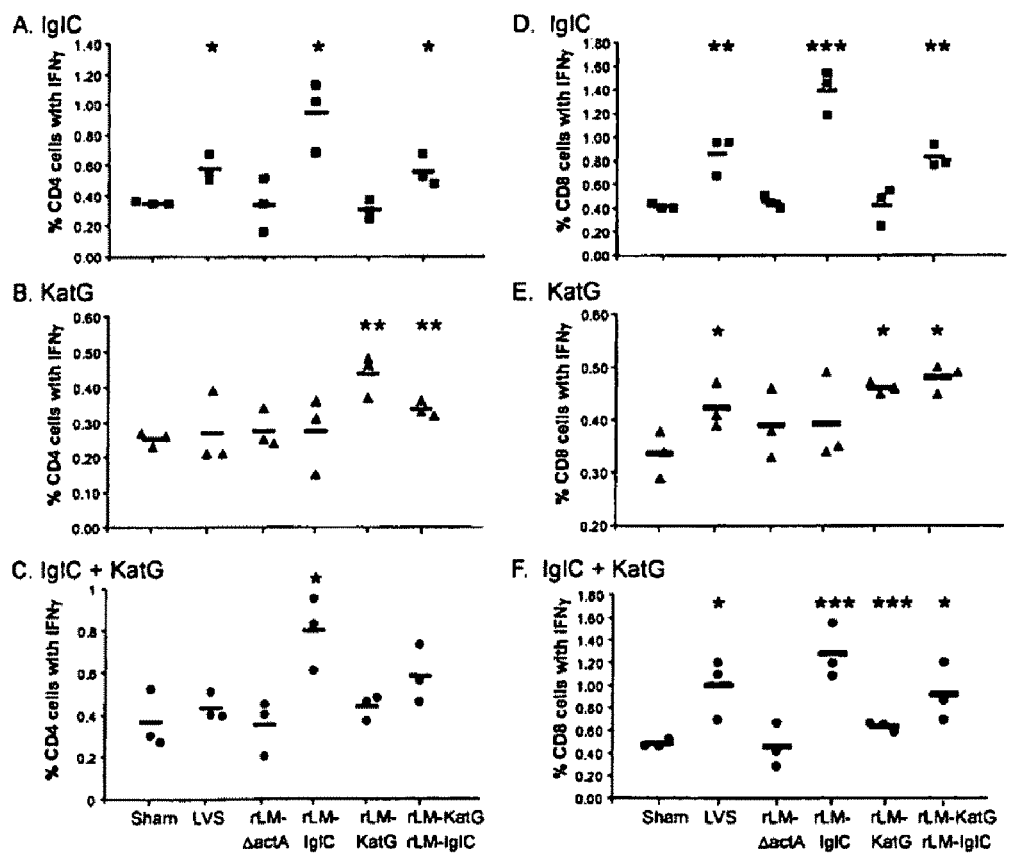
FIG. 6A-F shows T-cell immune response to recombinant attenuated *L. monocytogenes* vaccines. BALB/c mice (3/group) were immunized intradermally twice at weeks 0 and 3 with normal saline (sham), LVS, or rLM strains. Splenocytes were prepared at week 4 and incubated in RPMI medium containing 10% FBS and interleukin 2 (50 U/ml) with or without purified protein antigens, IglC (A and D), KatG (B and E), or IglC+KatG (C and F) (10 µg/ml) for 24 h at 37° C./5% $CO_2$. Golgi-Plug (BD Pharmingen) was added, and the cells were incubated for an additional 11 h and harvested. The pelleted cells were resuspended in staining buffer containing Fc-Block. Cells were stained with FITC-conjugated rat anti-mouse CD4 (A, B and C) or PE-Cy5-conjugated anti-mouse CD8 monoclonal antibody (D, E, and F). Cells were washed and fixed per protocol and stained for intracellular IFNγ with PE-conjugated rat anti-mouse IFNγ. Stained cells were analyzed on a FACSCalibur flow cytometer using CellQuest software. Statistical comparisons are values for animals immunized with live LVS or rLM strains vs. values for sham-immunized animals, * indicates $P<0.05$; , $p<0.01$; and *, $p<0.001$.

As shown in FIG. 6, sham-immunized animals and animals immunized with the vector control had relatively low responses. LVS-immunized animals showed strong CD4+ and CD8+ T cell responses to IglC (A and D) and strong CD8+ T cell response to KatG (B and E) that were significantly increased compared with the responses of sham-immunized animals. Animals immunized with rLM/IglC showed significantly increased CD4+ and CD8+ T cell responses to IglC (A and D) or the combination of IglC plus KatG (C and F) but not to KatG alone (B and E) compared with sham- or vector-immunized animals. Animals immunized with rLM/KatG showed significantly increased CD4+ and CD8+ responses to KatG (B and E) but not to IglC (A and D) compared with sham-immunized animals. Animals immunized with the combination of rLM/IglC and rLM/KatG showed significantly increased CD4+ and CD8+ T cell responses to IglC (A and D), KatG (B and E) or the combination of IglC and KatG (C and F) compared with sham-immunized controls. These results are consistent with other results and indicate that both IglC and KatG are actively produced post immunization by the attenuated rLM vaccines expressing these proteins and are processed and presented to T cells. The rLM expressing IglC induces stronger CD4+ and CD8+ T cell immune responses to IglC (~1-1.40 of CD4 and CD8 cells express IFNγ) than the rLM expressing KatG does to KatG (~0.40 of CD4 and CD8 cells express IFNγ).

The recombinant *Listeria monocytogenes* strains expressing *F. tularensis* IglC and KatG (rLM/IglC or rLM/KatG) were also demonstrated to protect against aerosol challenge with the highly virulent Type A *F. tularensis* subspecies *tularensis* Schu4 Strain.

A number of embodiments have been described. Nevertheless, it will be understood that various modifications may be made without departing from the spirit and scope of the description. Accordingly, other embodiments are within the scope of the following claims.

---

What is claimed is:

1. An immunoprotective composition comprising at least one attenuated *F. tularensis* LVS that lacks a functional O-antigen or has one or more disrupted genes required for producing a functional O-antigen and expressing an antigen useful for inducing an immunoprotective response against *Francisella tularensis*, said antigen comprising an extracellular or immunogenic polypeptide of *F. tularensis* or immunogenic fragment thereof selected from the group consisting of AcpA, Bfr, DnaK, FabD, GroEL, IglC, KatG, Pld, Tul4, SodB, and any combination thereof.

2. The immunoprotective composition of claim 1, wherein the disrupted genes required for producing a functional O-antigen are selected from a group consisting of wbtD, wbtE, and wbtF.

3. The immunoprotective composition of claim 1, wherein the polypeptide or fragment is KatG and/or IglC antigen of *F. tularensis*.

4. The immunoprotective composition of claim 3, wherein the polypeptide or fragment is IglC of *F. tularensis*.

5. The immunoprotective composition of claim 1, wherein the composition has at least one biological effect when administered to a subject selected from the group consisting of,
reducing the risk from acquiring an infection caused by *F. tularensis*;
preventing or at least partially arresting the development of a *F. tularensis* infection;
reducing the severity and incidence of complications resulting from an *F. tularensis* infection;
ameliorating an *F. tularensis* infection; and
stimulating an immune response against *F. tularensis*.

6. The immunoprotective composition of claim 1, wherein the composition has at least one biological effect when administered to a subject selected from the group consisting of,
inducing the production of *F. tularensis* antigen-specific T cells in a subject;
inducing the production of *F. tularensis* antigen-specific B cells in a subject; and
inducing the production of *F. tularensis* antigen-specific antibodies in a subject.

7. The immunoprotective composition of claim 6, wherein the *F. tularensis* antigen is either KatG and/or IglC.

8. The immunoprotective composition of claim 1, wherein the polypeptide comprises a sequence selected from the group consisting of SEQ ID NO: 12 and/or 14.

9. The immunoprotective composition of claim 1, further comprising a pharmaceutical diluent.

10. The immunoprotective composition of claim 1, wherein the polypeptide comprises a sequence selected from the group consisting of SEQ ID NO:2, 4, 6, 8, 10, 12, 14, 16, 18, 20, an immunogenic fragment thereof, and any combination of the foregoing.

11. A substantially purified recombinant attenuated *F. tularensis* that lacks a functional O-antigen and comprising a polynucleotide encoding at least one extracellular or immunogenic protein, or fragment thereof, of *F. tularensis* selected from the group consisting of AcpA, Bfr, DnaK, FabD, GroEL, IglC, KatG, Pld, Tul4, and SodB and any combination thereof that induces a protective immunity against *F. tularensis*.

12. The immunoprotective composition of claim 1, wherein the polypeptide or fragment is IglC of *F. tularensis*.

* * * * *